(12) United States Patent
Saitou et al.

(10) Patent No.: US 9,938,496 B2
(45) Date of Patent: Apr. 10, 2018

(54) METHOD OF INDUCING DIFFERENTIATION FROM PLURIPOTENT STEM CELLS TO GERM CELLS

(75) Inventors: Mitinori Saitou, Kyoto (JP); Katsuhiko Hayashi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 13/816,681

(22) PCT Filed: Jul. 28, 2011

(86) PCT No.: PCT/JP2011/067816
§ 371 (c)(1),
(2), (4) Date: Feb. 21, 2013

(87) PCT Pub. No.: WO2012/020687
PCT Pub. Date: Feb. 16, 2012

(65) Prior Publication Data
US 2013/0143321 A1    Jun. 6, 2013

Related U.S. Application Data

(60) Provisional application No. 61/373,563, filed on Aug. 13, 2010.

(51) Int. Cl.
*C12N 5/00* (2006.01)
*C12N 5/071* (2010.01)
*C12N 5/0735* (2010.01)

(52) U.S. Cl.
CPC ......... *C12N 5/0602* (2013.01); *C12N 5/0606* (2013.01); *C12N 5/0611* (2013.01); *C12N 2501/11* (2013.01); *C12N 2501/115* (2013.01); *C12N 2501/125* (2013.01); *C12N 2501/155* (2013.01); *C12N 2501/16* (2013.01); *C12N 2501/235* (2013.01); *C12N 2506/02* (2013.01); *C12N 2506/45* (2013.01); *C12N 2533/56* (2013.01)

(58) Field of Classification Search
CPC .................................................. C12N 5/0611
See application file for complete search history.

(56) References Cited

U.S. PATENT DOCUMENTS

2016/0010056 A1   1/2016 Nakaki et al.

FOREIGN PATENT DOCUMENTS

| EP | 2 169 051 A1 | 3/2010 |
|----|--------------|--------|
| WO | 2008/056173 A2 | 5/2008 |
| WO | WO 2014/133194 A1 | 9/2014 |

OTHER PUBLICATIONS

D'Amour et al. teach a method of culturing human ES cells with Activin A, see Fig. 1, (2006, Nature Biotechnology, vol. 24(11), pp. 1392-1401).*
Brons et al. (2007, Nature, vol. 448, pp. 191-196).*
Ohinata et al. (2009, Cell, vol. 137, pp. 571-584).*
Jung et al. (2005, Stem Cells, vol. 23, pp. 689-698).*
Morita-Fujimura et al. (2009, Develop. Growth Differ., vol. 51, pp. 567-583).*
D'Amour et al. (2006, Nature Biotechnology, vol. 24(11), pp. 1392-1401).*
Park et al. (2009, Stem Cells, vol. 27, pp. 783-795).*
International Stem Cell Registry, 1 page web printout.*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Brons et at., *Nature*, 448(7150): 191-195 (2007).
Bucay et al., *Stem Cells*, 27: 68-77 (2009).
Clark et al., *Human Molecular Genetics*, 13(7): 727-739 (2004).
Daley, George Q., *Science*, 316(5823): 409-410-(2007).
Geijsen et al., *Nature*, 427(6970): 148-154 (2004).
Guo et al., *Development*, 136(7): 1063-1069 (2009).
Hayashi et al., *Cell*, 146(4): 519-532 (2011).
Hayashi et al., *Development*, 136(21): 3549-3556 (2009).
Hayashi et al., *Science*, 338(6109): 971-975 (2012).
Hubner et al., *Science*, 300(5623): 1251-1256 (2003).
James et al., *Development*, 132(6): 1273-1282 (2005).
Kee et al., *Stem Cells and Development*, 15: 831-837 (2006).
Kee et al., *Nature*, 462: 222-225 (2009).
Kurimoto et al., *Genes & Development*, 22: 1617-1635 (2008).
Mathews et al., *Cell Stem Cells*, 5: 11-14 (2009).
Nayernia et al., *Developmental Cell*, 11(1): 125-132 (2009).
Ohinata et al., *Cell*, 137(3): 571-584 (2009).
Ohinata et al., *Nature*, 436: 207-213 (2005).
Park et al., *Stem Cells*, 27: 783-795 (2009).
Pearson et al., *Development*, 135(8): 1525-1535 (2008).
Saitou et al., *Reproduction*, 139(6): 931-942 (2010).
Tesar et al., *Nature*, 448(7150): 196-199 (2007).
Tilgner et al., *Stem Cells*, 26: 3075-3085 (2008).
Toyooka et al., *Proc. Natl. Acad. Sci. USA*, 100(20): 11457-11462 (2003).
West et al., *Nature*, 460: 909-913 (2009).
Yamaji et al., *Nature Genetics*, 40: 1016-1022 (2008).
European Patent Office, Extended European Search Report in European Patent Application No. 11816353.4 (dated Mar. 19, 2014).
Japanese Patent Office, International Search Report in International Patent Application No. PCT/JP2011/067816 (dated Nov. 8, 2011).
Chu et al., *Curr. Biol.*, 21(20): 1759-1765 (2011).
Gillich et al., *Cell Stem Cell*, 10(4): 425-439 (2012).
Grabole et al., *EMBO Rep.*, 14(7): 629-637 (2013).
John et al., *Exp. Cell. Res.*, 315(7): 1077-1084 (2009).
Kurimoto et al., *Cell Cycle*, 7(22): 3514-3518 (2008).

(Continued)

*Primary Examiner* — Thaian N Ton
(74) *Attorney, Agent, or Firm* — Leydig, Voit & Mayer, Ltd.

(57) ABSTRACT

This invention provides a method of producing an epiblast-like cell (EpiLC) from a pluripotent stem cell, which comprises culturing the pluripotent stem cell in the presence of activin A; a method of producing a primordial germ cell-like (PGC-like) cell a pluripotent stem cell, which comprises culturing the EpiLC obtained by the method above in the presence of BMP4 and LIF. Also provided are a cell population containing PGC-like cells as obtained by the method, and reagent kits for the EpiLC- and PGC-like cell-induction from a pluripotent stem cell.

12 Claims, 32 Drawing Sheets
(30 of 32 Drawing Sheet(s) Filed in Color)

(56) References Cited

OTHER PUBLICATIONS

Lawson et al., *Genes Dev.*, 13(4): 424-436 (1999).
Leitch et al., *Nat. Struct. Mol. Biol.*, 20(3): 311-316 (2013).
Magnusdottir et al., *Nat. Cell Biol.*, 15(8): 905-915 (2013).
Nakaki et al., *Nature*, 501(7466): 222-226 (2013).
Nagamatsu et al., *J. Biol. Chem.*, 286(12): 10641-10648 (2011).
Vincent et al., *Development*, 132(6): 1315-1325 (2005).
Japanese Patent Office, International Search Report in International Patent Application No. PCT/JP2014/055888 (dated May 27, 2014).
Bao et al., "The Germ Cell Determinant Blimp1 is Not Required for Derivation of Pluripotent Stem Cells," *Cell Stem Cell*, 11(1): 110-117 (2012).

\* cited by examiner

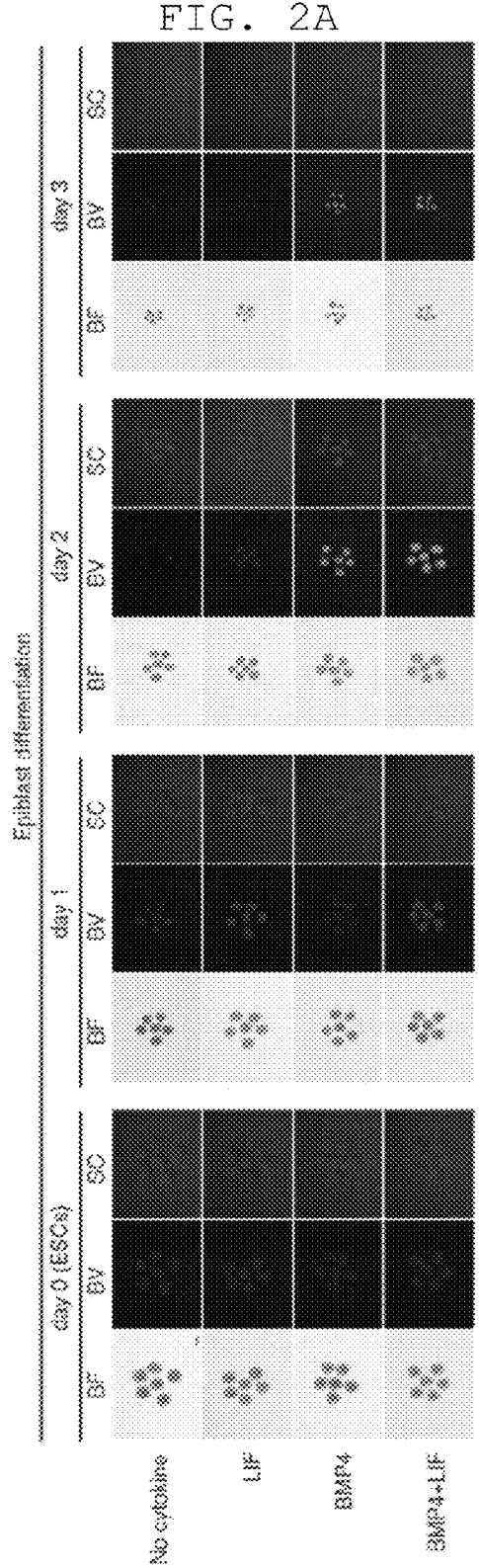

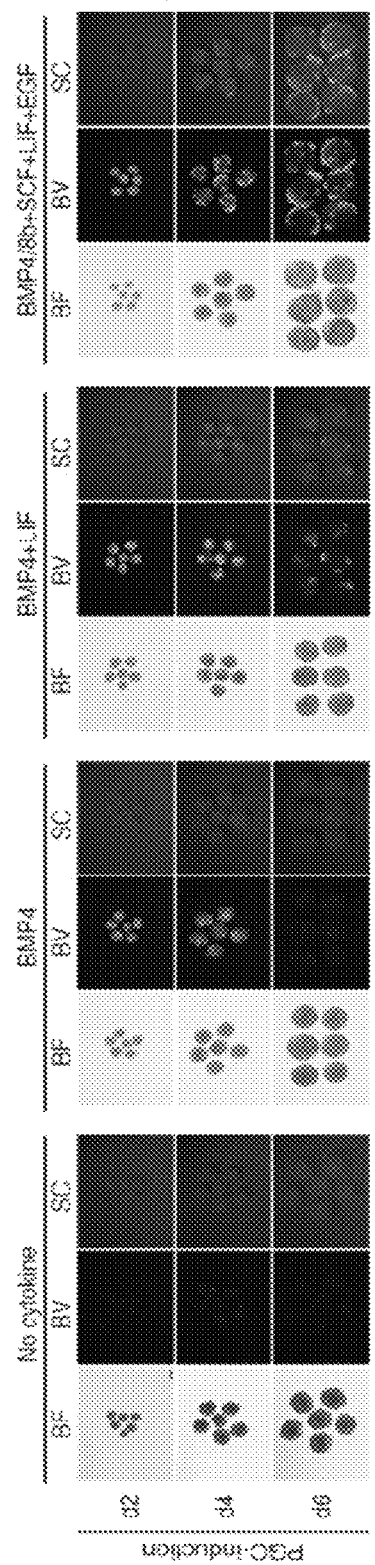

SEQUENCE LISTING

<160> NUMBER OF SEQ ID NOS: 93

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gatgctgtga gccaaggcaa g                                        21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ggctcctgat caacagcatc ac                                       22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
catgagagca agtactggca ag                                       22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ccaacgatat caacctgcat gg                                       22

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ctttcaccta ttaaggtgct tgc                                      23

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tggcatcggt tcatcatggt ac                                       22

<210> SEQ ID NO 7
<211> LENGTH: 22
<212> TYPE: DNA
<213> ORGANISM: Artificial Sequence -continued

```
<220> FEATURE:
<223> OTHER INFORMATION: Primer

<400> SEQUENCE: 7
agcatgacct gacattgaca cc                                              22

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ctcaacactc tcatgtaaga ggc                                             23

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
acagccaagc aatttgcact ac                                              22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ttacctggca ttttcattgc tc                                              22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gggctttcct ctcttggctg gt                                              22

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tccacacgtc acccacacaa                                                 20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
cactacggcc taggagcttg g                                               21
```

-continued

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tgatcgctga caagactgtg g                                           21

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
aggctcgaag gaaatgagtt tg                                          22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tcctaattct tcccgatttt cg                                          22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gggcagcctc aaaagcactc                                             20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cgtggcttca gcacggctat                                             20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ccctaaatgg gttaagcaga gc                                          22

<210> SEQ ID NO 20
<211> LENGTH: 23
<212> TYPE: DNA
<213> ORGANISM: Artificial Sequence
<220> FEATURE:
<223> OTHER INFORMATION: Primer

```
<400> SEQUENCE: 20
ggcaaggttc ctcacaacta aag                                              23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gatcctacag gtcttgggac c                                                21

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
agctcaaagg cactgaactg ag                                               22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gtgactagtc ttctgcatgt cg                                               22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tctgctctgg accacatcac tc                                               22

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
agcagggtgg ttactggaca c                                                21

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ccattattca tggtcccttc tg                                               22

<210> SEQ ID NO 27
```

```
<211> LENGTH: 21
<212> TYPE: DNA
<213> ORGANISM: Artificial Sequence
<220> FEATURE:
<223> OTHER INFORMATION: Primer

<400> SEQUENCE: 27
aaagaggagg ctgctaccaa g                                            21

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
ccacagacac tgagcacaag ac                                           22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
gttacagcct gtactgagga ag                                           22

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
tagaactgtg ctgtccagtc tg                                           22

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
gactcgcgtg caataacctt ag                                           22

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ggtcactttc cctcactctg g                                            21

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
```
ctcgcaaggt gtgggctttt gtaac                                       25

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ctgggcatct gtcatctttg cacc                                        24

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
aaggagaacg gttccttctg ac                                          22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
gctgaagctt acagtcccaa ag                                          22

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
tatgtgcctc ccagcttcag ta                                          22

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
ctggattggg agcttgtgaa ga                                          22

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tccttgactt gtggttgctg                                             20

<210> SEQ ID NO 40
<211> LENGTH: 20
<212> TYPE: DNA

```
<213> ORGANISM: Artificial Sequence
<220> FEATURE:
<223> OTHER INFORMATION: Primer

<400> SEQUENCE: 40
ccaccttcga ggttttacca                                                   20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
tccatggcat agttccaaca g                                                 21

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
taactgattt tctgccgtat gc                                                22

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
ttatttccag gtcaggagat ggc                                               23

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
ggtcgtttga accaagtccc tc                                                22

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tggcctcact agaacaagag g                                                 21

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
ctcggtcaag gatggaagc                                                    19
```

-continued

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
caggcaagga tgacagacg                                                    19

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gagacagcac gaaggactgc                                                   20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
tcgaggctag atgccttgtg a                                                 21

<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50
aaacgaagca ggcggcaga                                                    19

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tggtgcttgg tgagttgtgg                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
gctcccccgt ttggtaccttt                                                  20

<210> SEQ ID NO 53
<211> LENGTH: 20
<212> TYPE: DNA
<213> ORGANISM: Artificial Sequence
<220> FEATURE:

<223> OTHER INFORMATION: Primer

<400> SEQUENCE: 53
tacgggcgag aagccctaca                                            20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
ggcacaccat gcactggaac                                            20

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
aaagtcaatg gctcccacga a                                          21

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
cttcagtctg tacttcact                                             19

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
caagcacaac aatgaagcag gc                                         22

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
tcgggactca cggtgtttct c                                          21

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
atcagagtcc tttgctaggt ag                                         22

```
<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
gttacaatct tctggctatg c                                            21

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ttcctctccc aggaacatca aa                                           22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gctgcacaac tgggctctac tt                                           22

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
tgcaagattg catcatgaca ga                                           22

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
tgacctcaga tcagccacgt ta                                           22

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65
ttctgtacac tttaatgagg ctgttc                                       26

<210> SEQ ID NO 66
<211> LENGTH: 20
<212> TYPE: DNA
<213> ORGANISM: Artificial Sequence
<220> FEATURE:
<223> OTHER INFORMATION: Primer
```

```
<400> SEQUENCE: 66
ttgtgggaag tgggatcaag                                          20

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
caaagctgaa gcaaaggaag ag                                       22

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
aattaagcag gctgacttgg ttg                                      23

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
ttacccatca aaccattcct tctg                                     24

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
aacccaaaga acttcagtga gagc                                     24

<210> SEQ ID NO 71
<211> LENGTH: 26
<212> TYPE: DNA
<213> ORGANISM: Artificial Sequence
<220> FEATURE:
<223> OTHER INFORMATION: Primer

<400> SEQUENCE: 71
ttagtggggt atttttattt gtatgg                                   26

<210> SEQ ID NO 72
<211> LENGTH: 26
<212> TYPE: DNA
<213> ORGANISM: Artificial Sequence
<220> FEATURE:
<223> OTHER INFORMATION: Primer

<400> SEQUENCE: 72
aaatatccta aaaatacaaa ctacac                                   26

<210> SEQ ID NO 73
<211> LENGTH: 26
```

```
<212> TYPE: DNA
<213> ORGANISM: Artificial Sequence
<220> FEATURE:
<223> OTHER INFORMATION: Primer

<400> SEQUENCE: 73
gtgtggtatt tttatgtata gttagg                                              26

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
gagtatttag gaggtataag aatt                                                24

<210> SEQ ID NO 75
<211> LENGTH: 23
<212> TYPE: DNA
<213> ORGANISM: Artificial Sequence
<220> FEATURE:
<223> OTHER INFORMATION: Primer

<400> SEQUENCE: 75
atcaaaaact aacataaacc cct                                                 23

<210> SEQ ID NO 76
<211> LENGTH: 25
<212> TYPE: DNA
<213> ORGANISM: Artificial Sequence
<220> FEATURE:
<223> OTHER INFORMATION: Primer

<400> SEQUENCE: 76
gtaaggagat tatgtttatt tttgg                                               25

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
cctcattaat cccataacta t                                                   21

<210> SEQ ID NO 78
<211> LENGTH: 29
<212> TYPE: DNA
<213> ORGANISM: Artificial Sequence
<220> FEATURE:
<223> OTHER INFORMATION: Primer

<400> SEQUENCE: 78
tatgtaatat gatatagttt agaaattag                                           29

<210> SEQ ID NO 79
<211> LENGTH: 29
<212> TYPE: DNA
<213> ORGANISM: Artificial Sequence
<220> FEATURE:
<223> OTHER INFORMATION: Primer

<400> SEQUENCE: 79
```
aataaaccca aatctaaaat attttaatc                                           29

<210> SEQ ID NO 80
<211> LENGTH: 28
<212> TYPE: DNA
<213> ORGANISM: Artificial Sequence
<220> FEATURE:
<223> OTHER INFORMATION: Primer

<400> SEQUENCE: 80
aatttgtgtg atgtttgtaa ttatttgg                                            28

<210> SEQ ID NO 81
<211> LENGTH: 28
<212> TYPE: DNA
<213> ORGANISM: Artificial Sequence
<220> FEATURE:
<223> OTHER INFORMATION: Primer

<400> SEQUENCE: 81
aatttgtgtg atgtttgtaa ttatttgg                                            28

<210> SEQ ID NO 82
<211> LENGTH: 31
<212> TYPE: DNA
<213> ORGANISM: Artificial Sequence
<220> FEATURE:
<223> OTHER INFORMATION: Primer

<400> SEQUENCE: 82
atttttgtgg tttaggttta tagaagtagg g                                        31

<210> SEQ ID NO 83
<211> LENGTH: 31
<212> TYPE: DNA
<213> ORGANISM: Artificial Sequence
<220> FEATURE:
<223> OTHER INFORMATION: Primer

<400> SEQUENCE: 83
ttaaaaatca ccacaacata aataactata t                                        31

<210> SEQ ID NO 84
<211> LENGTH: 30
<212> TYPE: DNA
<213> ORGANISM: Artificial Sequence
<220> FEATURE:
<223> OTHER INFORMATION: Primer

<400> SEQUENCE: 84
tagaagtagg ggtggttttg aggtttttg                                           30

<210> SEQ ID NO 85
<211> LENGTH: 31
<212> TYPE: DNA
<213> ORGANISM: Artificial Sequence
<220> FEATURE:
<223> OTHER INFORMATION: Primer

<400> SEQUENCE: 85
ccacaacata aataactata ttaaaaaatc a                                        31

<210> SEQ ID NO 86
<211> LENGTH: 22
<212> TYPE: DNA
<213> ORGANISM: Artificial Sequence

```
<220> FEATURE:
<223> OTHER INFORMATION: Primer

<400> SEQUENCE: 86
actcatctca gaagaggatc tg                                              22

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
cacagtcgag gctgatctcg                                                 20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
cgagctagct tttgaggctt                                                 20

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
aacttgtggc cgtttacgtc                                                 20

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
gacgtaaacg gccacaagtt c                                               21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
aagtcgtgct gcttcatgtg                                                 20

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
ctgagggcca ggcaggagca cgag                                            24
```

```
<210> SEQ ID NO 93
<211> LENGTH: 24
<212> TYPE: DNA
<213> ORGANISM: Artificial Sequence
<220> FEATURE:
<223> OTHER INFORMATION: Primer

<400> SEQUENCE: 93
ctgtagggag ggcttcgggc actt                                          24
```

US 9,938,496 B2

METHOD OF INDUCING DIFFERENTIATION FROM PLURIPOTENT STEM CELLS TO GERM CELLS

CROSS-REFERENCE TO RELATED APPLICATIONS

This patent application is the U.S. national phase of PCT/JP2011/067816, filed on Jul. 28, 2011, which claims the benefit of U.S. Provisional Patent Application No. 61/373,563, filed August 13, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 16,944 bytes ASCII (Text) file named "712298SequenceListing.txt," created Feb. 12, 2013.

TECHNICAL FIELD OF THE INVENTION

The present invention relates to a method of inducing primordial germ cell-like cells (PGC-like cells) from pluripotent stem cells via epiblast-like cells (EpiLCs), a reagent kit therefor, a cell population containing EpiLCs obtained from the method and a method of inducing cells belonging to the germ cell lineage derived from epiblast from the cell population.

BACKGROUND OF THE INVENTION

A key challenge in developmental biology is to reconstruct critical developmental pathways in vitro, which not only provides novel experimental opportunities but also serves as a basis for medical applications. In multicellular organisms, the germ cell lineage is endowed with the critical function of ensuring the creation of new organisms, thereby perpetuating the genetic and epigenetic information across the generations. The reconstruction of the development of the germ cell lineage in vitro is therefore of fundamental significance in the life sciences in general. There have been several attempts to generate gametes or their progenitors (primordial germ cells: PGCs) in vitro from embryonic stem cells (ESCs) derived from the inner cell mass (ICM) of blastocysts in mice[1,2,3,4,5] and humans [6,7,8,9,10,11] (see also the reviews in[12,13,14]). However, all these attempts involved random differentiation of ESCs as embryoid bodies under undefined conditions and relied on spontaneous expression of a marker gene(s). Consequently, these efforts were inefficient at obtaining the cells of interest. Moreover, the cells created have never been demonstrated to contribute to the generation of healthy offspring.

We have identified key transcriptional regulators, Blimp1 (also known as Prdm1) and Prdm14, for the specification of the germ cell lineage from the epiblast[15,16], and uncovered a genome-wide transcriptional dynamics associated with PGC specification[17]. Recently, we defined a signalling principle for PGC specification from the epiblast and showed that essentially all the epiblast cells in mice from embryonic day (E) 5.5 to E6.0 but not those later than E6.25 were efficiently and reproducibly induced into Blimp1-, Prdm14-, stella-, and alkaline phosphatase (AP)-positive PGC-like cells by cytokines including BMP4 under serum- and feeder-free, defined conditions (serum-free medium: SFM) in a floating culture[18]. When transplanted into the testes of neonatal W/W$^v$ mice lacking germ cells, the induced PGC-like cells underwent proper spermatogenesis and contributed successfully to the generation of the healthy offspring[18]. These findings demonstrate that an efficient and reproducible induction of PGCs with proper function from pluripotent stem cells such as ESCs or induced pluripotent stem cells (iPSCs) in culture, the essential first step of the reconstruction of germ cell development in vitro, may be achieved through initial differentiation of pluripotent stem cells into epiblast-like cells bearing properties of the pre-gastrulating epiblast cells at E5.5-E6.0. However, culture conditions capable of efficiently and reproducibly inducing the pre-gastrulating epiblast-like cells (EpiLCs) from pluripotent stem cells have not been found.

REFERENCES CITED

1. Hubner, K. et al. Derivation of oocytes from mouse embryonic stem cells. *Science* 300, 1251-1256 (2003).
2. Toyooka, Y., Tsunekawa, N., Akasu, R. & Noce, T. Embryonic stem cells can form germ cells in vitro. *Proc Natl Acad Sci USA* 100, 11457-11462 (2003).
3. Geijsen, N. et al. Derivation of embryonic germ cells and male gametes from embryonic stem cells. *Nature* 427, 148-154 (2004).
4. Nayernia, K. et al. In vitro-differentiated embryonic stem cells give rise to male gametes that can generate offspring mice. *Dev Cell* 11, 125-132 (2006).
5. West, J. A. et al. A role for Lin28 in primordial germ-cell development and germ-cell malignancy. *Nature* 460, 909-913, doi:nature08210 [pii] 10.1038/nature08210 (2009).
6. Clark, A. T. et al. Spontaneous differentiation of germ cells from human embryonic stem cells in vitro. *Hum Mol Genet.* 13, 727-739, doi:10.1093/hmg/ddh088 ddh088 [pii] (2004).
7. Kee, K., Gonsalves, J. M., Clark, A. T. & Pera, R. A. Bone morphogenetic proteins induce germ cell differentiation from human embryonic stem cells. *Stem Cells Dev* 15, 831-837, doi:10.1089/scd.2006.15.831 (2006).
8. Tilgner, K. et al. Isolation of primordial germ cells from differentiating human embryonic stem cells. *Stem Cells* 26, 3075-3085, doi:2008-0289 [pii] 10.1634/stemcells.2008-0289 (2008).
9. Bucay, N. et al. A novel approach for the derivation of putative primordial germ cells and sertoli cells from human embryonic stem cells. *Stem Cells* 27, 68-77, doi: 2007-1018 [pii] 10.1634/stemcells.2007-1018 (2009).
10. Kee, K., Angeles, V. T., Flores, M., Nguyen, H. N. & Reijo Pera, R. A. Human DAZL, DAZ and BOULE genes modulate primordial germ-cell and haploid gamete formation. *Nature* 462, 222-225, doi:nature08562 [pii] 10.1038/nature08562 (2009).
11. Park, T. S. et al. Derivation of primordial germ cells from human embryonic and induced pluripotent stem cells is significantly improved by coculture with human fetal gonadal cells. *Stem Cells* 27, 783-795, doi:10.1002/stem.13 (2009).
12. Daley, G. Q. Gametes from embryonic stem cells: a cup half empty or half full? *Science* 316, 409-410 (2007).
13. Mathews, D. J. et al. Pluripotent stem cell-derived gametes: truth and (potential) consequences. *Cell Stem Cell* 5, 11-14, doi:S1934-5909(09)00289-6 [pii] 10.1016/j.stem.2009.06.005 (2009).
14. Saitou, M. & Yamaji, M. Germ cell specification in mice: signaling, transcription regulation, and epigenetic conse- 15. Ohinata, Y. et al. Blimp1 is a critical determinant of the germ cell lineage in mice. *Nature* 436, 207-213 (2005).
16. Yamaji, M. et al. Critical function of Prdm14 for the establishment of the germ cell lineage in mice. *Nat Genet.* 40, 1016-1022 (2008).
17. Kurimoto, K. et al. Complex genome-wide transcription dynamics orchestrated by Blimp1 for the specification of the germ cell lineage in mice. *Genes Dev* 22, 1617-1635 (2008).
18. Ohinata, Y. et al. A signaling principle for the specification of the germ cell lineage in mice. *Cell* 137, 571-584 (2009).

SUMMARY OF THE INVENTION

Therefore, an object of the present invention is to provide a method of inducing EpiLCs from pluripotent stem cells with high efficiency and reproducibility, thereby achieving a functional reconstruction of the germ-cell specification pathway from pluripotent stem cells including ESCs and iPSCs in vitro. It is another object of the present invention to provide a method of inducing germ cells from pluripotent stem cells under serum- and feeder-free conditions.

Epiblast stem cells (EpiSCs) are pluripotent stem cells derived from E5.5 to E6.5 epiblasts in the continuous presence of activin A and basic fibroblast growth factor (bFGF) in culture (*Nature* 448, 191-195 (2007); *Nature* 448, 196-199 (2007)), and are a potential candidate from which to induce PGC-like cells in vitro. However, the present inventors found that EpiSCs cultured under several conditions were not induced into Blimp1- and stella-positive cells efficiently in an SFM with BMP4. This might be because EpiSCs are not fully competent for the PGC fate, as reflected by their high-level expression of endoderm markers such as Gata6, Sox17, and Cer1, a property distinct from pre-gastrulating epiblasts.

Therefore, the present inventors tried to determine conditions under which pluripotent stem cells can be induced into the E5.5-E6.0 epiblast-like state, in order to achieve the above-described objects. At first, the present inventors produced mouse ESCs bearing the Blimp1-mVenus and stella-ECFP reporters (BVSC; Reproduction 136, 503-514 (2008)). Since PGCs specifically express Blimp1 (Prdm1) and stella (Dppa3), the mouse ESCs enable visualization of PGC differentiation therefrom. The reporter ESCs were maintained under a condition that keeps ESCs in the ~E3.5-E4.5 ICM/early epiblast-like state, and then cultured in an SFM supplemented with activin A, and optionally bFGF and KnockOut™ Serum Replacement (KSR) for 3 days. During the culture, the ESCs were uniformly differentiated into epiblast-like flattened cells, namely EpiLCs.

Then, the EpiLCs obtained were cultured in an SFM supplemented with BMP4, BMP4 and LIF, or BMP4, LIF, SCF, BMP8b and EGF. As a result, the EpiLCs were induced into Blimp1- and stella-positive PGC-like cells essentially in the presence of BMP4, and the maintenance/survival/proliferation of the PGC-like cells were enhanced by LIF and more robustly LIF, SCF, BMP8b and EGF.

The gene-expression dynamics associated with PGC-like cell induction from ESCs through EpiLCs were strikingly similar to those of PGC specification from the inner cell mass (ICM) through the epiblasts. Remarkably, the PGC-like cells contributed robustly to spermatogenesis and the generation of healthy offspring.

The present inventors conducted further investigations based on these findings, and have developed the present invention.

Accordingly, the present invention provides the following:

[1] A method of producing an epiblast-like cell (EpiLC) from a pluripotent stem cell, which comprises culturing the pluripotent stem cell in the presence of activin A;

[2] The method of [1] above, wherein the EpiLC shows elevated gene expression of at least one selected from Fgf5, Wnt3 and Dnmt3b compared to the pluripotent stem cell before inducing differentiation;

[3] The method of [1] or [2] above, wherein the EpiLC shows reduced gene expression of at least one selected from Gata4, Gata6, Sox17 and Blimp1 compared to the pluripotent stem cell before inducing differentiation;

[4] The method of any of [1]-[3] above, wherein the culture is performed in the presence of further basic fibroblast growth factor (bFGF) and/or KnockOut™ Serum Replacement (KSR);

[5] The method of any of [1]-[4] above, wherein the culture is performed under serum- and feeder-free conditions;

[6] The method of any of [1]-[5] above, wherein the culture is performed for less than 3 days;

[7] The method of [6] above, wherein the culture is performed for about 2 days;

[8] A method of producing a primordial germ cell-like (PGC-like) cell from a pluripotent stem cell, which comprises the following steps I) and II):
I) the step for producing an EpiLC according to the method of any of [1]-[7] above;
II) the step for culturing the EpiLC obtained in the step I) in the presence of BMP4 and LIF;

[9] The method of [8] above, wherein the PGC-like cell shows elevated gene expression of Blimp1 and/or Stella (Dppa3) compared to the EpiLC before inducing differentiation;

[10] The method of [8] or [9] above, wherein the PGC-like cell is capable of contributing to normal spermatogenesis;

[11] The method of any of [8]-[10] above, wherein the culture in the step II) is performed in the presence of further SCF and/or BMP8b and/or EGF;

[12] The method of any of [8]-[11] above, wherein the culture in the step II) is performed under serum-free conditions;

[13] The method of [8] above, wherein the culture in the step I) is performed in the presence of activin A, bFGF and KSR, and wherein the culture in the step II) is performed in the presence of BMP4, LIF, SCF, BMP8b and EGF;

[14] The method of any of [8]-[13] above, which further comprises:
III) the step for selecting a Blimp1-positive cell from the cells obtained in the step II);

[15] The method of any of [8]-[13] above, which further comprises:
III) the step for selecting a SSEA1- and Integrin-β3-double positive cell from the cells obtained in the step II);

[16] The method of any of [1]-[15] above, wherein the pluripotent stem cell is an induced pluripotent stem cell (iPSC) or embryonic stem cell (ESC);

[17] A reagent kit for inducing the differentiation from a pluripotent stem cell to an EpiLC comprising activin A, bFGF and KSR;

[18] A reagent kit for inducing the differentiation from a pluripotent stem cell to a PGC-like cell comprising the following (1) and (2):

(1) reagent(s) containing activin A, bFGF and KSR for inducing pluripotent stem cell into an EpiLC;
(2) reagent(s) containing BMP4, LIF, SCF, BMP8b and EGF for inducing an EpiLC to a PGC-like cell;

[19] The reagent kit of [17] or [18] above, wherein the pluripotent stem cell is an iPSC or ESC;

[20] A cell population containing EpiLCs, which is produced by the method of any of [1]-[7] above;

[21] The cell population of [20] above, wherein the EpiLCs have the following properties (1) and (2):
(1) elevated gene expression of at least one selected from Fgf5, Wnt3 and Dnmt3b compared to the pluripotent stem cells before inducing differentiation;
(2) reduced gene expression of at least one selected from Gata4, Gata6, Sox17 and Blimp1 compared to the pluripotent stem cells before inducing differentiation;

[22] The cell population of [20] or [21] above, wherein reprogramming gene(s) are integrated into the genomes of the cells constituting the cell population;

[23] The cell population of [22] above, wherein the reprogramming genes are 4 genes consisting of Oct3/4, Sox2, Klf4 and c-Myc, or 3 genes consisting of Oct3/4, Sox2 and Klf4; and

[24] A method of producing a variety of cell types derived from epiblast which comprises utilizing the cell population of any of [20]-[23] above as a cell source.

The indution of PGC-like cells from pluripotent stem cells of the present invention involves the induction of EpiLCs as an intermediate. EpiLCs are the culture equivalents of the E5.5-E6.0 epiblasts, the immediate precursors of PGCs. Thus, the inventive induction system is considered to be a precise and stepwise recapitulation in culture of the PGC-specification pathway from the ICM/early epiblasts in vivo. This notion is strongly supported by the gene expression dynamics associated with the PGC-like cell induction pathway, which is remarkably similar to that associated with the PGC specification pathway in vivo. Most notably, the induced PGC-like cells contributed to spermatogenesis with relatively high efficiency (3/6 transplanted testes positive for spermatogenesis) and to the generation of healthy offspring. This is the first demonstration of the production of healthy animals from germ line cells induced from ESCs or iPSCs in vitro.

The mechanism involved in the specification of PGCs and their subsequent development has been very difficult to explore, mainly because they are extremely small in number in vivo and refractory to proliferation in vitro. The inventive culture system readily allows the generation of PGC-like cells in a relatively large number ($\sim 10^5$-$10^6$) and therefore serves as a foundation for elucidating areas of germ cell biology that have thus far been unexplored (e.g., analyses of the biochemical properties of key proteins involved in PGC specification and proliferation/survival, the precise mechanism of epigenetic reprogramming in PGCs, etc.) due to material limitations. Furthermore, the generation of the PGC-like cells with proper function from pluripotent stem cells under a serum- and feeder-free condition is a critical first step for the reconstruction of germ cell development in vitro. In vitro reconstruction of germ cell development will be crucial for a more comprehensive understanding of germ cell biology in general as well as for the advancement of reproductive technology and medicine.

Furthermore, germ cell lineage such as sperm and egg is only one cell lineage that perpetuates genome information to the next generation and reconstitutes an individual. A developmental abnormality may result in infertility or transmission/development of hereditary diseases. Therefore, an in vitro reconstruction of the developmental processes will promote not only the elucidation of detailed developmental mechanisms of germ cells but also the elucidation of mechanisms of infertility and development of hereditary diseases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows an induction of epiblast-like cells (EpiLCs) from ESCs in culture.

FIG. 2 shows an induction of the PGC-like cells from EpiLCs in culture. FIG. 2A, The effects of LIF, BMP4, or both on the induction of Blimp1 (BV) in the floating 2-day culture of the ESCs, the day-1, -2, and -3 EpiLCs. The day-2 EpiLC cultures express BV efficiently in response to BMP4 or BMP4 and LIF. Bar, 200 μm. FIG. 2B, The effects of BMP4, or BMP4 and LIF, or BMP4, LIF, SCF, BMP8b, and EGF (full induction) on the induction of Blimp1 (BV) and stella (SC) in the floating 6-day culture of the ESCs, the day-1, -2, and -3 EpiLCs. The day-2 EpiLCs developed as PGC-like cells with robust BVSC expression under the full induction condition. Bar, 200 μm.

FIG. 3 shows epigenetic properties and cellular dynamics of the PGC-like cells.

FIG. 4 shows a proper spermatogenesis and production of healthy offspring by the ESC-derived PGC-like cells.

FIG. 10 shows the PGC-like cell induction from the epiblasts and EpiLCs.

FIG. 11 shows global transcription profiles during PGC-like cell induction.

FIG. 13 shows induction and purification of PGC-like cells with capacity for spermatogenesis from ESCs with no germ-cell reporters.

DETAILED DESCRIPTION OF THE INVENTION

Figure 1A:
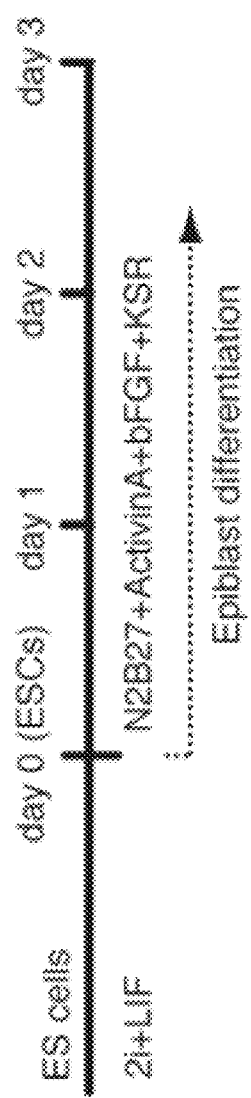
FIG. 1A, The scheme for EpiLC induction.

The present invention provides a method of producing EpiLCs from pluripotent stem cells, which comprises culturing the pluripotent stem cells in the presence of activin A.

The pluripotent stem cell for use as the starting material may be any undifferentiated cell possessing a "self-renewal" that enables it to proliferate while retaining the undifferentiated state, and "pluripotency" that enables it to differentiate into all the three primary germ layers of the embryo. Examples include iPS cells, ES cells, embryonic germ (EG) cells, embryonic cancer (EC) cells and the like, with preference given to iPS cells or ES cells. The method of the present invention is applicable to any mammalian species for which any pluripotent stem cell line has been established or can be established. Examples of such mammals include humans, mice, rats, monkeys, dogs, pigs, bovines, cats, goat, sheep, rabbits, guinea pigs, hamsters and the like, with preference given to humans, mice, rats, monkeys, dogs and the like, more preferably humans or mice.

(1) Preparation of Pluripotent Stem Cells
(i) ES Cells

Pluripotent stem cells can be acquired by methods known per se. For example, available methods of preparing ES cells include, but are not limited to, methods in which a mammalian inner cell mass in the blastocyst stage is cultured [see, for example, Manipulating the Mouse Embryo: A Laboratory Manual, Second Edition, Cold Spring Harbor Laboratory Press (1994)] and methods in which an early embryo prepared by somatic cell nuclear transfer is cultured [Wilmut et al., Nature, 385, 810 (1997); Cibelli et al., Science, 280, 1256 (1998); Iritani et al., Protein, Nucleic Acid and Enzyme, 44, 892 (1999); Baguisi et al., Nature Biotechnology, 17, 456 (1999); Wakayama et al., Nature, 394, 369 (1998); Wakayama et al., Nature Genetics, 22, 127 (1999); Wakayama et al., Proc. Natl. Acad. Sci. USA, 96, 14984 (1999); Rideout III et al., Nature Genetics, 24, 109 (2000)]. Also, ES cells can be obtained from various public and private depositories and are commercially available. For example, human ES cell lines H1 and H9 can be obtained from WiCell Institute of University of Wisconsin and KhES-1, -2 and -3 can be obtained from Institute for Frontier Medical Sciences, Kyoto University. When ES cells are produced by somatic cell nuclear transfer, the kinds and sources of somatic cells are the same as those used for producing iPS cells mentioned below.

(ii) iPS Cells

An iPS cell can be prepared by transferring a nuclear reprogramming substance to a somatic cell.

(a) Sources of Somatic Cells

Any cells other than germ cells of mammalian origin (e.g., mice, humans) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as adipose-derived stromal (stem) cells, nerve stem cells, hematopoietic stem cells, mesenchymal stem cells, and dental pulp stem cells.

The choice of mammal individual as a source of somatic cells is not particularly limited; however, when the PGC-like cells as a final product are to be used for the treatment of diseases such as infertility in humans, it is preferable, from the viewpoint of prevention of graft rejection and/or GvHD, that somatic cells are patient's own cells or collected from another person having the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressor and the like. For example, it includes an HLA type wherein major HLAs (the three major loci of HLA-A, HLA-B and HLA-DR or four loci further including HLA-Cw) are identical (hereinafter the same meaning shall apply) and the like. When the PGC-like cells are not to be administered (transplanted) to a human, but used as, for example, a source of cells for screening for evaluating a patient's drug susceptibility or adverse reactions, it is likewise necessary to collect the somatic cells from the patient or another person with the same genetic polymorphism correlating with the drug susceptibility or adverse reactions.

Somatic cells separated from a mammal can be precultured using a medium known per se suitable for the cultivation thereof, depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium, and the like. When using, for example, a transfection reagent such as a cationic liposome in contacting the cell with nuclear reprogramming substance(s) and iPS cell establishment efficiency improver(s), it is sometimes preferable that the medium be previously replaced with a serum-free medium to prevent a reduction in the transfer efficiency.

(b) Nuclear Reprogramming Substances

In the present invention, "a nuclear reprogramming substance" refers to any substance(s) capable of inducing an iPS cell from a somatic cell, which may be composed of any substance such as a proteinous factor or a nucleic acid that encodes the same (including forms incorporated in a vector), or a low-molecular compound. When the nuclear reprogramming substance is a proteinous factor or a nucleic acid that encodes the same, the following combinations, for example, are preferable (hereinafter, only the names for proteinous factors are shown).

(1) Oct3/4, Klf4, c-Myc
(2) Oct3/4, Klf4, c-Myc, Sox2 (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(3) Oct3/4, Klf4, c-Myc, Sox2, Fbx15, Nanog, Eras, ECAT15-2, Tcl1, β-catenin (active mutant S33Y)
(4) Oct3/4, Klf4, c-Myc, Sox2, TERT, SV40 Large T antigen (hereinafter SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmi1
[For more information on the factors shown above, see WO 2007/069666 (for information on replacement of Sox2 with Sox18 and replacement of Klf4 with Klf1 or Klf5 in the combination (2) above, see *Nature Biotechnology*, 26, 101-106 (2008)); for the combination "Oct3/4, Klf4, c-Myc, Sox2", see also *Cell*, 126, 663-676 (2006), *Cell*, 131, 861-872 (2007) and the like; for the combination "Oct3/4, Klf2 (or Klf5), c-Myc, Sox2", see also *Nat. Cell Biol.*, 11, 197-203 (2009); for the combination "Oct3/4, Klf4, c-Myc, Sox2, hTERT, SV40 LT", see also *Nature*, 451, 141-146 (2008).]

(9) Oct3/4, Klf4, Sox2 (see *Nature Biotechnology*, 26, 101-106 (2008))
(10) Oct3/4, Sox2, Nanog, Lin28 (see *Science*, 318, 1917-1920 (2007))
(11) Oct3/4, Sox2, Nanog, Lin28, hTERT, SV40LT (see *Stem Cells*, 26, 1998-2005 (2008))
(12) Oct3/4, Klf4, c-Myc, Sox2, Nanog, Lin28 (see *Cell Research* (2008) 600-603)
(13) Oct3/4, Klf4, c-Myc, Sox2, SV40LT (see also *Stem Cells*, 26, 1998-2005 (2008))
(14) Oct3/4, Klf4 (see *Nature* 454:646-650 (2008), Cell Stem Cell, 2:525-528 (2008))
(15) Oct3/4, c-Myc (see *Nature* 454:646-650 (2008))
(16) Oct3/4, Sox2 (see *Nature*, 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (Here, Essrrb can be substituted by Esrrg, see *Nat. Cell Biol.*, 11, 197-203 (2009))
(20) Oct3/4, Sox2, Esrrb (see *Nat. Cell Biol.*, 11, 197-203 (2009))
(21) Oct3/4, Klf4, L-Myc
(22) Oct3/4, Nanog
(23) Oct3/4
(24) Oct3/4, Klf4, c-Myc, Sox2, Nanog, Lin28, SV40LT (see *Science*, 324: 797-801 (2009))

In (1)-(24) above, Oct3/4 may be replaced with another member of the Oct family, for example, Oct1A, Oct6 or the like. Sox2 (or Sox1, Sox3, Sox15, Sox17, Sox18) may be replaced with another member of the Sox family, for example, Sox7 or the like. Furthermore, Lin28 may be replaced with another member of the Lin family, for example, Lin28b or the like.

Any combination that does not fall in (1) to (24) above but comprises all the constituents of any one of (1) to (24) above and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the one or more constituents can also be included in the scope of "nuclear reprogramming substances" in the present invention.

Of these combinations, a combination of at least one, preferably two or more, more preferably three or more, selected from among Oct3/4, Sox2, Klf4, c-Myc, Nanog, Lin28 and SV40LT, is a preferable nuclear reprogramming substance.

Particularly, when the iPS cells obtained are to be used for therapeutic purposes, a combination of the three factors Oct3/4, Sox2 and Klf4 [combination (9) above] are preferably used. When the iPS cells obtained are not to be used for therapeutic purposes (e.g., used as an investigational tool for drug discovery screening and the like), the four factors Oct3/4, Sox2, Klf4 and c-Myc, or the five factors Oct3/4, Klf4, c-Myc, Sox2 and Lin28, or the six factors consisting of the five factors and Nanog [combination (12) above], and further, the seven factors consisting of the six factors and SV40 Large T [combination (24) above] are preferable.

Furthermore, the above-described combinations wherein c-Myc is replaced with L-Myc are also preferred as nuclear reprogramming substances.

Information on the mouse and human cDNA sequences of the aforementioned nuclear reprogramming substances is available with reference to the NCBI accession numbers mentioned in WO 2007/069666 (in the publication, Nanog is described as ECAT4. Mouse and human cDNA sequence information on Lin28, Lin28b, Esrrb, Esrrg and L-Myc can be acquired by referring to the following NCBI accession numbers, respectively); those skilled in the art are easily able to isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral vector, plasmid vector, episomal vector etc. to construct an expression vector, and the vector is subjected to the step of nuclear reprogramming.

(c) Method of Transferring a Nuclear Reprogramming Substance to a Somatic Cell

Transfer of a nuclear reprogramming substance to a somatic cell can be achieved using a method known per se for protein transfer into a cell, provided that the substance is a proteinous factor. In view of human clinical applications, it is preferable that the starting material iPS cell be also prepared without gene manipulation.

Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IM-GENEX); those based a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Nuclear reprogramming substance(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, Cell 55, 1189-93 (1988) or Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl. Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. Nature Biotechnol. 19, 1173-6 (2001)), Pep-7 (Gao, C. et al. Bioorg. Med. Chem. 10, 4057-65 (2002)), SynB1 (Rousselle, C. et al. Mol. Pharmacol. 57, 679-86 (2000)), HN-I (Hong, F. D. & Clayman, G L. Cancer Res. 60, 6551-6 (2000)), and HSV-derived VP22. CPPs derived from the PTDs include polyarginines such as 11R (Cell Stem Cell, 4, 381-384 (2009)) and 9R (Cell Stem Cell, 4, 472-476 (2009)).

A fused protein expression vector incorporating cDNA of a nuclear reprogramming substance and PTD or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

However, taking into account the efficiency of establishment of iPS cells, nuclear reprogramming substance may also be used preferably in the form of a nucleic acid that encodes a proteinous factor, rather than the factor as it is. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like.

A vector for this purpose can be chosen as appropriate according to the intended use of the iPS cell to be obtained. Useful vectors include adenovirus vector, plasmid vector, adeno-associated virus vector, retrovirus vector, lentivirus vector, Sendai virus vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

The nucleic acids as nuclear reprogramming substances (reprogramming genes) may be separately integrated into different expression vectors, or 2 kinds or more, preferably 2 to 3 kinds, of genes may be incorporated into a single expression vector. Preference is given to the former case with the use of a retrovirus or lentivirus vector, which offers high gene transfer efficiency, and to the latter case with the use of a plasmid, adenovirus, or episomal vector and the like. Furthermore, an expression vector incorporating two kinds or more of genes and another expression vector incorporating one gene alone can be used in combination.

In the context above, when a plurality of genes are incorporated in one expression vector, these genes can preferably be inserted into the expression vector via an intervening sequence enabling polycistronic expression. By using an intervening sequence enabling polycistronic expression, it is possible to more efficiently express a plurality of genes incorporated in one kind of expression vector. Useful sequences enabling polycistronic expression include, for example, the 2A sequence of foot-and-mouth disease virus (*PLoS ONE* 3, e2532, 2008, *Stem Cells* 25, 1707, 2007), IRES sequence (U.S. Pat. No. 4,937,190) and the like, with preference given to the 2A sequence.

An expression vector harboring a nucleic acid as a nuclear reprogramming substance can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector are disclosed in WO2007/69666, *Cell*, 126, 663-676 (2006) and *Cell*, 131, 861-872 (2007). Specific means using a lentivirus vector is disclosed in *Science*, 318, 1917-1920 (2007). When PGC-like cells induced from iPS cells are utilized for regenerative medicine such as treatment of infertility and gene therapy of germ cells, an expression (reactivation) of a reprogramming gene potentially increases the risk of carcinogenesis in germ cells or reproductive tissues regenerated from PGC-like cells derived from iPS cells; therefore, a nucleic acid encoding a nuclear reprogramming substance is preferably expressed transiently, without being integrated into the chromosome of the cells. From this viewpoint, use of an adenoviral vector, whose integration into chromosome is rare, is preferred. Specific means using an adenoviral vector is disclosed in *Science*, 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.*, 282, 27383-27391 (2007) and JP-3602058 B can be used.

When a retroviral vector or a lentiviral vector is used, even if silencing of the transgene has occurred, it possibly becomes reactivated; therefore, for example, a method can be used preferably wherein a nucleic acid encoding a nuclear reprogramming substance is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivating (SIN) LTR prepared by deleting the sequence, or substituting the sequence with a polyadenylation sequence such as of SV40. Specific means using the Cre-loxP system and SIN LTR is disclosed in Chang et al., *Stem Cells*, 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science*, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferred non-recombination type vector is an episomal vector autonomously replicable outside the chromosome. A specific procedure for using an episomal vector is disclosed by Yu et al. in *Science*, 324, 797-801 (2009). As required, an expression vector may be constructed by inserting a reprogramming gene into an episomal vector having loxP sequences placed in the same orientation at both the 5' and 3' sides of the vector element essential for the replication of the episomal vector, and this may be transferred into a somatic cell.

Examples of the episomal vector include vectors comprising a sequence required for its autonomous replication, derived from EBV, SV40 and the like, as a vector element. Specifically, the vector element required for its autonomous replication is a replication origin or a gene that encodes a protein that binds to the replication origin to regulate its replication; examples include the replication origin oriP and EBNA-1 gene for EBV, and the replication origin on and SV40 large T antigen gene for SV40.

The episomal expression vector contains a promoter that controls the transcription of the reprogramming gene. The promoter used can be the same promoter as the above. The episomal expression vector may further comprise an enhancer, poly-A addition signal, selection marker gene and the like as desired, as described above. Examples of selection marker gene include the dihydrofolate reductase gene, neomycin resistance gene and the like.

An episomal vector can be introduced into a cell using, for example, lipofection method, liposome method, electroporation method, calcium phosphate co-precipitation method, DEAE dextran method, microinjection method, gene gun method and the like. Specifically, the method described in *Science*, 324: 797-801 (2009), for example, can be used.

Whether or not the vector element required for replication of reprogramming gene has been removed from the iPS cell can be determined by performing Southern blot analysis or PCR analysis using a part of the vector as a probe or primer, with an episome fraction isolated from the iPS cell as the template, to examine for the presence or absence of a band or the length of the band detected. An episome fraction can be prepared using a method well known in the art, for example, the method described in *Science*, 324: 797-801 (2009).

When the nuclear reprogramming substance is a low-molecular compound, introduction thereof into a somatic cell can be achieved by dissolving the substance at an appropriate concentration in an aqueous or non-aqueous solvent, adding the solution to a medium suitable for cultivation of somatic cells isolated from human or mouse [e.g., minimal essential medium (MEM) comprising about 5 to 20% fetal bovine serum, Dulbecco's modified Eagle medium (DMEM), RPMI1640 medium, 199 medium, F12 medium, and the like] so that the nuclear reprogramming substance concentration will fall in a range that is sufficient to cause nuclear reprogramming in somatic cells and does not cause cytotoxicity, and culturing the cells for a given period. The nuclear reprogramming substance concentration varies depending on the kind of nuclear reprogramming substance used, and is chosen as appropriate over the range of about 0.1 nM to about 100 nM. Duration of contact is not particularly limited, as far as it is sufficient to cause nuclear reprogramming of the cells; usually, the nuclear reprogramming substance may be allowed to be co-present in the medium until a positive colony emerges.

(d) iPS Cell Establishment Efficiency Improvers

In recent years, various substances that improve the efficiency of establishment of iPS cells, which has traditionally been low, have been proposed one after another. When brought into contact with a somatic cell together with the aforementioned nuclear reprogramming substances, these establishment efficiency improvers are expected to further raise the efficiency of establishment of iPS cells.

Examples of iPS cell establishment efficiency improvers include, but are not limited to, histone deacetylase (HDAC) inhibitors [e.g., valproic acid (VPA) (*Nat. Biotechnol.*, 26(7): 795-797 (2008)], low-molecular inhibitors such as trichostatin sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) [*Nat. Biotechnol.*, 26(7): 795-797 (2008)], G9a histone methyltransferase inhibitors [e.g., low-molecular inhibitors such as BIX-01294 (*Cell Stem Cell*, 2: 525-528 (2008)), nucleic acid-based expression inhibitors such as siRNAs and shRNAs against G9a (e.g., G9a siRNA (human) (Santa Cruz Biotechnology) and the like) and the like], L-channel calcium agonists (e.g., Bayk8644) [*Cell Stem Cell*, 3, 568-574 (2008)], p53 inhibitors [e.g., siRNA and shRNA against p53 (*Cell Stem Cell*, 3, 475-479 (2008)), UTF1 [*Cell Stem Cell*, 3, 475-479 (2008)], Wnt Signaling (e.g., soluble Wnt3a) [*Cell Stem Cell*, 3, 132-135 (2008)], 2i/LIF [2i is an inhibitor of mitogen-activated protein kinase signaling and glycogen synthase kinase-3, *PloS Biology*, 6(10), 2237-2247 (2008)] and the like. As mentioned above, the nucleic acid-based expression inhibitors may be in the form of expression vectors harboring a DNA that encodes an siRNA or shRNA.

Among the constituents of the aforementioned nuclear reprogramming substances, SV40 large T and the like, for example, can also be included in the scope of iPS cell establishment efficiency improvers because they are deemed not essential, but auxiliary, factors for somatic cell nuclear reprogramming. In the situation of the mechanisms for nuclear reprogramming remaining unclear, the auxiliary factors, which are not essential for nuclear reprogramming, may be conveniently considered as nuclear reprogramming substances or iPS cell establishment efficiency improvers. Hence, because the somatic cell nuclear reprogramming process is understood as an overall event resulting from contact of nuclear reprogramming substance(s) and iPS cell establishment efficiency improver(s) with a somatic cell, it seems unnecessary for those skilled in the art to always distinguish between the nuclear reprogramming substance and the iPS cell establishment efficiency improver.

Contact of an iPS cell establishment efficiency improver with a somatic cell can be achieved as described above for each of three cases: (a) the improver is a proteinous factor, (b) the improver is a nucleic acid that encodes the proteinous factor, and (c) the improver is a low-molecular compound.

An iPS cell establishment efficiency improver may be brought into contact with a somatic cell simultaneously with a nuclear reprogramming substance, or either one may be contacted in advance, as far as the efficiency of establishment of iPS cells from the somatic cell is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or plasmid vector, for example, both may be simultaneously introduced into the cell.

(e) Improving the Establishment Efficiency by Culture Conditions

The efficiency of establishment of iPS cells can be further improved by culturing the somatic cells therefor under hypoxic conditions in the step of nuclear reprogramming of the cells. The term hypoxic conditions as used herein means that the oxygen concentration in the ambient atmosphere during cell culture is significantly lower than that in the air. Specifically, such conditions include lower oxygen concentrations than the oxygen concentrations in the ambient atmosphere of 5-10% $CO_2$/95-90% air, which is commonly used for ordinary cell culture; for example, oxygen concentrations of 18% or less in the ambient atmosphere are applicable. Preferably, the oxygen concentration in the ambient atmosphere is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The oxygen concentration in the ambient atmosphere is preferably 0.1% or more (e.g., 0.2% or more, 0.3% or more, 0.4% or more and the like), 0.5% or more (e.g., 0.6% or more, 0.7% or more, 0.8% or more, 0.9% or more and the like), or 1% or more (e.g., 1.1% or more, 1.2% or more, 1.3% or more, 1.4% or more and the like).

There is no limitation on how to create hypoxic conditions in a cellular environment; the easiest of suitable methods is to culture cells in a $CO_2$ incubator that allows control of oxygen concentrations. Such $CO_2$ incubators are commercially available from a number of manufacturers of equipment (e.g., $CO_2$ incubators for hypoxic culture manufactured by Thermo Scientific, Ikemoto Scientific Technology, Juji Field Inc., and Wakenyaku Co., Ltd. can be used).

The timing of beginning cell culture under hypoxic conditions is not particularly limited, as far as it does not interfere with improving the efficiency of establishment of iPS cells compared with that obtained at a normal oxygen concentration (20%). The starting time may be before or after contact of nuclear reprogramming substances with a somatic cell, and may be at the same time as the contact. For example, it is preferable that cell culture under hypoxic conditions be begun just after contacting a nuclear reprogramming substance with a somatic cell, or after a given time (e.g., 1 to 10 (e.g., 2, 3, 4, 5, 6, 7, 8 or 9) days) following the contact.

The duration of cell culture under hypoxic conditions is not particularly limited, as far as it does not interfere with improving the efficiency of establishment of iPS cells compared with that obtained at a normal oxygen concentration (20%); examples include, but are not limited to, between 3 days or more, 5 days or more, 7 days or more or 10 days or more, and 50 days or less, 40 days or less, 35 days or less or 30 days or less. The preferred duration of cell culture under hypoxic conditions also varies depending on the oxygen concentration in the ambient atmosphere; those skilled in the art can adjust as appropriate the duration of cell culture according to the oxygen concentration used. In an embodiment of the present invention, when iPS cell candidate colonies are selected with drug resistance as an indicator, it is preferable that a normal oxygen concentration be restored from hypoxic conditions by the start of drug selection.

Furthermore, the preferred starting time and duration of cell culture under hypoxic conditions also vary depending on the choice of nuclear reprogramming substances used, the efficiency of establishment of iPS cells under conditions involving a normal oxygen concentration, and other factors.

After the nuclear reprogramming substance(s) (and iPS cell establishment efficiency improver(s)) is(are) brought into contact with the cell, the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts (MEFs) treated with radiation or an antibiotic to terminate the cell division thereof, as feeder cells. Usually, STO cells and the like are commonly used as MEFs, but for inducing iPS cells, SNL cells [McMahon, A. P. & Bradley, A. *Cell* 62, 1073-1085 (1990)] and the like are commonly used. Co-culture with feeder cells may be started before contact of the nuclear reprogramming substance, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs from a mouse having the βgeo (which encodes a fusion protein of β-galactosidase and neomycin phosphotransferase) gene knocked-in to the Fbx15 locus [Takahashi & Yamanaka, *Cell*, 126, 663-676 (2006)], MEFs from a transgenic mouse having the green fluorescent protein (GFP) gene and the puromycin resistance gene integrated in the Nanog locus [Okita et al., *Nature*, 448, 313-317 (2007)] and the like. Meanwhile, examples of the method of selecting candidate colonies based on visual examination of morphology include the method described by Takahashi et al. in *Cell*, 131, 861-872 (2007). Although the method using reporter cells is convenient and efficient, it is desirable from the viewpoint of safety that colonies be selected by visual examination when iPS cells are prepared for the purpose of human treatment. When the three factors Oct3/4, Klf4 and Sox2 are used as nuclear reprogramming substances, the number of clones established decreases but the resulting colonies are mostly of iPS cells of high quality comparable to ES cells, so that iPS cells can efficiently be established even without using reporter cells.

The identity of the cells of a selected colony as iPS cells can be confirmed by positive responses to a Nanog (or Oct3/4) reporter (puromycin resistance, GFP positivity and the like) as well as by the formation of a visible ES cell-like colony, as described above. However, to ensure higher accuracy, it is possible to perform tests such as analyzing the expression of various ES-cell-specific genes and transplanting the cells selected to a mouse and confirming the formation of teratomas.

(iii) Naive Human ES and iPS Cells

Conventional human ES cells derived from blastocyst-stage embryos have very different biological (morphological, molecular and functional) properties from mouse ES cells. Mouse pluripotent stem cells can exit in two functionally distinct states, LIF-dependent ES cells and bFGF-dependent epiblast stem cells (EpiSCs). Molecular analyses suggest that the pluripotent state of human ES cells is similar to that of mouse EPiSCs rather than that of mouse ES cells. Recently, human ES and iPS cells in a mouse ES cell-like pluripotent state (also referred to as naive human ES and iPS cells) have been established by ectopic induction of Oct3/4, Sox2, Klf4, c-Myc and Nanog in the presence of LIF (see *Cell Stem Cells*, 6: 535-546, 2010), or ectopic induction of Oct3/4, Klf4 and Klf2 combined with LIF and inhibitors of GSK3β and ERK1/2 pathway (see *Proc. Natl. Acad. Sci. USA*, online publication doi/10.1073/pnas.1004584107). These naive human ES and iPS cells may be preferable starting materials for the present invention due to their pluripotent more immature compared to that of conventional human ES and iPS cells.

(2) Induction of Differentiation from Pluripotent Stem Cells to EpiLCs

Basal media for differentiation induction include, but are not limited to, Neurobasal medium, Neural Progenitor Basal medium, NS-A medium, BME medium, BGJb medium, CMRL 1066 medium, minimal essential medium (MEM), Eagle MEM, αMEM, Dulbecco's modified Eagle medium (DMEM), Glasgow MEM, Improved MEM Zinc Option medium, IMDM medium, 199 medium, DMEM/F12 medium, Ham's medium, RPMI1640 medium, Fischer's medium, and mixtures thereof.

The medium can be a serum-containing or serum-free medium. Preferably, a serum-free medium can be used. The serum-free medium (SFM) refers to media with no unprocessed or unpurified serum and accordingly, can include media with purified blood-derived components or animal tissue-derived components (such as growth factors). The concentration of serum (for example, fetal bovine serum (FBS), human serum, etc.) can be 0-20%, preferably 0-5%, more preferably 0-2%, most preferably 0% (i.e., serum-free). The SFM may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3' thiolglycerol, or equivalents thereto. The alternatives to serum can be prepared by the method disclosed in WO 98/30679, for example. Alternatively, any commercially available materials can be used for more convenience. The commercially available materials include Knockout™ Serum Replacement (KSR), Chemically-defined Lipid concentrated, and Glutamax (Invitrogen).

The medium can also contain other additives known per se. The additive is not subject to limitation, as long as EpiLCs equivalent to pre-gastrulating epiblast cells can be produced by the method of the present invention; for example, growth factors (for example, insulin and the like), polyamines (for example, putrescine and the like), minerals (for example, sodium selenate and the like), saccharides (for example, glucose and the like), organic acids (for example, pyruvic acid, lactic acid and the like), amino acids (for example, non-essential amino acids (NEAA), L-glutamine and the like), reducing agents (for example, 2-mercaptoethanol and the like), vitamins (for example, ascorbic acid, d-biotin and the like), steroids (for example, [beta]-estradiol, progesterone and the like), antibiotics (for example, streptomycin, penicillin, gentamycin and the like), buffering agents (for example, HEPES and the like), nutritive additives (for example, B27 supplement, N2 supplement, StemPro-Nutrient Supplement and the like) and the like can be mentioned. It is preferable that each of the additives be contained in a concentration range known per se.

In the method of producing EpiLCs of the present invention, pluripotent stem cells may be cultured in the presence or absence of feeder cells. The feeder cells are not subject to limitation, as long as EpiLCs can be produced by the method of the present invention; feeder cells known per se for use in culturing pluripotent stem cells such as ESCs and iPSCs can be used; for example, fibroblasts (mouse embryonic fibroblasts, mouse fibroblast cell line STO and the like) can be mentioned. The feeder cells are preferably inactivated by a method known per se, for example, radiation (gamma rays and the like), treatment with an anticancer agent (mitomycin C and the like) and the like. However, in a preferable embodiment of the present invention, pluripotent stem cells are cultured under feeder-free conditions.

The medium for inducing differentiation from pluripotent stem cells to EpiLCs (medium A) contains activin A as an essential additive in the basal medium. The activin A concentration is, for example, about 5 ng/ml or more, preferably about 10 ng/ml or more, more preferably about 15 ng/ml or more, and is, for example, about 40 ng/ml or less, preferably about 30 ng/ml or less, more preferably 25 ng/ml or less.

The medium A preferably further contains bFGF and/or KSR. Basic FGF and KSR remarkably increase the induction efficiency for EpiLCs when present in a range of effective concentrations. The bFGF concentration is, for example, about 5 ng/ml or more, preferably about 7.5 ng/ml or more, more preferably about 10 ng/ml or more, and is, for example, about 30 ng/ml or less, preferably about 20 ng/ml or less, more preferably about 15 ng/ml or less. The KSR concentration is, for example, about 0.1 w/w % or more, preferably about 0.3 w/w % or more, more preferably about 0.5 w/w % or more, and is, for example, about 5 w/w % or less, preferably about 3 w/w % or less, more preferably about 2 w/w % or less.

In a particularly preferred embodiment, the medium A contains activin A, bFGF and KSR in addition to the basal medium. Appropriate concentrations of these ingredients can be chosen over the range of about 10-30 ng/ml, preferably 15-25 ng/ml for activin A, about 7.5-20 ng/ml, preferably about 10-15 ng/ml for bFGF, and about 0.3-3 w/w %, preferably about 0.5-2 w/w % for KSR.

The activin A and bFGF contained in the medium A are not subject to limitation as to the source thereof, may be isolated and purified from cells of any mammals (for example, human, mouse, monkey, swine, rat, dog and the like). It is preferable to use activin A and bFGF homologous to the pluripotent stem cells subjected to the culture. The activin A and bFGF may also be chemically synthesized or biochemically synthesized using a cell-free translation system, or produced from a transformant bearing a nucleic acid encoding each of the proteins. The recombinant products of activin A and bFGF are commercially available.

A culture vessel used for inducing pluripotent stem cells into EpiLCs can include, but is particularly not limited to, flask, flask for tissue culture, dish, petri dish, dish for tissue culture, multi dish, micro plate, micro-well plate, multi plate, multi-well plate, micro slide, chamber slide, schale, tube, tray, culture bag, and roller bottle. The culture vessel can be cellular adhesive. The cellular adhesive culture vessel can be coated with any of substrates for cell adhesion such as extracellular matrix (ECM) to improve the adhesiveness of the vessel surface to the cells. The substrate for cell adhesion can be any material intended to attach pluripotent stem cells or feeder cells (if used). The substrate for cell adhesion includes collagen, gelatin, poly-L-lysine, poly-D-lysine, poly-L-ornithine, laminin, and fibronectin and mixtures thereof for example Matrigel, and lysed cell membrane preparations (Klimanskaya I et al 2005. *Lancet* 365: p1636-1641).

In this cultivation, pluripotent stem cells are plated onto the culture vessel mentioned above to obtain a cell density of, for example, about $10^4$-$10^5$ cells/cm$^2$, preferably about 2 to $8\times10^4$ cells/cm$^2$, and cultured in an incubator under atmospheric conditions of 1-10% $CO_2$/99-90% air at about 30-40° C., preferably about 37° C., for less than 3 days, preferably about 2 days (e.g., 48±12 hours, preferably 48±6 hours). As a result of the culture, cells with flattened epiblast-like structure uniformly emerged.

The fact of differentiation into EpiLCs can be confirmed by, for example, analyzing the expression levels of EPiLC- and/or pluripotent stem cell-marker genes using RT-PCR. The EpiLC of the present invention means a cell in E5.5-E6.0 epiblast-like (pre-gastrulating epiblast-like) state. To be specific, the EpiLC is defined as a cell having either or both of the following properties:
(1) elevated gene expression of at least one selected from Fgf5, Wnt3 and Dnmt3b compared to the pluripotent stem cell before inducing differentiation;

(2) reduced gene expression of at least one selected from Gata4, Gata6, Sox17 and Blimp1 compared to the pluripotent stem cell before inducing differentiation. Therefore, the fact of differentiation into EpiLCs can be confirmed by determining the expression levels of at least one selected from Fgf5, Wnt3 and Dnmt3b and/or at least one selected from Gata4, Gata6, Sox17 and Blimp1 in the cells obtained by the culture, and comparing the expression levels with those in the pluripotent stem cells before inducing differentiation.

More preferably, the EpiLC of the present invention has the following properties:
(1) continuous gene expression of Oct3/4;
(2) reduced gene expression of Sox2 and Nanog compared to the pluripotent stem cell before inducing differentiation;
(3) elevated gene expression of Fgf5, Wnt3 and Dnmt3b compared to the pluripotent stem cell before inducing differentiation; and
(4) reduced gene expression of Gata4, Gata6, Sox17 and Blimp1 compared to the pluripotent stem cell before inducing differentiation.

As mentioned above, in a preferable embodiment, the medium A of the present invention contains activin A, bFGF and KSR. Accordingly, the present invention also provides a reagent kit for inducing the differentiation from pluripotent stem cells to EpiLCs comprising activin A, bFGF and KSR. These ingredients may be supplied in a state dissolved in water or an appropriate buffer solution, and may also be supplied as a lyophilized powder which may be used after being freshly dissolved in an appropriate solvent. These ingredients may be supplied as individual reagents in respective kits, and, as far as they do not adversely affect each other, they can be supplied as a single mixed reagent of 2 kinds or more.

The present inventors succeeded, albeit transiently, in the production of EpiLCs having properties equivalent to pre-gastrulating epiblast cells for the first time. Since epiblasts are also progenitors of somatic cell lineages other than germ cell lineage, thus-obtained EpiLCs can be used as a starting cell material for inducing not only germ cell lineage but also other various cell lineages. They would also be useful for the investigation of the genetic and epigenetic mechanism underlying the ICM to epiblast differentiation, which is a critical but less understood subject in pluripotent cell biology. Derivation of EpiLCs from ESCs or iPSCs as an intermediate for specific lineages is a very straightforward process, and provides a novel strategy for in vitro reconstruction of lineage specification.

(3) Induction of Differentiation from EpiLCs to PGC-Like Cells

By culturing thus-obtained EpiLCs in the presence of BMP4 and LIF, it is possible to induce differentiation into PGC-like cells (*Cell*, 137, 571-584 (2009)). Accordingly, a second aspect of the present invention relates to a method of producing PGC-like cells from pluripotent stem cells through EpiLCs obtained by the method of (2) above. Namely, the method comprises:
I) the step for producing an EpiLC from pluripotent stem cells according to any of the methods described in (2) above; and
II) the step for culturing the EpiLC obtained in the step I) in the presence of BMP4 and LIF.

As the basal medium for differentiation induction in the step II), the basal media exemplified for the use in the step I) are likewise preferably used. The medium may contain the same additives as those exemplified for the use in the step I), as long as PGC-like cells capable of contributing to normal spermatogenesis can be produced by the method of the present invention.

The medium can be a serum-containing or serum-free medium (SFM). Preferably, a serum-free medium can be used. The concentration of serum (for example, fetal bovine serum (FBS), human serum, etc.) can be 0-20%, preferably 0-5%, more preferably 0-2%, most preferably 0% (i.e., serum-free). The SFM may contain or may not contain any alternatives to serum such as KSR.

The medium for inducing differentiation from EpiLCs to PGC-like cells (medium B) contains bone morphogenetic protein 4 (BMP4) and leukemia inhibitory factor (LIF) as an essential additive in the basal medium. The concentration of BMP4 is, for example, about 100 ng/ml or more, preferably about 200 ng/ml or more, more preferably about 300 ng/ml or more. Also, the concentration of BMP4 is, for example, about 1,000 ng/ml or less, preferably about 800 ng/ml or less, more preferably 600 ng/ml or less. The concentration of LIF is, for example, about 300 U/ml or more, preferably about 500 U/ml or more, more preferably about 800 U/ml or more. Also, the concentration of LIF is, for example, about 2,000 U/ml or less, preferably about 1,500 U/ml or less, more preferably 1,200 U/ml or less.

The medium B preferably further contains at least one additive(s) selected from stem cell factor (SCF), bone morphogenetic protein 8b (BMP8b) and epidermal growth factor (EGF). SCF, BMP8b and EGF remarkably prolong the period of time which PGC-like cells are maintained in a Blimp1- and Stella-positive state, when present in ranges of effective concentrations. The concentration of SCF is, for example, about 30 ng/ml or more, preferably about 50 ng/ml or more, more preferably about 80 ng/ml or more. Also, the concentration of SCF is, for example, about 200 ng/ml or less, preferably about 150 ng/ml or less, more preferably about 120 ng/ml or less. The concentration of BMP8b is, for example, about 100 ng/ml or more, preferably about 200 ng/ml or more, more preferably about 300 ng/ml or more. Also, the concentration of BMP8b is, for example, about 1,000 ng/ml or less, preferably about 800 ng/ml or less, more preferably 600 ng/ml or less. The concentration of EGF is, for example, about 10 ng/ml or more, preferably about 20 ng/ml or more, more preferably about 30 ng/ml or more. Also, the concentration of EGF is, for example, about 100 ng/ml or less, preferably about 80 ng/ml or less, more preferably about 60 ng/ml.

In a particularly preferred embodiment, the medium B contains BMP, LIF, SCF, BMP8b and EGF in addition to the basal medium. The concentrations of these ingredients can be chosen as appropriate over the ranges of about 200-800 ng/ml, preferably about 300-600 ng/ml for BMP4, about 500-1500 U/ml, preferably about 800-1,200 U/ml for LIF, about 50-150 ng/ml, preferably about 80-120 ng/ml for SCF, about 200-800 ng/ml, preferably about 300-600 ng/ml for BMP8b, and about 20-80 ng/ml, preferably about 30-60 ng/ml for EGF.

The BMP4, LIF, SCF, BMP8b and EGF contained in the medium B are not subject to limitation as to the source thereof, may be isolated and purified from cells of any mammals (for example, human, mouse, monkey, swine, rat, dog and the like). It is preferable to use BMP4, LIF, SCF, BMP8b and EGF homologous to the EpiLCs subjected to the culture. The BMP4, LIF, SCF, BMP8b and EGF may also be chemically synthesized or biochemically synthesized using a cell-free translation system, or produced from a transformant bearing a nucleic acid encoding each of the proteins. The recombinant products of BMP4, LIF, SCF, BMP8b and EGF are commercially available.

In this cultivation, EpiLCs are seeded to a cellular non-adhesive or low-adhesive culture vessel known per se to obtain a cell density of, for example, about 3 to $10 \times 10^4$ cells/mL, preferably about 4 to $8 \times 10^4$ cells/mL, and cultured in an incubator in an atmosphere of 1-10% $CO_2$/99-90% air at about 30-40° C., preferably about 37° C., for about 4-10 days, preferably 4-8 days, more preferably about 6 days (e.g., 144±12 hours, preferably 144±6 hours).

The fact of differentiation into PGC-like cells can be confirmed by, for example, analyzing the expression of Blimp1 by RT-PCR and the like. As required, furthermore, the expression of other genes and cell surface antigens can also be examined. Examples of other genes include Stella. When pluripotent stem cells bearing fluorescent protein genes under the control of Blimp1- and/or Stella-promoters are used as a starting material, the fact of differentiation into PGC-like cells can be confirmed by FACS analysis. When the pluripotent stem cells bear no appropriate transgenic reporter, such as ESCs or iPSCs derived from human or other non-mouse mammals, it is preferable to confirm the fact of differentiation into PGC-like cells by FACS analysis and the like using one or more cell surface antigens specifically expressed on PGC-like cells. As the cell surface antigens, preferably SSEA-1 and integrin-β3 are exemplified.

As mentioned above, in a preferable embodiment, the medium B of the present invention contains BMP4, LIF, SCF, BMP8b and EGF. Accordingly, the present invention also provides a reagent kit for inducing the differentiation from EpiLCs to PGC-like cells comprising BMP4, LIF, SCF, BMP8b and EGF. These ingredients may be supplied in a state dissolved in water or an appropriate buffer solution, and may also be supplied as a lyophilized powder which may be used after being freshly dissolved in an appropriate solvent. These ingredients may be supplied as individual reagents in respective kits, and, as far as they do not adversely affect each other, they can be supplied as a single mixed reagent of 2 kinds or more.

(4) Cell Population Containing PGC-Like Cells Derived from Pluripotent Stem Cells Through EpiLCs The present invention also provides a cell population containing PGC-like cells derived from pluripotent stem cells, produced by the foregoing steps I) and II). The cell population may be a purified population of PGC-like cells, and 1 kind or more of cells other than PGC-like cells may be co-present. Here, "PGC-like cell" is defined as a cell that shows elevated expression of Blimp1 and/or Stella compared to the EpiLC before inducing differentiation, is capable of contributing to normal spermatogenesis, and does not form teratoma when transplanted into an immunodeficient mouse. As stated above, when PGC-like cells are induced using pluripotent stem cells bearing fluorescent protein genes under the control of Blimp1- and/or Stella-promoters as a starting material, the Blimp1- and/or Stella-positive PGC-like cells can be easily isolated and purified by sorting out the cell population obtained in the foregoing step II) using a cell sorter. The PGC-like cells can also be isolated and purified by FACS using a reporter under the control of gene whose expression increases along with Blimp1 and Stella (e.g., Nanog) as a marker.

Preferably, the cell population containing PGC-like cells of the present invention is a cell population derived from iPSCs or ESCs. When the iPSCs have been produced by, for example, transferring reprogramming gene(s) to somatic cells by means of a retroviral vector or lentiviral vector, the reprogramming gene(s) are integrated in the genome of the cells; therefore, the PGC-like cells derived from the iPSCs also have the reprogramming gene(s) integrated in the genome thereof. Because the PGC-like cells derived from iPSCs have been established for the first time by the present invention, the PGC-like cells having exogenous reprogramming gene(s) integrated in the genome thereof are of course novel cells. A reprogramming gene to be integrated in the genome of PGC-like cells is a nucleic acid that encodes one of the nuclear reprogramming substances described above with respect to preparing iPSCs, preferably 3 genes consisting of Oct3/4, Sox2, and Klf4, or 4 genes consisting of the foregoing three and c-Myc.

(5) Use of PGC-Like Cells Derived from Pluripotent Stem Cells

The PGC-like cells derived from pluripotent stem cells thus established can be used for varied purposes. For example, since the PGC-like cells transplanted into a testis of a recipient animal can robustly contribute to spermatogenesis in the testis and the generation of healthy offspring, they can be used for the treatment of infertility or hereditary diseases of reproductive tissues.

The transplantation of the PGC-like cells into a testis can be performed by using the PGC-like cells in place of germline stem cells (GS cells) in the methods disclosed in WO 2004/092357 and *Biol. Reprod.*, 69: 612-616 (2003). Alternatively, the PGC-like cells can be cultured in the same manner as WO 2004/092357 and *Biol. Reprod.* (2003), supra to induce differentiation into GS cells, then transplanted into a testis.

The PGC-like cells (including a cell population containing PGC-like cells; the same applies below) of the present invention are produced as a parenteral preparation, preferably as an injection, suspension, or drip infusion, in a mixture with a pharmaceutically acceptable carrier, by a conventional means. Examples of the pharmaceutically acceptable carrier that can be contained in the parenteral preparation include aqueous liquids for injection, such as physiological saline and isotonic solutions containing glucose and other auxiliary drugs (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an anti-oxidant and the like.

When the agent of the present invention is prepared as an aqueous suspension, PGC-like cells are suspended in one of the aforementioned aqueous liquids to obtain a cell density of about $1.0 \times 10^6$ to about $1.0 \times 10^7$ cells/ml.

The agent of the present invention can be cryopreserved under conditions typically used for the cryopreservation of stem cells, and thawed immediately before use.

Because the preparation thus obtained is stable and less toxic, it can be safely administered to mammals such as humans. Although the method of administration is not particularly limited, the preparation is preferably administered by injection or drip infusion into a seminiferous tubule. For a male infertility patient, for example, it is usually convenient to administer the agent in an amount of about $1.0 \times 10^5$ to about $1 \times 10^7$ cells, based on the amount of PGC-like cells per dose, once or 2-10 times at about 1- to 2-week intervals.

The present invention is the first demonstration of an in vitro reconstruction of germ-cell specification pathway from inner cell mass (ICM). Such in vitro system reflecting the developmental processes will promote not only the elucidation of detailed developmental mechanisms of germ cells but also the elucidation of mechanisms of infertility and development of hereditary diseases.

The present invention is hereinafter described in further detail by means of the following examples, to which, however, the invention is never limited.

EXAMPLES

Methods Summary

The BVSC and P14V transgenic mice were reported previously and maintained on a largely C57BL/6 background (*Nat Genet.* 40, 1016-1022 (2008); *Reproduction* 136, 503-514 (2008)). All the animal experiments were performed under the ethical guidelines of Kyoto University.

The ESCs were derived in N2B27 medium (a 1:1 mixture of DMEM/F12 supplemented with N2 and Neurobasal supplemented with B27) (*Nat Biotechnol* 21, 183-186, doi: 10.1038/nbt780) with 2i and LIF on mouse embryonic feeder cells (*Nature* 453, 519-523, doi:nature06968 [pii] 10.1038/nature06968 (2008)). After passage 4, male ESCs were maintained without feeders on a dish coated with poly-L-ornithine (0.01%; Sigma) and Laminin (10 ng/ml, BD Biosciences). The EpiLCs were induced from the ESCs by activin A (20 ng/ml; Peprotech), bFGF (12 ng/ml; Invitrogen), and KSR (1%; Invitrogen) in N2B27 medium in a dish coated with human plasma fibronectin (16.7 µg/ml.; Millipore). The PGC-like cells were induced from the EpiLCs with BMP4 (500 ng/ml; R&D Systems), LIF (1000 U/ml; Invitrogen), SCF (100 ng/ml; R&D Systems), BMP8b (500 ng/ml; R&D Systems), and EGF (50 ng/ml; R&D Systems) in the SFM [GMEM (Invitrogen) with 15% KSR, 0.1 mM NEAA, 1 mM sodium pyruvate, 0.1 mM 2-mercaptoethanol, 100 U/ml penicillin, 0.1 mg/ml streptomycin, and 2 mM L-glutamine] (*Cell* 137, 571-584 (2009)) in a floating condition in a low-cell-binding U-bottom 96-well plate (NUNC) (a 1,000-cell aggregate per well). The images were taken by a SZX16 fluorescent dissection microscope equipped with a DP72 camera (Olympus) or an Axiovert200 inverted fluorescent microscope equipped with an Axio-CamMRm camera (Zeiss).

The primer sequences for quantitative (Q)-PCR (*Genes Dev* 22, 1617-1635 (2008); *Biol Reprod* 75, 705-716 (2006)), for the bisulfite analysis (*Anal Biochem* 226, 161-166, doi:S0003-2697(85)71204-3 [pii] 10.1006/abio.1995.1204 (1995); *Genomics* 79, 530-538 (2002); *Nature* 450, 908-912 (2007)), and for the genotyping of BVSC transgenes (*Reproduction* 136, 503-514 (2008)) are listed in Table 1.

TABLE 1

Primer sequences used for this study.

| | Forward (SEQ ID NO:) | Reverse (SEQ ID NO:) |
|---|---|---|
| Q-PCR | | |
| Pou5f1 | GATGCTGTGAGCCAAGGCAAG (1) | GGCTCCTGATCAACAGCATCAC (2) |
| Sox2 | CATGAGAGCAAGTACTGGCAAG (3) | CCAACGATATCAACCTGCATGG (4) |
| Nanog | CTTTCACCTATTAAGGTGCTTGC (5) | TGGCATCGGTTCATCATGGTAC (6) |
| Blimp1 | AGCATGACCTGACATTGACACC (7) | CTCAACACTCTCATGTAAGAGGC (8) |
| Prdm14 | ACAGCCAAGCAATTGCACTAC (9) | TTACCTGGCATTTTCATTGCTC (10) |
| Tcfap2c | GGGCTTTTCTCTCTTGGCTGGT (11) | TCCACACGTCACCCACACAA (12) |
| Nanos3 | CACTACGGCCTAGGAGCTTGG (13) | TGATCGCTGACAAGACTGTGG (14) |
| Dppa3 | AGGCTCGAAGGAAATGAGTTTG (15) | TCCTAATTCTTCCCGATTTTCG (16) |
| Tdrd5 | GGGCAGCCTCAAAAGCACTC (17) | CGTGGCTTCAGCACGGCTAT (18) |
| Dnd1 | CCCTAAATGGGTTAAGCAGAGC (19) | GGCAAGGTTCCTCACAACTAAAG (20) |
| Hoxb1 | GATCCTACAGGTCTTGGGACC (21) | AGCTCAAAGGCACTGAACTGAG (22) |
| Hoxa1 | GTGACTAGTCTTCTGCATGTCG (23) | TCTGCTCTGGACCACATCACTC (24) |
| Snai1 | AGCAGGGTGGTTACTGGACAC (25) | CCATTATTCATGGTCCCTTCTG (26) |
| Dnmt1 | AAAGAGGAGGCTGCTACCAAG (27) | CCACAGACACTGAGCACAAGAC (28) |
| Np95 | GTTACAGCCTGTACTGAGGAAG (29) | TAGAACTGTGCTGTCCAGTCTG (30) |
| Dnmt3a | GACTCGCGTGCAATAACCTTAG (31) | GGTCACTTTCCCTCACTCTGG (32) |
| Dnmt3b | CTCGCAAGGIGTGGGCTTTTGTAAC (33) | CTGGGCATCTGTCATCTTTGCACC (34) |
| c-Myc | AAGGAGAACGGTTCCTTCTGAC (35) | GCTGAAGCTTACAGTCCCAAAG (36) |
| Mvh | TATGTGCCTCCCAGCTTCAGTA (37) | CTGGATTGGGAGCTTGTGAAGA (38) |
| Daz1 | TCCTTGACTTGTGGTTGCTG (39) | CCACCTTCGAGGTTTTACCA (40) |
| Zfp42 | TCCATGGCATAGTTCCAACAG (41) | TAACTGATTTTCTGCCGTATGC (42) |

TABLE 1-continued

Primer sequences used for this study.

| | Forward (SEQ ID NO:) | Reverse (SEQ ID NO:) |
|---|---|---|
| Tbx3 | TTATTTCCAGGTCAGGAGATGGC (43) | GGTCGTTTGAACCAAGTCCCTC (44) |
| Tcl1 | TGGCCTCACTAGAACAAGAGG (45) | CTCGGTCAAGGATGGAAGC (46) |
| Esrrb | CAGGCAAGGATGACAGACG (47) | GAGACAGCACGAAGGACTGC (48) |
| Klf2 | TCGAGGCTAGATGCCTTGTGA (49) | AAACGAAGCAGGCGGCAGA (50) |
| Klf4 | TGGTGCTTGGTGAGTTGTGG (51) | GCTCCCCCGTTTGGTACCTT (52) |
| Klf5 | TACGGGCGAGAAGCCCTACA (53) | GGCACACCATGCACTGGAAC (54) |
| Fgf5 | AAAGTCAATGGCTCCCACGAA (55) | CTTCAGTCTGTACTTCACT (56) |
| Wnt3 | CAAGCACAACAATGAAGGAGGC (57) | TCGGGACTCACGGTGTTTCTC (58) |
| T | ATCAGAGTCCTTTGCTAGGTAG (59) | GTTACAATCTTCTGGCTATGC (60) |
| Gata4 | TTCCTCTCCCAGGAACATCAAA (61) | GCTGCACAACTGGGCTCTACTT (62) |
| Gata6 | TGCAAGATTGCATCATGACAGA (63) | TGACCTCAGATCAGCCACGTTA (64) |
| Sox17 | TTCTGTACACTTTAATGAGGCTGTTC (65) | TTGTGGGAAGTGGGATCAAG (66) |
| Arbp | CAAAGCTGAAGCAAAGGAAGAG (67) | AATTAAGCAGGCTGACTTGGTTG (68) |
| Ppia | TTACCCATCAAACCATTCCTTCTG (69) | AACCCAAAGAACTTCAGTGAGAGC (70) |
| Bisulfite | | |
| Igf2r | TTAGTGGGGTATTTTATTTGTATGG (71) | AAATATCCTAAAAATACAAACTACAC (72) |
| Igf2r nest* | GTGTGGTATTTTTATGTATAGTTAGG (73) | |
| H19 | GAGTATTTAGGAGGTATAAGAATT (74) | ATCAAAAACTAACATAAACCCCT (75) |
| H19 nest | GTAAGGAGATTATGTTTATTTTGG (76) | CCTCATTAATCCCATAACTAT (77) |
| Snrpn | TATGTAATATGATATAGTTTAGAAATTAG (78) | AATAAACCCAAATCTAAAATATTTTAATC (79) |
| Snrpn nest | AATTTGTGTGATGTTTGTAATTATTTGG (80) | ATAAAATACACTTTCACTACTAAAATCC (81) |
| Kcnq1ot1 | ATTTTTGTGGTTTAGGTTTATAGAAGTAGGG (82) | TTAAAAATCACCACAACATAAATAACTATAT (83) |
| Kcnq1ot1 nest | TAGAAGTAGGGGTGGTTTTGAGGTTTTTG (84) | CCACAACATAAATAACTATATTAAAAAATCA (85) |
| Genotyping | | |
| Blimp1-mVenus | ACTCATCTCAGAAGAGGATCTG (86) | CACAGTCGAGGCTGATCTCG (87) |
| stella-ECFP | CGAGCTAGGTTTTGAGGCTT (88) | AACTTGTGGCCGTTTACGTC (89) |
| Nanog-EGFP | GACGTAAACGGCCACAAGTTC (90) | AAGTCGTGCTGCTTCATGTG (91) |
| Oct4 (Tg) | CTGAGGGCCAGGCAGGAGCACGAG (92) | CTGTAGGGAGGGCTTCGGGCACTT (93) |

*Nested PCR for Igf2r was performed using the Igf2r nest forward primer and the reverse primer identical to that used in the first round PCR reaction for Igf2r.

The primary antibodies used for immunohistochemistry (*Reproduction* 139, 381-393, doi:REP-09-0373 [pii] 10.1530/REP-09-0373 (2010)) were as follows: anti-Oct3/4 (mouse monoclonal; BD Biosciences), anti-Sox2 (rabbit polyclonal; Santa Cruz), anti-Nanog (rat monoclonal; eBioscience), anti-H3K9me2 (rabbit polyclonal; Upstate), anti-H3H27me3 (rabbit polyclonal; Upstate), and anti-Dnmt3b (mouse monoclonal; Abcam). The secondary antibodies were as follows: Alexa Fluor 488 anti-rabbit IgG, Alexa Fluor 568 anti-rabbit, or -rat, or -mouse IgG, Alexa Fluor 633 anti-mouse IgG (all of these are goat polyclonal; Invitrogen). Immunofluorescence images were taken by a confocal microscope (Olympus FV1000). Fluorescence-activated cell sorting (FACS) was performed using an ARIA II cell sorter (BD Biosciences).

Transplantation of the PGC-like cells into the seminiferous tubules of neonatal W/W$^v$ mice (SLC) and the intra-cytoplasmic sperm injection (ICSI) were performed as described previously (*Int J Dev Biol* 41, 111-122 (1997); *Biol Reprod* 52, 709-720 (1995)).

Methods

1. Animals

All the animal experiments were performed under the ethical guidelines of Kyoto University. The BVSC and P14V transgenic mice were reported previously (*Nat Genet.* 40, 1016-1022 (2008); *Reproduction* 136, 503-514 (2008)) and maintained on a largely C57BL/6 background. The ROSA mice [B6; 129S-Gt(ROSA)26Sor/J (stock number:002073)] (*Genes Dev* 5, 1513-1523 (1991)) were purchased from the Jackson Laboratory. The W/W$^v$ mice (WB×C57BL/6) were purchased from SLC (Shizuoka, Japan). Noon of the day when a copulation plug was identified was designated as embryonic day (E) 0.5.

2. ESC/EpiSC Derivation and Culture

The blastocysts bearing the BVSC and ROSA transgenes were flushed out from the uterus at E3.5 and placed and cultured in a well of a 96-well plate in N2B27 medium (a 1:1 mixture of DMEM/F12 supplemented with N2 and Neurobasal supplemented with B27) (*Nat Biotechnol* 21, 183-186, doi:10.1038/nbt780 nbt780[pii] (2003)) with 21 (PD0325901, 0.4 μM; Stemgent; CHIR99021, 3 μM; Stemgent) and LIF (1000 U/ml) on mouse embryonic feeders (*Nature* 453, 519-523, doi:nature06968 [pii] 10.1038/nature06968 (2008)). The expanded ESC colonies were passaged by dissociating with TrypLE (Invitrogen). Until passage 4, the ESCs were maintained on feeders. At passage 4, the ESCs were stocked by Cell Banker 3 (ZENOAQ). Thereafter, male ESCs were thawed, cultured, and maintained feeder-free on a dish coated with poly-L-ornithine (0.01%; Sigma) and laminin (10 ng/ml; BD Biosciences).

The ESCs bearing the Acro/Act-EGFP (AAG) transgenes (129Sv×C57BL/6) were derived by a standard ESC derivation procedure and were adapted to the 2i+LIF, feeder-free culture condition.

The EpiSCs were derived from E5.75 epiblasts on MEFs in N2B27 medium containing activin A (20 ng/ml; Pepro-tech), bFGF (12 ng/ml; Invitrogen), and KSR (20%; Invitrogen). The cells were passaged every 3 days by dissociating with collagenase IV (1 mg/ml; Invitrogen) as cell clumps, and the cells bearing the typical morphology of EpiSCs were established after around 10 passages.

3. Induction of EpiLCs and PGC-Like Cells

The EpiLCs were induced by plating $1.0 \times 10^5$ ESCs on a well of a 12-well plate coated with human plasma fibronectin (16.7 μg/ml; Millipore) in N2B27 medium containing activin A (20 ng/ml; Peprotech), bFGF (12 ng/ml; Invitrogen), and KSR (1%; Invitrogen). The medium was changed every day. The PGC-like cells were induced in a floating condition by plating $1.0 \times 10^3$ EpiLCs in a well of a low-cell-binding U-bottom 96-well plate (NUNC) in serum-free medium [SFM; GMEM (Invitrogen) with 15% KSR, 0.1 mM NEAA, 1 mM sodium pyruvate, 0.1 mM 2-mercaptoethanol, 100 U/ml penicillin, 0.1 mg/ml streptomycin, and 2 mM L-glutamine] in the presence of the cytokines BMP4 (500 ng/ml; R&D Systems), LIF (1000 U/ml; Invitrogen), SCF (100 ng/ml; R&D Systems), BMP8b (500 ng/ml; R&D Systems), and EGF (50 ng/ml; R&D Systems).

4. Fluorescence-Activated Cell Sorting (FACS) Analysis

The induced PGC-like cells were dissociated with TrypLE (10 min., 37° C.), washed with DMEM/F12 supplemented with 0.1% BSA, and collected by centrifugation. Large clumps of cells were removed using a cell strainer (BD Biosciences). The cells were sorted and analyzed on a flow cytometer (ARIA II; BD Biosciences). The fluorescence activities of BV or EGFP and SC were detected by FITC and Pacific blue channel, respectively. For purification of PGC-like cells from AAG ESCs and iPSCs, dissociated cells were incubated with anti-Integrin-β3 antibody (BioLegend) and anti-SSEA1 antibody (eBioscience) conjugated with PE and Alexa Fluor 647, respectively. After washing with PBS supplemented with 0.1% BSA, the cells were sorted and analyzed on a flow cytometer.

5. Q-PCR, Microarray Analysis, Bisulfite Sequencing, Genotyping, AP-Staining, Immunohistochemistry and BrdU Incorporation

1) Q-PCR

Total RNAs from the isolated E5.75 epiblasts, ESCs, EpiLCs, and the FACS-sorted PGC-like and non-PGC-like cells were extracted and purified using an RNeasy micro Kit (QIAGEN). The total RNAs were reverse-transcribed by Superscript III (Invitrogen) and the first-strand cDNAs were used for Q-PCR analysis with Power SYBR Green (ABI). The primer sequences used are listed in Table 1.

2) Microarray Analysis

Global gene expression was analyzed using a GeneChip Mouse Genome 430 2.0 Array (Affymetrix). 10 μg total RNAs from ESCs, d1, d2, and d3 EpiLCs, EpiSCs, and PGC-like cells were processed according to the manufacturer's instructions. Microarray data were analyzed with the program dChip (*Proc Natl Acad Sci USA* 98, 31-36 (2001)). 13,183 probes were selected using the following criteria: (1) expression levels that ensure reproducibility (<2 fold) between biological replications, and (2) differential expressions (at least 2-fold difference between either pair of samples). Total RNAs from approximately 500 ESCs, d2 EpiLCs, EpiSCs, E5.75 epiblasts, PGC-like cells, and E9.5 PGCs were amplified as described previously (*Nucleic Acids Res* 34, e42 (2006); *Nat Protoc* 2, 739-752 (2007)) except that 12 cycles were used for the initial PCR. 9711 probes were selected for the amplified samples, using a 4-fold difference as the criterion for reproducibility and differential expression. UHC, PCA, and functional category analyses were performed using the programs TMEV4 (*Biotechniques* 34, 374-378 (2003)), R(R: A language and environment for statistical computing (Vienna, Austria, R Foundation for Statistical Computing) (2005)), and EASE (*Genome Biol* 4, R70 (2003)), respectively.

3) Bisulfite Sequencing and Genotyping

Genomic DNAs were isolated from ESCs, the FACS-sorted PGC-like cells, tails of the offspring derived from the PGC-like cells, and tails of the wild-type mice, and bisulfite reactions were performed using an EpiTect Bisulfite Kit (QIAGEN). PCR amplification of differentially methylated regions of Igf2r, Snrpn, H19, and Kcnq1ot1 was carried out using the primer sets and conditions described previously (*Genomics* 79, 530-538 (2002); *Nature* 450, 908-912 (2007)) (Table 1). The PCR products were subcloned into the pGEM-T Easy vector (Promega), and were sequenced.

Genotyping of the BVSC transgenes was performed as described previously (*Reproduction* 136, 503-514 (2008); *Nature* 448, 313-317 (2007); *Cell* 126, 663-676 (2006)) (Table 1).

4) AP-Staining and Immunohistochemistry

The AP-staining and immunohistochemistry were performed as described previously (*Reproduction* 136, 503-514 (2008); Reproduction 139, 381-393, doi:REP-09-0373 [pii] 10.1530/REP-09-0373 (2010); *J Histochem Cytochem* 47, 1443-1456 (1999)). The primary antibodies used were as follows: anti-Oct3/4 (mouse monoclonal; BD Bioscience), anti-Sox2 (rabbit polyclonal; Santa Cruz), anti-Nanog (rat monoclonal; eBioscience), anti-H3K9me2 (rabbit polyclonal; Upstate), anti-H3K27me3 (rabbit polyclonal; Upstate), and anti-Dnmt3b (mouse monoclonal; Abcam). The secondary antibodies used were as follows: Alexa Fluor 488 anti-rabbt IgG, Alexa Fluor 568 anti-rabbit, or -rat, or -mouse IgG, Alexa Fluor 633 anti-mouse IgG (all of these are goat polyclonal; Invitrogen). Immunofluorescence images were taken by a confocal microscope (Olympus FV1000).

5) BrdU Incorporation

For the analysis of BrdU incorporation, a BrdU labeling and detection kit (Roche) was used. Aggregates induced for PGC-like cells for 4 days were incubated with 10 μM of BrdU for 6 hours. After the incubation, aggregates were dissociated by TrypLE treatment, spread on a slide glass by Cytospin4 (Thermo Scientific), fixed with 70% EtOH in 50 mM glycine, and washed with PBS. The cells were then incubated with anti-BrdU and anti-GFP, followed by Alexa Fluor 568 anti-mouse IgG and Alexa 488 anti-rat IgG. Immunofluorescence images were obtained by a confocal microscope (Olympus FV1000).

6. Transplantation of the PGC-Like Cells into Seminiferous Tubules of Neonatal W/W$^v$ Mice and Intra-Cytoplasmic Sperm Injection (ICSI)

The whole aggregates [~192 (two 96-well plates) aggregates per experiment] of the PGC-like cell induction from the BVSC ESCs (C57BL/6 background) were dissociated into single cells by TripLE (Invitrogen). Recipient animals [neonatal (7- to 9-day old) W/W$^v$ mice lacking endogenous spermatogenesis (*J Exp Zool* 134, 207-237 (1957)) from a WBxC57BL/6 F1 background (SLC)] were induced into hypothermic anaesthesia on ice, and the donor cell suspension [the whole-cell dissociates or the FACS-sorted BV-positive cells (~2 μl) (Table 3)] was injected into the efferent duct of each testis (*Int J Dev Biol* 41, 111-122 (1997)). The recipient animals were returned to their littermates after surgery and analyzed after 10 weeks.

The spermatozoa derived from the induced PGC-like cells were prepared from the seminiferous tubules of recipient testis at 10 weeks after transplantation. Briefly, seminiferous tubules were isolated from the recipient testis and those with dark central areas corresponding to spermiation or with GFP fluorescence from the Acro/Act-EGFP transgenes were located under a dissection microscope. These tubules were minced gently with scissors and dissociated to obtain the spermatogenic cell suspension. The cell suspension was kept at 4° C. until ICSI. The ICSI was performed essentially as described previously (*Biol Reprod* 52, 709-720 (1995)).

7. Derivation and Culture of iPSCs, Induction of EpiLCs and PGC-Like Cells, and Analysis Thereof.

The male iPSCs (MEF-Ng-20D-17: Nature 448, 313-317 (2007); MEF-Ng-178B-5: *Nat Biotechnol* 26, 101-106 (2008); MEF-Ng-492B-4: *Science* 322, 949-953 (2008)) were obtained from RIKEN BRC. The iPSCs were maintained in N2B27 medium (a 1:1 mixture of DMEM/F12 supplemented with N2 and Neurobasal supplemented with B27) with 21 (PD0325901, 0.4 μM; Stemgent; CHIR99021, 3 μM; Stemgent) and LIF (1000 U/ml) on a dish coated with poly-L-ornithine (0.01%; Sigma) and Laminin (10 ng/ml, BD Biosciences).

The induction of EpiLCs and PGC-like cells from iPSCs were performed in the same manner as 3. above. The EpiLCs and PGC-like cells induced were analyzed in the same manner as 5. above.

Example 1

Pre-Gastrulating Epiblast-Like Cells (EpiLCs) from ESCs

Male ESCs bearing the Blimp1-mVenus and stella-ECFP reporters (BVSC) (*Reproduction* 136, 503-514 (2008)) on the C57BL/6 background were derived and maintained in N2B27 medium with an inhibitor against MAPK signalling (PD0325901, 0.4μM), an inhibitor against GSK3 (CHIR99021, 3 μM), and LIF (1000 U/ml) [2i+LIF], a condition that keeps ESCs in the ~E3.5-E4.5 ICM/early epiblast-like state (the ground state) (*Nature* 453, 519-523, doi:nature06968 [pii] 10.1038/nature06968 (2008); *Development* 136, 3215-3222, doi:dev.038893 [pii] 10.1242/dev.038893 (2009)). Among a variety of conditions examined, we found that stimulation, on a fibronectin-coated dish, with activin A (20 ng/ml), bFGF (12 ng/ml), and Knockout™ Serum Replacement (KSR) (1%), resulted in the uniform induction of highly-compacted ESC colonies into more flattened epithelial structures resembling the epiblasts over the course of a 3-day period (FIGS. 1A, B). Upon the stimulation, the cells grew relatively rapidly for the first two days but thereafter underwent a significant extent of cell death, and the number of the surviving cells at day 3 was similar to that at day 2 (FIG. 1C). The cells at day 3 showed a more elongated and spiny morphology (FIG. 1B).

Figure 1B:
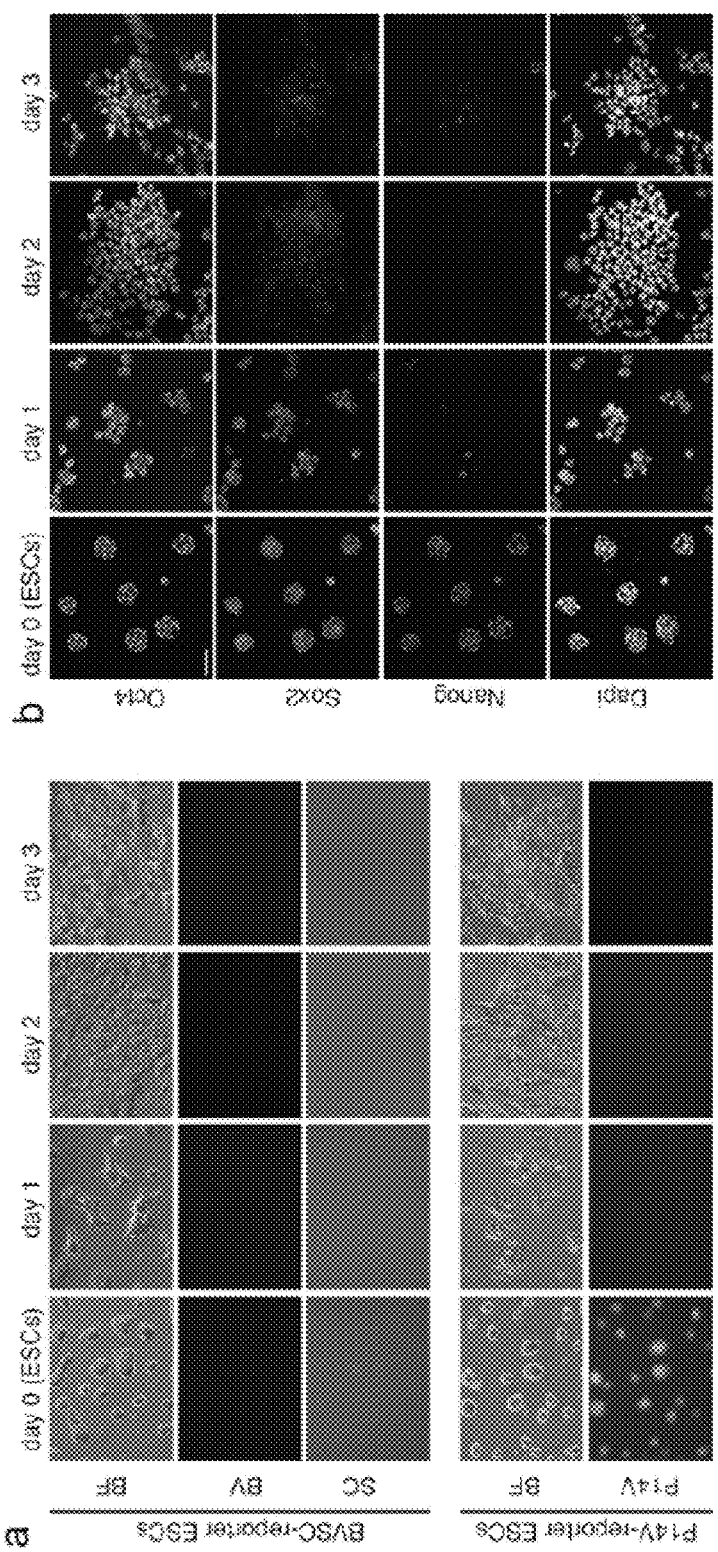
FIG. 1B, (a) Induction of the EpiLCs from ESCs with Blimp1-mVenus and stella-ECFP (BVSC) (top) and Prdm14-mVenus (P14V) (bottom) transgenes. Bright-field images and fluorescence images from the reporters are shown. The EpiLCs inductions were performed over three days. Bar, 50 μm. (b) Immunofluorescence analysis of the expression of Oct3/4 (top row), Sox2 (second), and Nanog (third) counterstained by DAPI (bottom) during the EpiLC (day 1, day 2, and day 3) induction from ESCs. Bar, 50 μm.
Figure 1C:
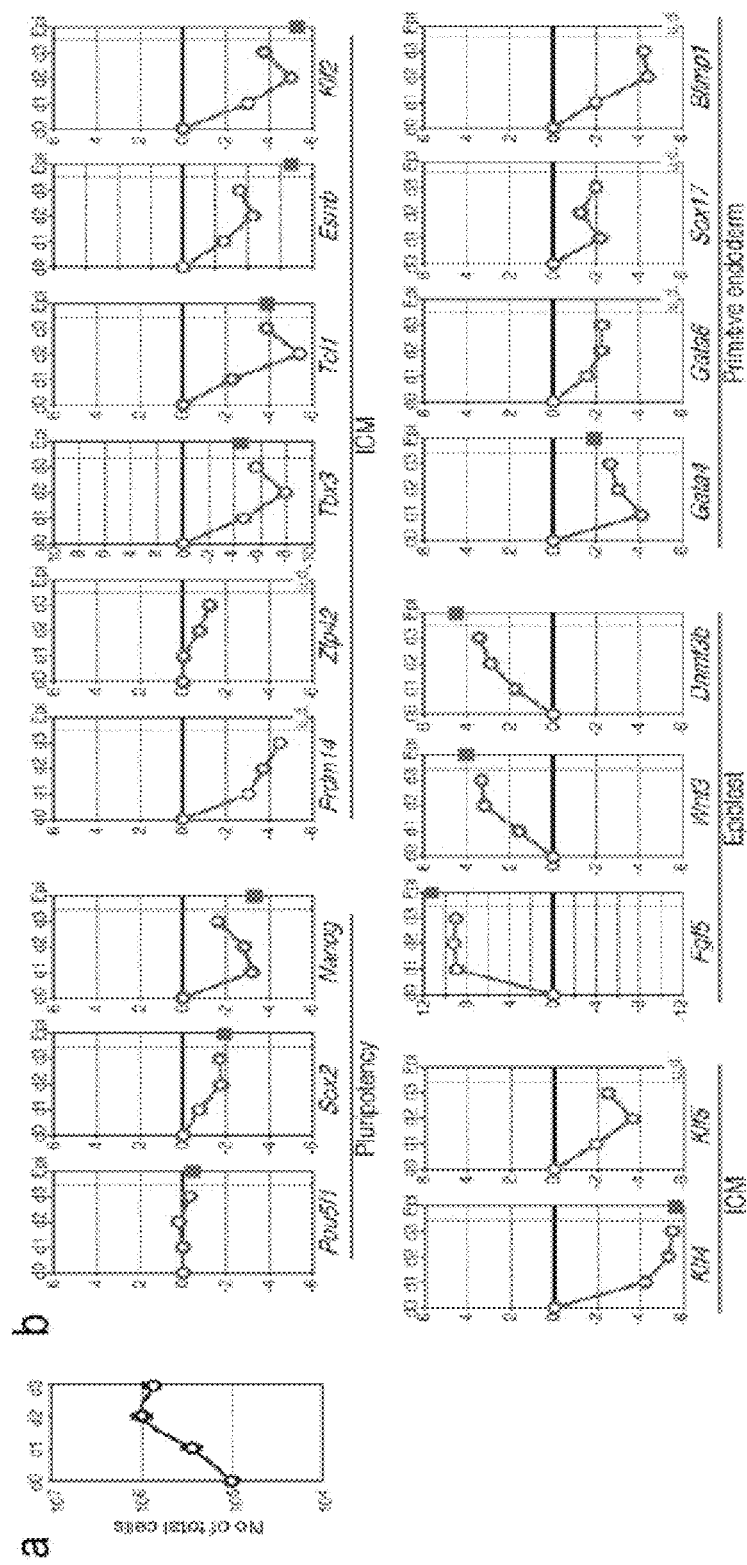
FIG. 1C, (a) Cell growth during the EpiLC induction. Average cell numbers with standard deviations from three independent experiments are shown. (b) Gene expression profiles during the EpiLC induction and of the epiblasts at E5.75 measured by Q-PCR. For each gene examined, the ΔCT from the average CT values of the two independent housekeeping genes Arbp and Ppia was calculated. The value for ESCs was set as 0. For each point, the average value from three and two independent experiments for EpiLCs (red open circles) and epiblasts (red filled squares), respectively, is shown on the $\log_2$ scale. u.d., undetectable.

We observed no BVSC expression in the ESCs in the ground state or in the induced epiblast-like cells (hereafter called EpiLCs) during the 3-day differentiation period (FIG. 1B). An independent ESC line bearing the Prdm14 reporter (Prdm14-mVenus; P14V) (*Nat Genet* 40, 1016-1022 (2008)) exhibited a similar differentiation upon stimulation by activin A, bFGF, and KSR: Prdm14 was expressed in the ESCs but declined sharply along with the EpiLC induction (FIG. 1B). Immunofluorescence analysis of the expression of key pluripotency proteins (Oct3/4, Sox2, and Nanog) (for review, see *Development* 136, 2311-2322, doi:136/14/2311 [pii]10.1242/dev.024398 (2009)) showed that, during the EpiLC induction, Oct3/4 was continuously expressed, but Sox2 and Nanog were decreased by day 2 and day 1, respectively (FIG. 1B). To examine the properties of the EpiLCs more precisely, we compared the expression of a number of markers between the EpiLCs and the isolated epiblasts at E5.75 by quantitative (Q)-PCR. In good agreement with the reporter gene expression and immunofluorescence analysis, during the course of EpiLC differentiation, Oct3/4 was expressed at a relatively constant level, whereas genes more tightly associated with the ICM state, such as Sox2, Nanog, and Prdm14, as well as Zfp42 (Rex1), Tbx3, Tcl1, Esrrb, Klf2, Klf4, and Klf5, were down-regulated to levels similar to those in the epiblasts (FIG. 1C). In contrast, the expression of genes such as Wnt3, Fgf5, and Dnmt3b, which are up-regulated in the epiblasts (*Nat Genet* 22, 361-365 (1999), *Dev Dyn* 233, 1064-1075 (2005), *Development* 112, 397-406 (1991), *Development* 112, 407-415 (1991), *Cell* 99, 247-257 (1999), *Gene Expr Patterns* 9, 27-30, doi:S1567-133X(08)00108-7 [pii] 10.1016/j.gep.2008.09.002 (2009)), was indeed elevated (FIG. 1C). Notably, contrary to EpiSCs, endoderm markers such as Gata4, Gata6, and Sox17 were down-regulated or remained very low (FIG. 1C). It is also important to note that Blimp1, which, apart from PGCs, shows expression in the visceral and definitive endoderm, was further down-regulated in EpiLCs (FIG. 1C). These findings indicate that the ESCs cultured in the ground state are induced into pre-gastrulating epiblast-like cells, albeit transiently, by the stimulation with activin A, bFGF, and KSR. In particular, the day-2 EpiLCs are very similar to the pre-gastrulating epiblasts with regard to their morphology and gene expression.

Example 2

PGC-Like Cell Induction from ESCs Through EpiLCs

We next examined whether the EpiLCs are induced into PGC-like cells, as in the case of the pre-gastrulating epiblasts in vivo. Such induction was considered to be a critical indicator of whether or not the EpiLCs bear the functional properties of the pre-gastrulating epiblasts. We cultured the BVSC ESCs and day-1, -2, and -3 EpiLCs under a floating condition (1,000 cells per well of a low-cell-binding U-bottom 96-well plate) in the SFM alone, or in the SFM with LIF (1000 U/ml), or BMP4 (500 ng/ml), or BMP4 and LIF for 2 days. As shown in FIG. 2A, no significant BV induction was observed in any of the aggregates cultured in the SFM alone or SFM with LIF. In contrast, when cultured in the SFM with BMP4 or with BMP4 and LIF, prominent and relatively uniform BV induction was seen specifically in aggregates from day-2 EpiLCs, but not in aggregates from ESCs or day-1 EpiLCs (FIG. 2A). Aggregates from day-3 EpiLCs also exhibited BV induction, but they were much smaller and looked less integrated compared to those from other origins (FIG. 2A). SC did not appear to be induced under any conditions during the 2-day culture period. These findings indicate that, like the epiblasts at E5.5-E6.0, EpiLCs, particularly day-2 EpiLCs, bear the competence to express Blimp1 specifically in response to BMP4.

To explore whether the BV-positive cells induced from EpiLCs further develop into PGC-like cells, we performed floating cultures of the day-2 EpiLCs in the SFM alone, or in the SFM with BMP4, or with BMP4 and LIF, or with BMP4, LIF, SCF (100 ng/ml), BMP8b (500 ng/ml), and EGF (50 ng/ml) [the full induction condition (Cell 137, 571-584 (2009))] for 6 days. When the day-2 EpiLCs were cultured in the SFM alone, no significant BVSC induction was observed during the 6-day period (FIG. 2B). When they were cultured in the SFM with BMP4, BV was strongly induced on day 2. On day 4, the aggregates grew well and the BV-positive cells formed several tight clusters, some of which were weakly positive for SC. On day 6, the aggregates developed further, but the BV-positive foci became much smaller, although most of them were SC-positive (FIG. 2B). When the day-2 EpiLCs were cultured in the SFM with BMP4 and LIF, on day 2, the aggregates showed strong BV induction, and on day 4, the BV-positive cells formed tight and larger clusters, most of which, notably, exhibited SC induction. On day 6, the BVSC-positive foci became smaller and looked more scattered but did persist and moved peripherally in the aggregates (FIG. 2B). From day 4 to day 6, the BVSC-negative population exhibited more rapid expansion. When cultured under the full induction condition, on day 2, the aggregates exhibited uniform BV, and on day 4, BV-positive cells moved peripherally and initiated explicit SC expression. On day 6, the entire aggregates expanded and the BVSC-positive cells proliferated to cover the aggregates (FIG. 2B). The structural development of the aggregates and the appearance of the BVSC-positive PGC-like cells from the day-2 EpiLCs under the full induction condition were strikingly similar to those from the epiblasts (Cell 137, 571-584 (2009)). These findings demonstrate that the day-2 EpiLCs are induced into BVSC-positive PGC-like cells essentially by BMP4, and the maintenance/survival/proliferation of the BVSC-positive cells are enhanced by LIF and more robustly by the combinatorial effects of LIF, SCF, BMP8b and EGF.

Figure 2C:
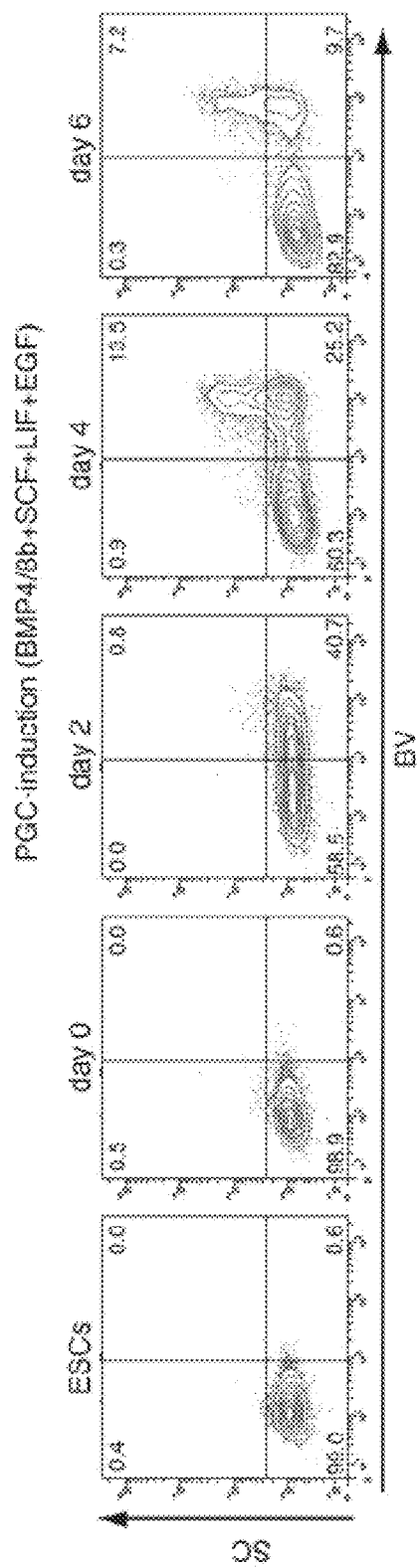
FIG. 2C, FACS analysis of the BVSC expression from day-2 EpiLCs under the full induction condition during the 6-day culture.
Figure 2D:
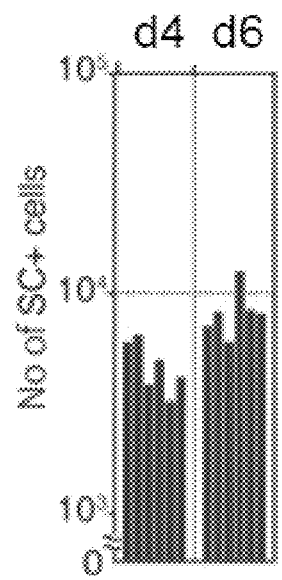
FIG. 2D, The numbers of SC-positive cells at day 4 and 6 under the full induction condition from the day-2 EpiLCs. Each bar represents the number of BVSC-positive cells from 10 aggregates.
Figure 5:
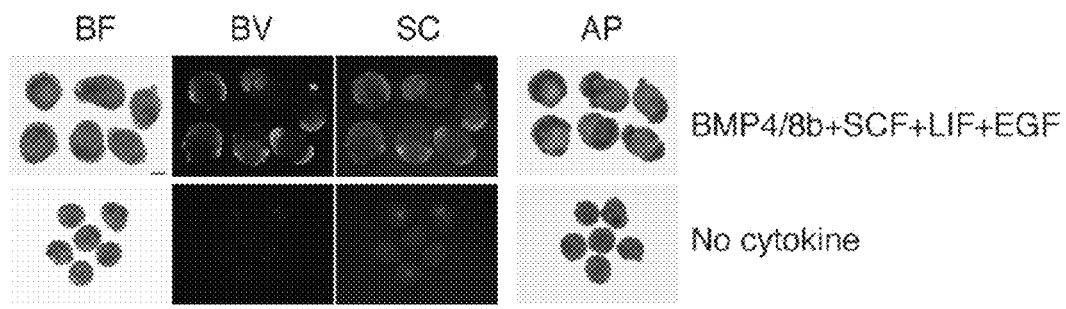
FIG. 5 shows that the BVSC-positive cells are AP-positive. The BVSC-positive cells induced for 6 days by BMP4 (500 ng/ml), LIF (1000 U/ml), SCF (100 ng/ml), BMP8b (500 ng/ml), and EGF (50 ng/ml) from the day-2 EpiLCs were alkaline phosphatase (AP)-positive. Bar, 200 µm.
Figure 6:
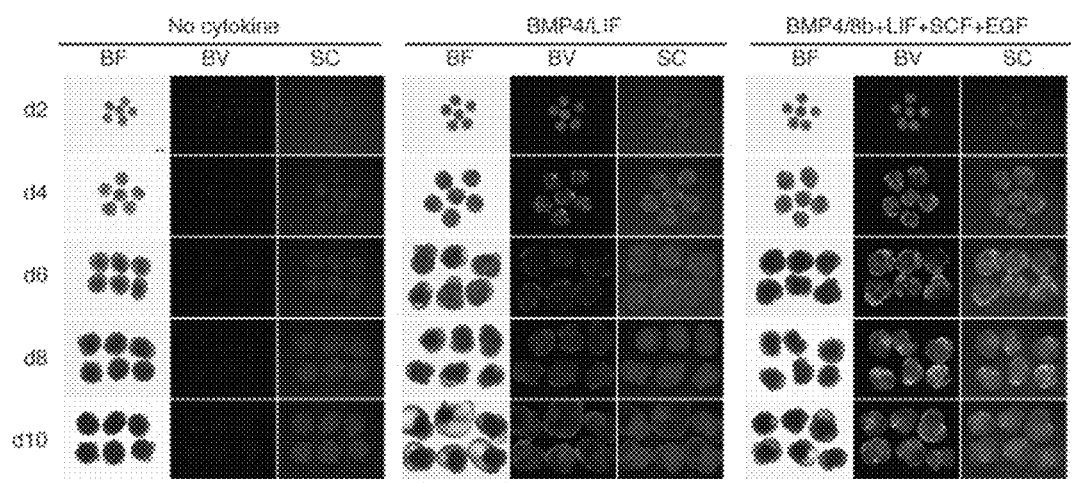
FIG. 6 shows that the BVSC-positive cells persist up to 10 days in culture. The BVSC-positive cells were induced from the day-2 EpiLCs by BMP4 alone (500 ng/ml) or by BMP4 (500 ng/ml) and LIF (1000 U/ml). However, they were not maintained after day 6. In contrast, the BVSC-positive cells persisted robustly up to 10 days when induced by BMP4 (500 ng/ml), LIF (1000 U/ml), SCF (100 ng/ml), BMP8b (500 ng/ml), and EGF (50 ng/ml). Bar, 200 µm.
Figure 7:
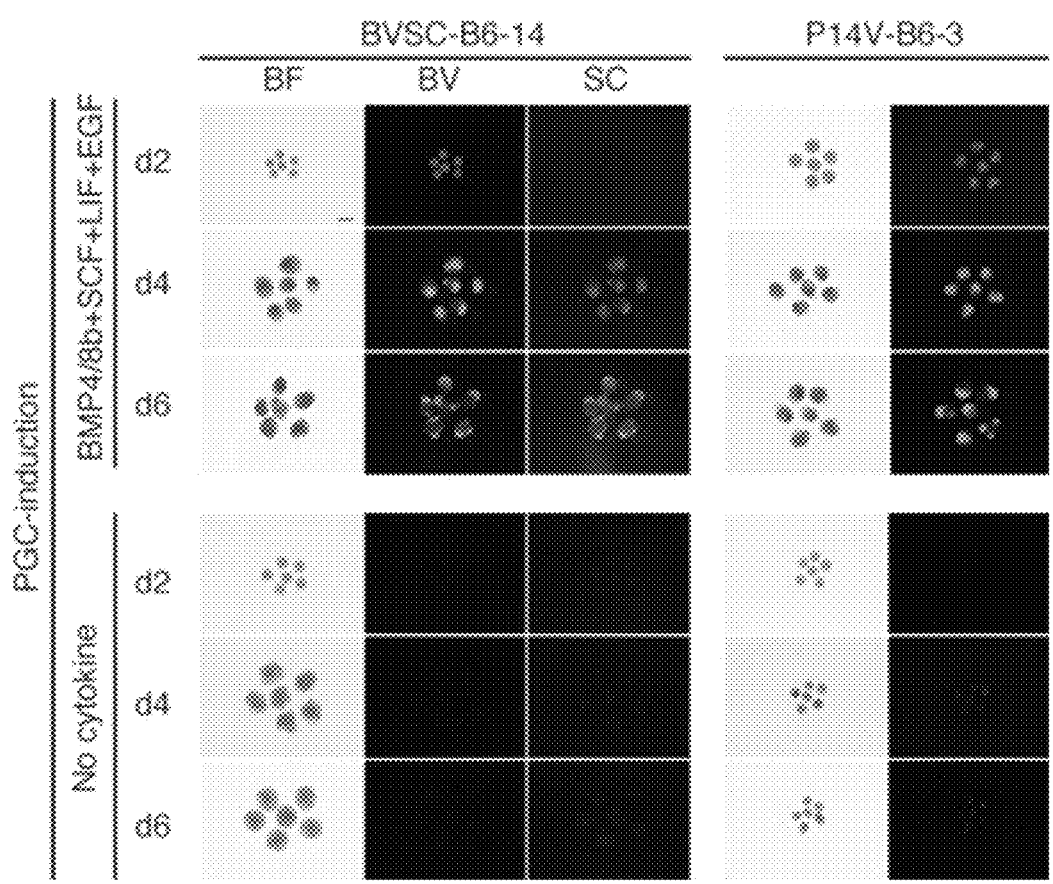
FIG. 7 shows the PGC-like cell induction from independent ESC lines. PGC-like cells (day 2, 4, and 6) were induced under the full induction condition [BMP4 (500 ng/ml), LIF (1000 U/ml), SCF (100 ng/ml), BMP8b (500 ng/ml), and EGF (50 ng/ml) in the SFM] from day-2 EpiLCs derived from independent ESC lines, BVSC-B6-14, and P14V-B6-3. Control experiments with no cytokines are also shown. Bar, 200 µm.

We analysed the development of BVSC-positive cells from the day-2 EpiLCs under the full induction condition by fluorescence-activated cell sorting (FACS), which showed that BV was indeed strongly induced as early as day 2 (~40.7%) and SC arose from the BV-positive cells at around day 4 (BV: ~38.7%; BVSC: ~13.5%) (FIG. 2C). The numbers of SC-positive cells per 1,000-cell aggregate as quantified under an inverted fluorescence microscope were approximately 480 and 900 on day 4 and 6, respectively (FIG. 2D). We confirmed that the BVSC-positive areas were alkaline phosphatase (AP)-positive (FIG. 5). The BVSC-positive cells remained up to 10 days under the full induction condition (FIG. 6). Furthermore, we were able to reproduce the induction of BVSC or P14V-positive PGC-like cells through the EpiLCs from several independent ESC lines cultured in the ground state (FIG. 7 and data not shown). Collectively, these findings support the notion that the day-2 EpiLCs are the culture equivalent, although perhaps not in every detail, of the E5.5-E6.0 epiblasts, and that the PGC-like cell induction from ESCs in the ground state through the EpiLCs is a robust process with high reproducibility.

Figure 10A:
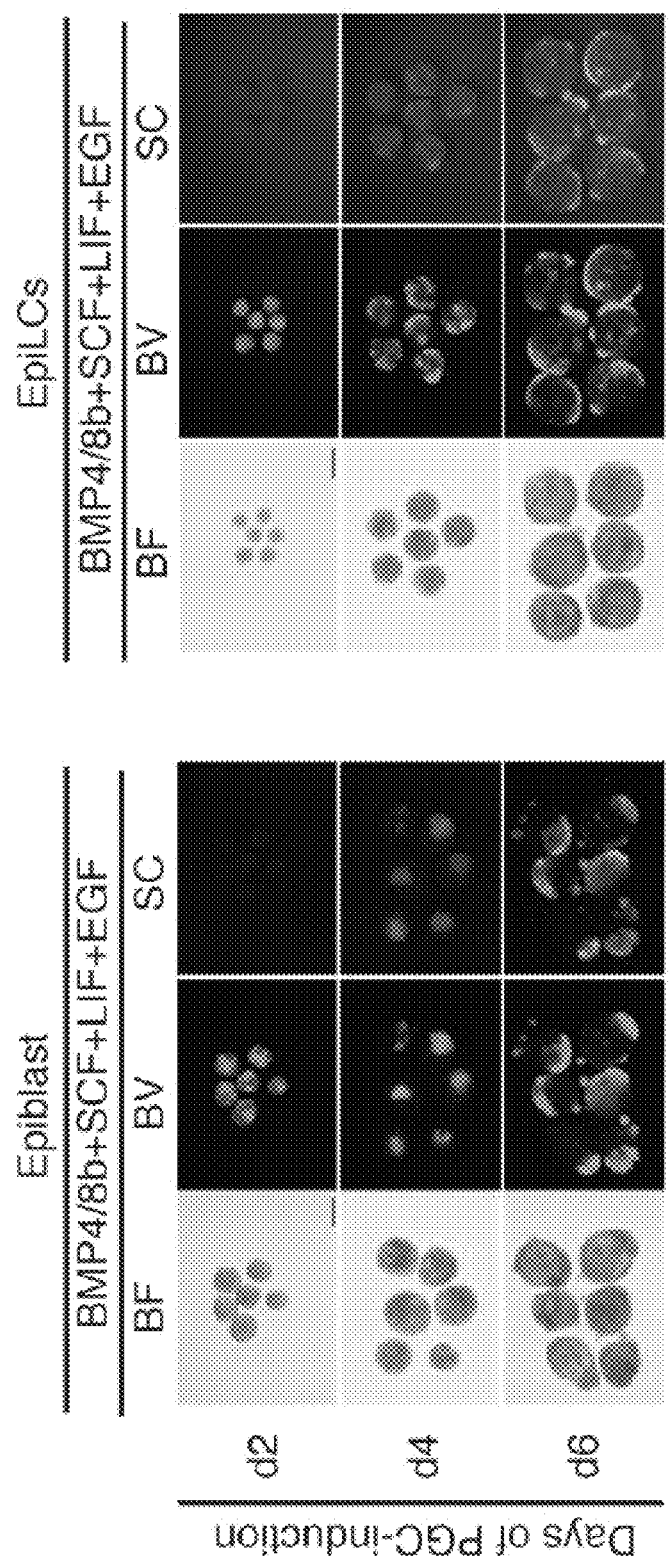
FIG. 10A, PGC-like cell induction from E5.75 epiblasts (left) and day 2 EpiLCs (right, the same data as shown in FIG. 2B) under the full induction condition. Bar, 200 µm.
Figure 10B:
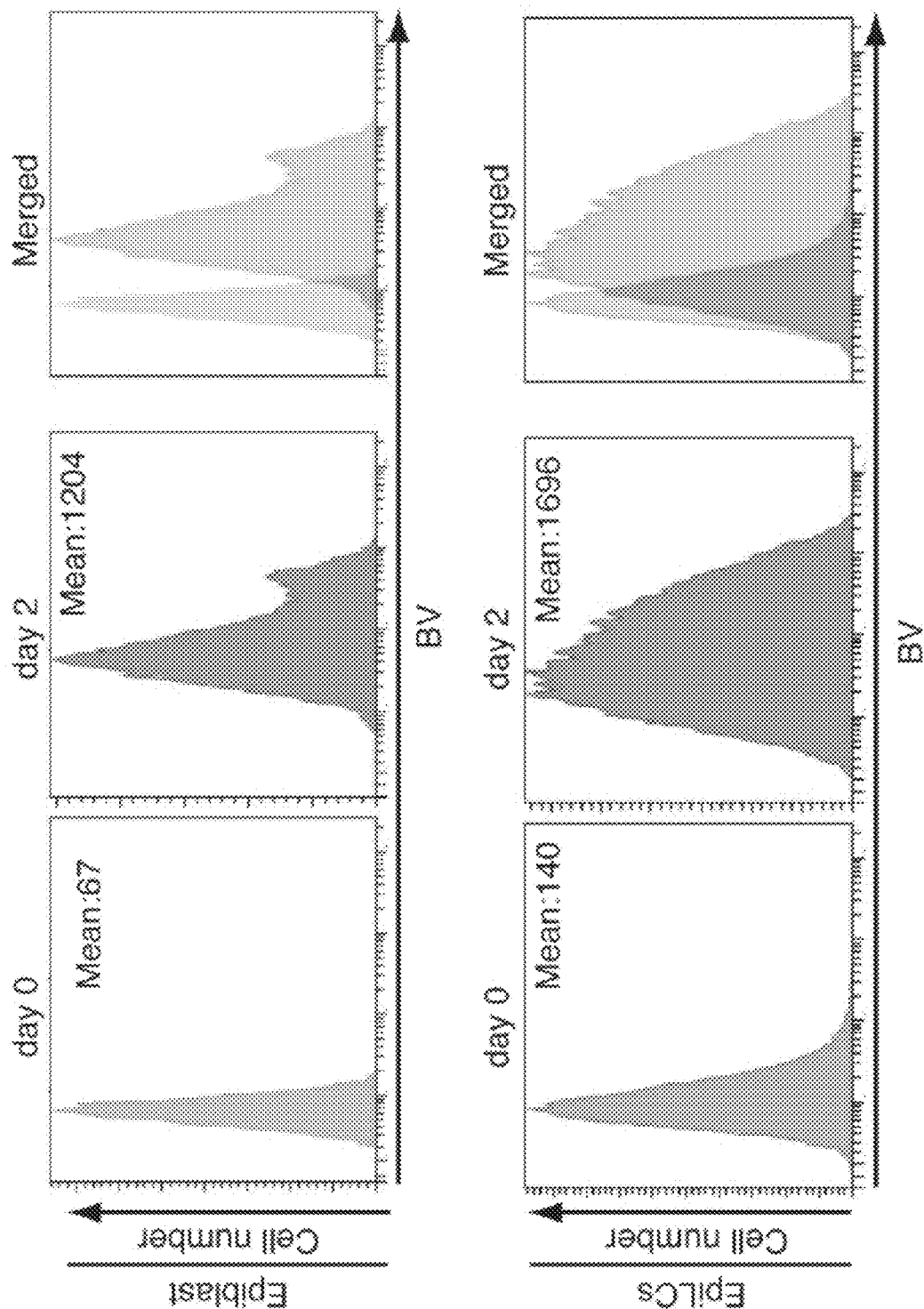
FIG. 10B, Measurements of BV expression in epiblasts (top) or day 2 EpiLCs (bottom) at day 0 (left, grey) and day 2 (middle, red) of PGC-like cell induction. Merged profiles are shown on the right. Note that a great majority of both E5.75 epiblasts and day 2 EpiLCs shifted toward the BV-positive state upon induction, although the response of the epiblasts was somewhat more cohesive.
Figure 10C:
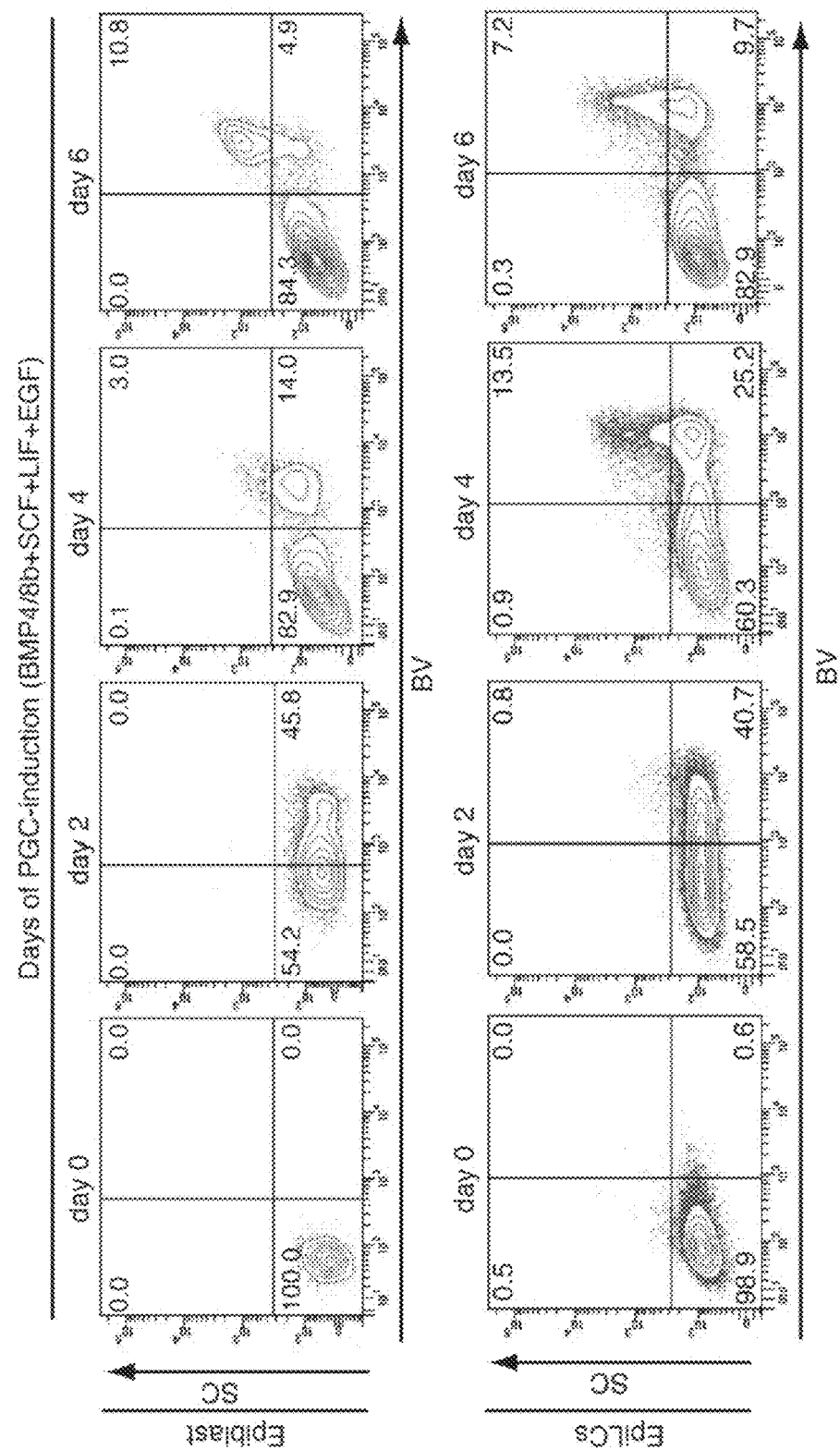
FIG. 10C, FACS analysis of BVSC expression from E5.75 epiblasts (top) and day 2 EpiLCs (bottom, the same data as shown in FIG. 2C) under the full induction condition during the 6-day culture.

We compared the BVSC(+) cell induction from d2 EpiLCs with that from the epiblasts. The structural development of the aggregates and the efficiency and dynamics of BVSC(+) cell induction from the d2 EpiLCs under the full induction condition were similar to those from the epiblasts (FIG. 10A): On day 2, ~45.8% of the epiblast cells (as compared to ~41.5% of d2 EpiLCs) exhibited strong BV positivity and the cell number/BV positivity plots revealed that a majority of both the d2 EpiLCs and the epiblast cells were shifted toward the BV-positive state (FIG. 10B), indicating that the d2 EpiLCs and the epiblasts bear similar competence to express Blimp1 in response to BMP4. On days 4/6, the efficiency and mode of the emergence of the BVSC(+) cells from the d2 EpiLCs and the epiblasts were again similar, although the response of the epiblast cells appeared somewhat more cohesive (FIG. 10C). These findings confirm that the d2 EpiLCs bear similar, if not identical, properties to the pre-gastrulating epiblast cells.

Example 3

Gene Expression Dynamics Associated with PGC-Like Cell Induction

Figure 2F:
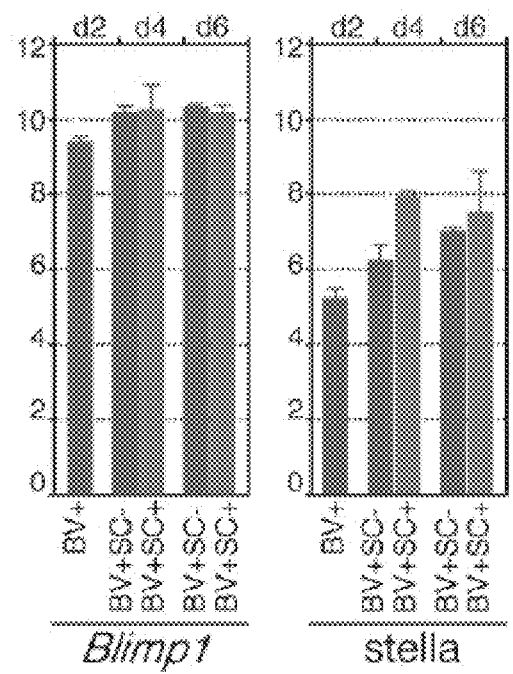
FIG. 2F, Blimp1 (left) and stella (right) expression levels with SDs in BV(+) (day 2) and BV(+)SC(−) (green bars) or BVSC(+) (blue bars) cells (days 4/6), determined as described in FIG. 2E.
Figure 2E:
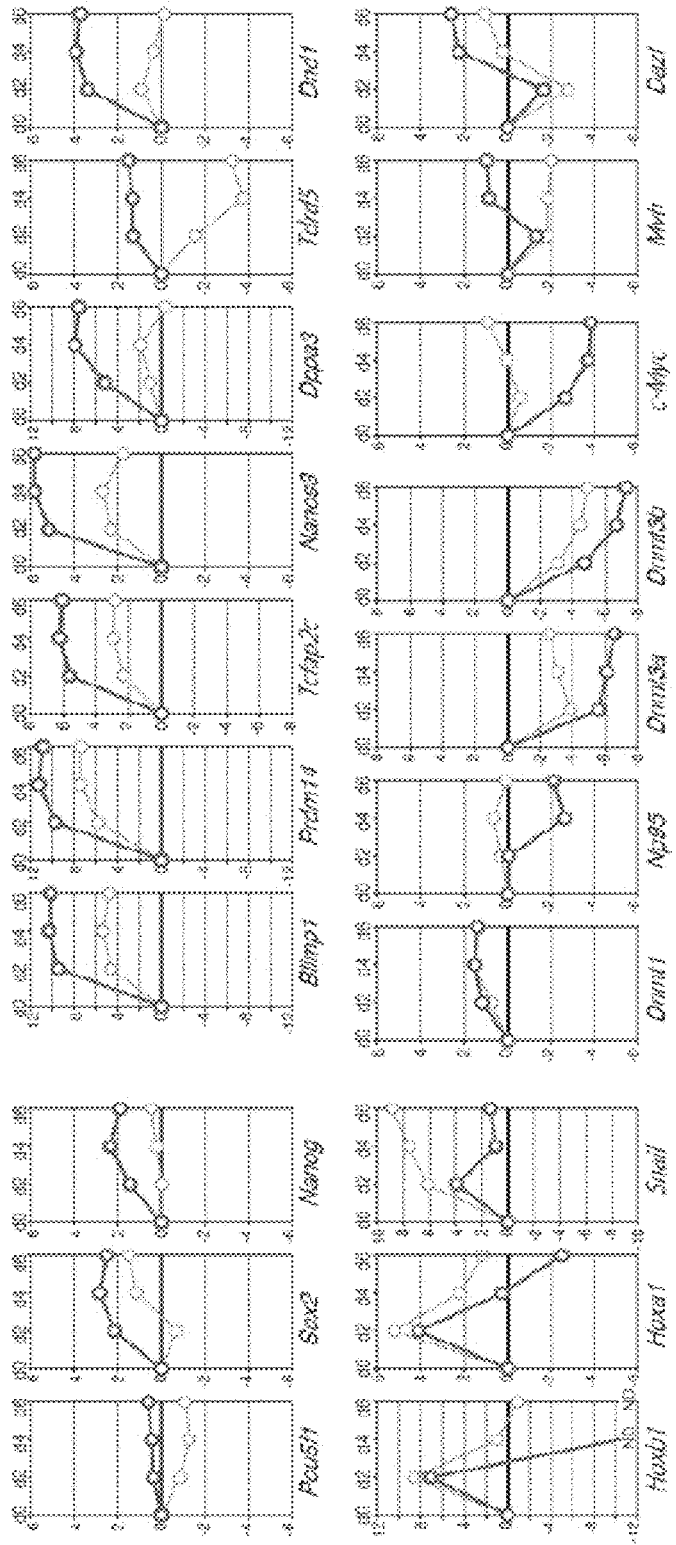
FIG. 2E, Gene expression dynamics during the PGC-like cell induction from the day-2 EpiLCs. For each gene examined, the ΔCT from the average CT values of the two independent housekeeping genes Arbp and Ppia was calculated. For each point, the average value from two independent experiments is plotted on the $\log_2$ scale. Red circles and lines, values of BV- or BVSC-positive cells (day 2 and day 4/6, respectively); blue circles and lines, values of BV- or BVSC-negative cells (day 2 and day 4/6, respectively).

To gain a more critical insight on the process of PGC-like cell induction, we evaluated the gene expression dynamics associated with PGC-like cell induction from the day-2 EpiLCs by Q-PCR (FIG. 2E). While Oct3/4 was up-regulated slightly in BV- and BVSC-positive (day 2 and day 4/6, respectively) cells, Sox2 and Nanog, which were down-regulated in the day-2 EpiLCs (FIG. 1E), were regained significantly in these PGC-like cells. Genes specifically up-regulated upon PGC specification, including Blimp1, Prdm14, Tcfap2c, Nanos3, stella (Dppa3), Tdrd5, and Dnd1, were all highly elevated in BV- and BVSC-positive cells. In contrast, genes associated with a somatic mesodermal program, such as Hoxa1, Hoxb1, and Snai1, showed transient up-regulation in BV-positive cells at day 2 but subsequently exhibited drastic repression in BVSC-positive cells at day 4 and 6. On the other hand, Dnmt3a and 3b, Np95 encoding a critical co-factor for Dnmt1, and c-Myc were monotonically down-regulated. Genes associated with later germ cell development, such as Mvh and Dazl, showed slight up-regulation in BVSC-positive cells. Thus, the gene expression dynamics associated with PGC-like cell induction in vitro is strikingly similar to that with PGC specification in vivo (*Genes Dev* 22, 1617-1635 (2008), *Nature* 418, 293-300 (2002), *Biol Reprod* 75, 705-716 (2006)).

We noted that at day 6, the level of endogenous stella mRNA in BV(+)SC(−) cells was similar to that in BVSC(+) cells (FIG. 2F). Since the SC expression becomes eminent only after E9.5, 2.5 days later than the onset of stella expression (*Reproduction* 136, 503-514 (2008), *Nature* 418, 293-300 (2002)), this finding indicates that many of the BV(+)SC(−) cells, especially those at a later stage of induction, express endogenous stella at a high level, and thus should be considered established PGC-like cells.

Notably, BV- or BVSC-negative cells retained/regained relatively high levels of Oct3/4, Sox2, and Nanog, and up-regulated germ-cell-specific genes to some extent (FIG.

2E). This is consistent with the idea that essentially all the day-2 EpiLCs are directed toward the germ cell fate by cytokines, most importantly, BMP4, and those that acquire Blimp1 at a sufficient level succeed in progressing further toward PGC-like cells, while those that fail to gain sufficient Blimp1, due to some stochastic parameter or subtle intrinsic difference, result in a non-germ cell trait.

Next, to determine the global transcription dynamics for PGCLC induction, we isolated total RNAs from ESCs, d1/2/3 EpiLCs, EpiSCs, E5.75 epiblasts, BVSC-positive PGC-like cells at day 6 of induction, and stella-EGFP(+) PGCs at E9.5 (*Genesis* 44, 75-83 (2006)). We performed two sets of microarray hybridization; one with non-amplified RNAs from ESCs, d1/2/3 EpiLCs, EpiSCs, and PGC-like cells, and the other with amplified RNAs from ESCs, d2 EpiLCs, EpiSCs, E5.75 epiblasts, PGC-like cells, and E9.5 PGCs.

Figure 11A:
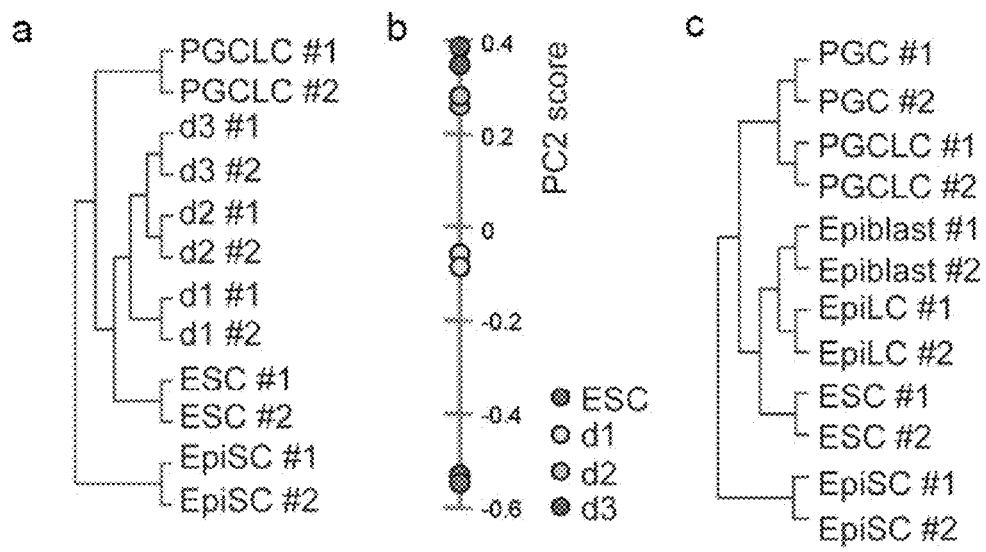
FIG. 11A, (a) Unsupervised hierarchical clustering (UHC) of non-amplified RNAs from ESCs, day (d) 1, d2, and d3 EpiLCs, EpiSCs, and PGC-like cells (PGCLCs). (b) Scores of principal component (PC) 2 of ESCs and d1, 2, and 3 EpiLCs. (c) UHC of amplified RNAs from ESCs, d2 EpiLCs, EpiSCs, E5.75 epiblasts, PGCLCs and E9.5 PGCs.

Unsupervised hierarchical clustering (UHC) of non-amplified samples showed that two independent samples from ESCs, d1/2/3 EpiLCs, EpiSCs, and PGC-like cells were clustered tightly together (FIG. 11A(a)), reflecting the reproducibility of the PGC-like cell induction. Principal component analysis (PCA) provided ESCs, d1, d2, and d3 EpiLCs with PC2 scores of progressively increasing values, suggesting that EpiLC induction from ESCs is a directional and progressive process (FIG. 11A(b)). EpiSCs were clustered distantly from the other samples (FIG. 11A(a)), indicating their divergence from the other cell types.

Figure 11B:
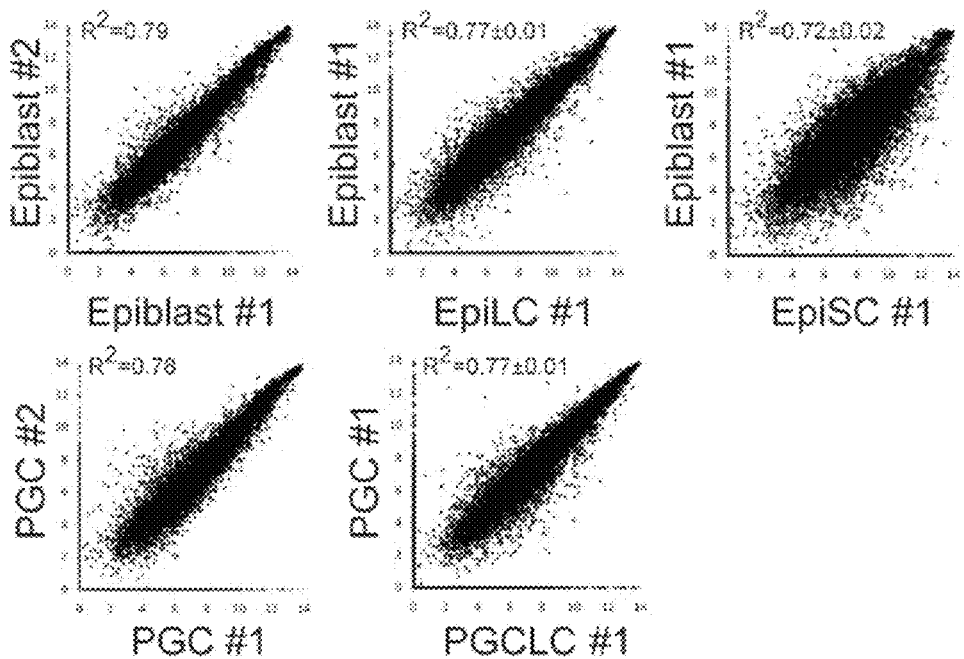
FIG. 11B, Comparison by scatter plots of transcriptome of E5.75 epiblasts with d2 EpiLCs and EpiSCs, and of E9.5 PGCs with BVSC(+) PGCLCs at day 6.
Figure 11C:
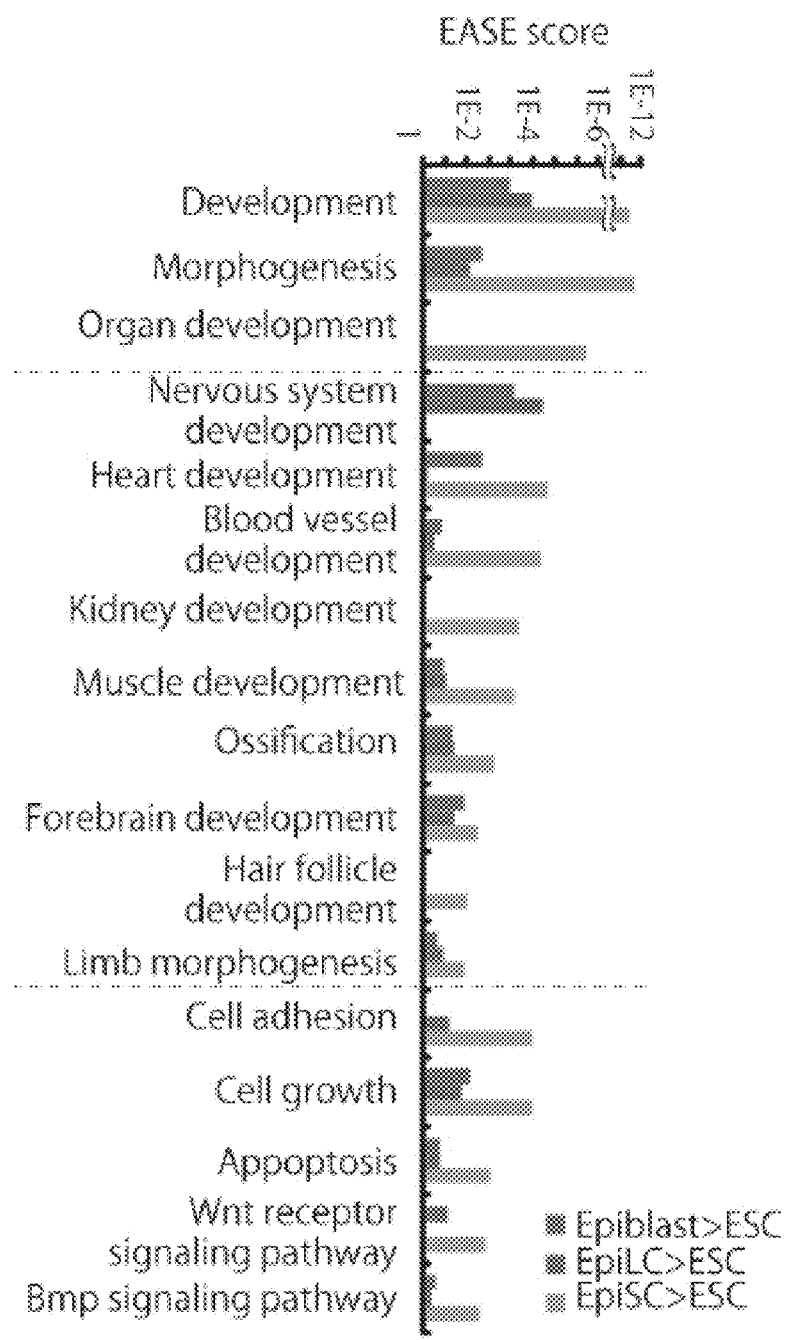
FIG. 11C, PCA of amplified RNAs from ESCs, d2 EpiLCs, EpiSCs, E5.75 epiblasts, PGCLCs, and E9.5 PGCs.
Figure 11D:
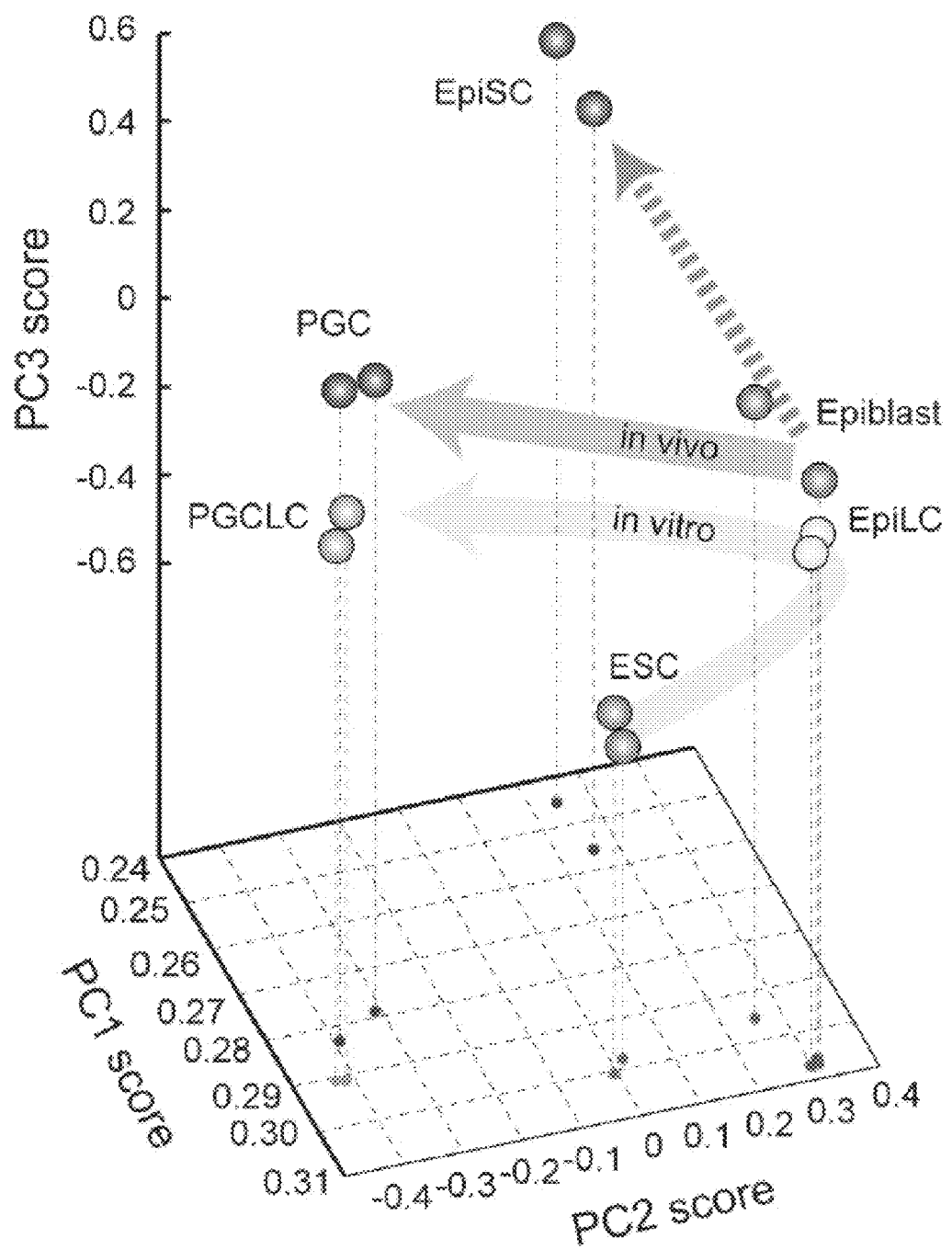
FIG. 11D, Functional categories overrepresented in genes up-regulated in the epiblasts, EpiLCs, and EpiSCs, compared with ESCs.

UHC of amplified samples showed that, first, two independent samples from all cell types were again clustered together, and second, d2 EpiLCs and PGC-like cells were clustered most closely with E5.75 epiblasts and E9.5 PGCs, respectively, whereas EpiSCs were clustered distantly from the other cell types (FIG. 11A(c)). Scatter plot analysis demonstrated close similarities between d2 EpiLCs and E5.75 epiblasts and between PGCLCs and E9.5 PGCs, and a relatively large difference between EpiSCs and E5.75 epiblasts (FIG. 11B). We plotted all cell types in a three-dimensional space defined by three major parameters generated by PCA (FIG. 11D). Notably, the pathway of PGC-like cell induction from d2 EpiLCs was parallel to that of E9.5 PGC formation from E5.75 epiblasts (FIG. 11D). Furthermore, EpiSC derivation from epiblasts involves a discrete pathway (FIG. 11D), reflected by a distinct PC1 (representing 61% of the total variance) score. These findings emphasize that PGC-like cell formation from ESCs through EpiLCs is a recapitulation of PGC formation from epiblasts.

We listed and classified the genes up-regulated in E5.75 epiblasts, d2 EpiLCs, and EpiSCs relative to the levels in ESCs. This analysis revealed that EpiSCs up-regulated more genes associated with the development of a variety of organ systems (heart, blood vessels, kidneys, muscle, and bone) than E5.75 epiblasts and d2 EpiLCs (FIG. 11C), demonstrating that EpiSCs acquire more developmentally advanced characteristics than E5.75 epiblasts and d2 EpiLCs during their derivation.

Example 4

Epigenetic Profiles and Cellular Dynamics of the PGC-Like Cells

Figure 3A:
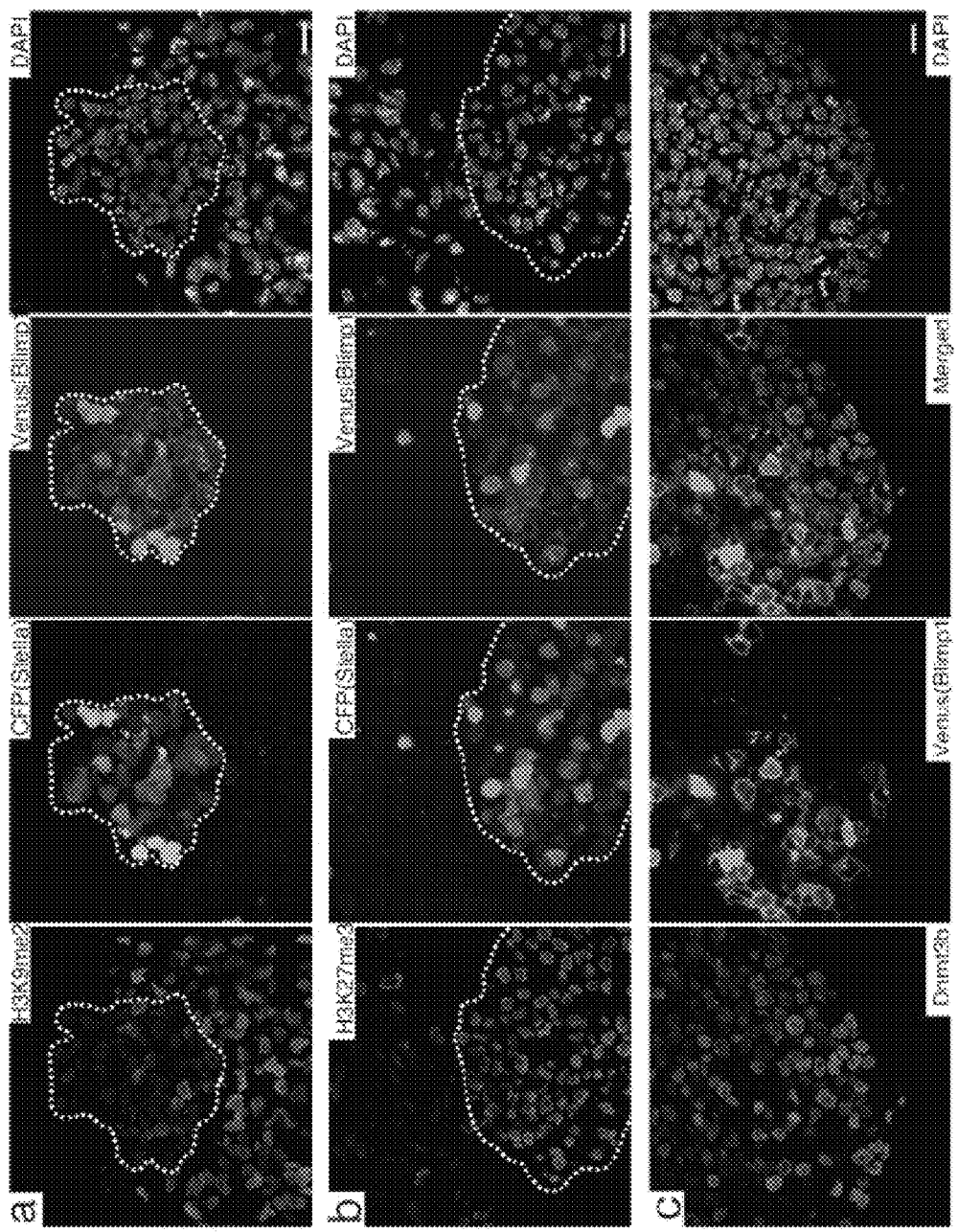
FIG. 3A, Reduced H3K9me2 (a), elevated H3K27me3 (b), and repressed Dnmt3b (c) in BVSC-positive cells from the day-2 EpiLCs under the full induction condition at day 6. Images with DAPI staining are shown on the right. Bar, 20 µm.
Figure 3B:
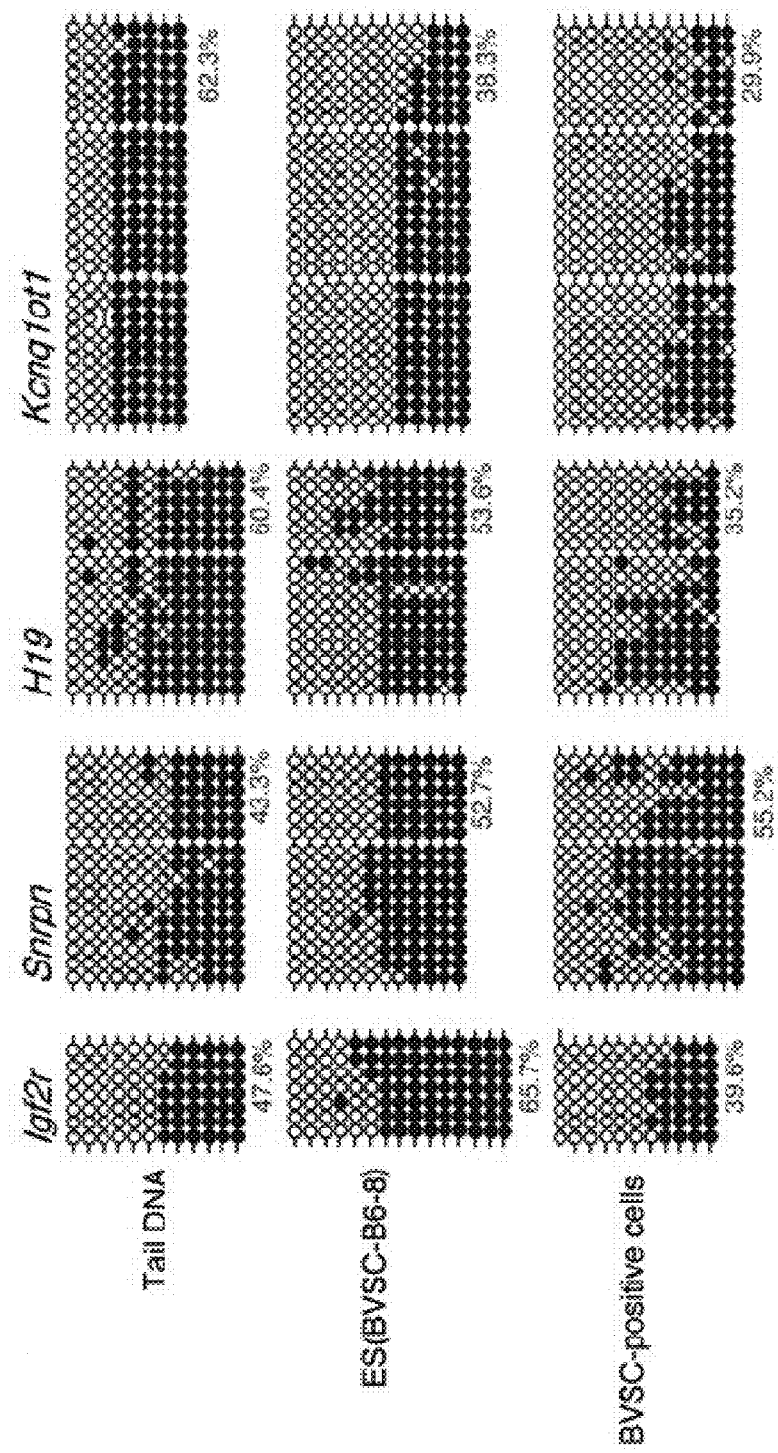
FIG. 3B, Bisulfite sequence analysis of the cytosine methylation of differentially methylated regions of the imprinted genes (Igf2r, Snrpn, H19, and Kcnq1ot1) in the genome from the tail of a wild-type C57BL/6 mouse (top), the BVSC-ESCs (middle), and the day-6 BVSC-positive PGC-like cells (bottom). White and black circles represent unmethylated and methylated CpG sequences, respectively.

We next determined the epigenetic properties of the BVSC-positive cells induced from the day-2 EpiLCs under the full induction condition at day 6. We found that the BVSC-positive cells appeared to have significantly reduced H3K9me2 and instead highly elevated H3K27me3 (FIG. 3A(a), (b)). Consistent with the Q-PCR analysis, the BVSC-positive cells were negative for Dnmt3b (FIG. 3A(c)). We then determined the imprinting states of maternally expressed (Snrpn, Kcnq1ot1) and paternally expressed (Igf2r, H19) imprinted genes by a bisulfite sequencing analysis of the differentially methylated regions of these genes. As shown in FIG. 3B, while the BVSC-positive PGC-like cells did retain methylation imprints of Igf2r and Snrpn, they appear to have a reduced level of methylation imprints of H19 and Kcnq1ot1, suggesting that the day-6 BVSC-positive cells initiate the process of imprint erasure (*Mech Dev* 117, 15-23 (2002)). Collectively, these results are a clear demonstration that PGC-like cell development from day-2 EpiLCs precisely recapitulates PGC specification and development in terms of gene expression and epigenetic reprogramming, and that the day-6 BVSC-positive cells bear highly similar, if not identical, properties to migrating PGCs at around ~E9.5 (*Development* 134, 2627-2638 (2007)).

Figure 3C:
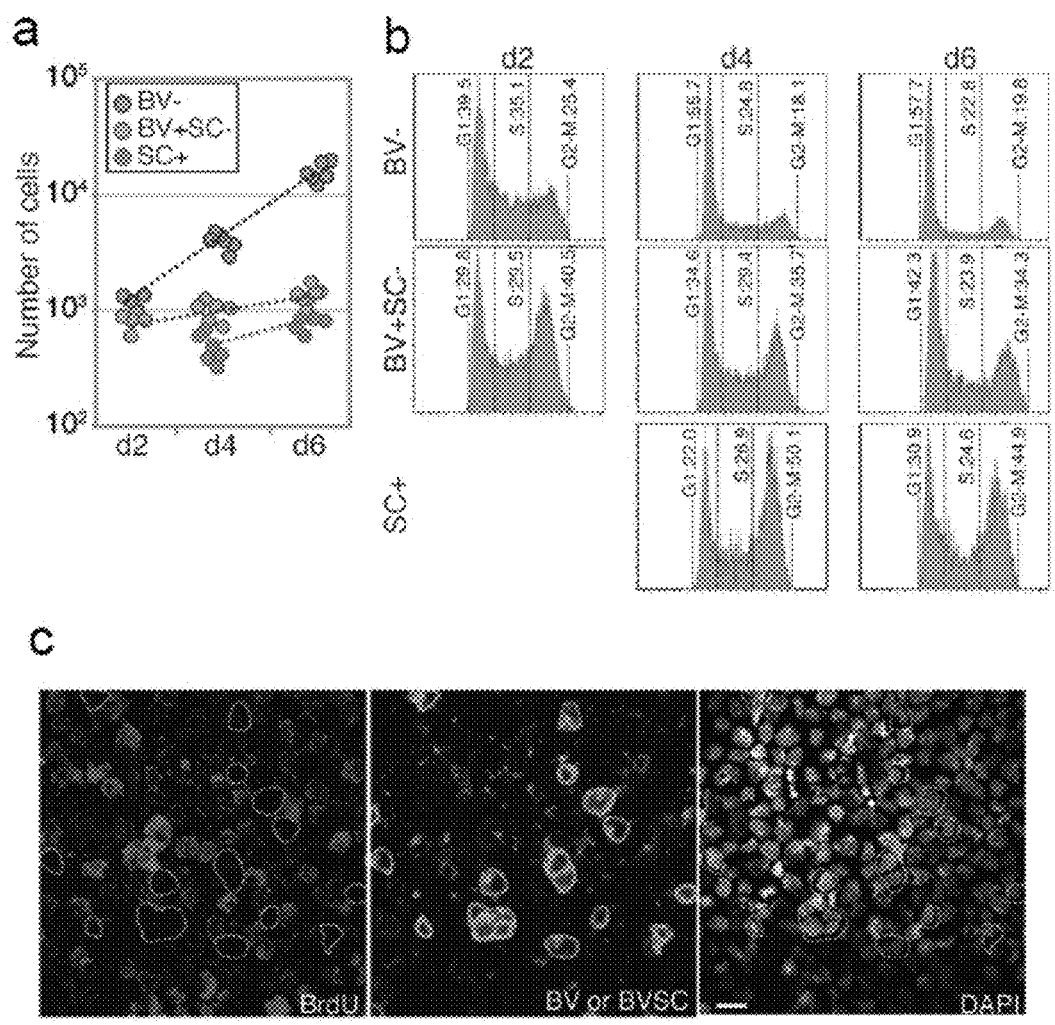
FIG. 3C, (a) The numbers of BVSC (+) (blue circles), BV(+)SC(−) (green circles), and BV(−) (grey circles) cells per aggregate during the PGCLC induction. Each circle represents the average number of each cell type from 10 aggregates in four independent experiments. (b) FACS analysis of the cell cycle states of BVSC(+), BV(+)SC(−), and BV(−) cells during the PGCLC induction. (c) BrdU incorporation of the PGCLCs during the 6-hr culture on day 4 of induction. Dotted lines delineate PGCLCs recognized by anti-GFP antibody staining. Bar, 20 µm.

We explored the dynamics of PGC-like cell induction and proliferation (FIG. 3C(a) and Table 2). At day 2 of PGC-like cell induction from aggregates of ~1,000 EpiLCs, the average number of strong BV(+) cells was 783 (~39%), whereas that of BV(−) cells was 1225 (~61%). At day 4, the average number of BV(+) cells was 1415 (~26%), among which 482 cells were SC(+) (~9%), whereas that of BV(−) cells was 3967 (~74%). At day 6, the average number of BV(+) cells was 2222 (~12%), among which 848 cells were SC(+) (~5%), whereas that of BV(−) cells was 15811 (~88%).

TABLE 2

Numbers of BV(−), BV(+)SC(−), BVSC(+) cells in d 2 EpiLC aggregates induced for the PGC fate for 6 days.

|  | d 0 | d 2 | d 4 | d 6 |
|---|---|---|---|---|
| BV− | 1000 | 1335 | 4052 | 15207 |
|  | 1000 | 1250 | 4745 | 14108 |
|  | 1000 | 971 | 4439 | 12201 |
|  | 1000 | 1343 | 3972 | 19187 |
|  | 1000 | N.D. | 2894 | 14416 |
|  | 1000 | N.D. | 3699 | 19746 |
| BV+SC− | 0 | 894 | 1048 | 1380 |
|  | 0 | 811 | 1255 | 1259 |
|  | 0 | 605 | 761 | 990 |
|  | 0 | 823 | 928 | 1746 |
|  | 0 | N.D. | 706 | 1435 |
|  | 0 | N.D. | 901 | 1436 |
| BVSC+ | 0 | 0 | 606 | 713 |
|  | 0 | 0 | 654 | 832 |
|  | 0 | 0 | 387 | 608 |
|  | 0 | 0 | 503 | 1267 |
|  | 0 | N.D. | 325 | 849 |
|  | 0 | N.D. | 418 | 819 |

Numbers of BV(−), BV(+)SC(−) and BVSC(+) cells at day 0 (d 0), day 2 (d 2), day 4 (d 4) and day 6 (d 6) of induction of d 2 EpiLC aggregates for the PGC fate are shown. Aggregates containing 1000 cells of d 2 EpiLCs were induced for the PGC fate. Average numbers of each cell type from 10 aggregates in four independent experiments were shown. N.D., not determined.

The cell cycle analysis revealed that BV(+) cells, especially BVSC(+) cells at days 4/6, were enriched in the G2 phase, whereas BV(−) cells exhibited profiles similar to those of cycling somatic cells, especially at days 4/6 (FIG. 3C(b)). Consistently, PGC-like cells did not incorporate BrdU efficiently during the 6-hr culture on day 4 of induction, whereas non-PGC-like cells actively incorporated it (FIG. 3C(c)). Collectively, these data indicate that BV induction from EpiLCs is an efficient process and presumably all the BV(+) cells initiate stella expression thereafter (irrespective of their SC positivity; see above), but the induced BV(SC)(+) cells proliferate slowly (one to two divisions from day 2 to day 6), whereas BV (−) cells grow more rapidly (three to four divisions). The slow growth and the arrest at the G2 phase of the cell cycle are key characteristics of migrating PGCs (Development 134, 2627-2638 (2007)), and the finding that PGC-like cells bear equivalent properties provides further evidence that PGC-like cell formation is a reconstitution of PGC formation.

Example 5

Spermatogenesis and Normal Offspring from PGC-Like Cells

Figure 4A:
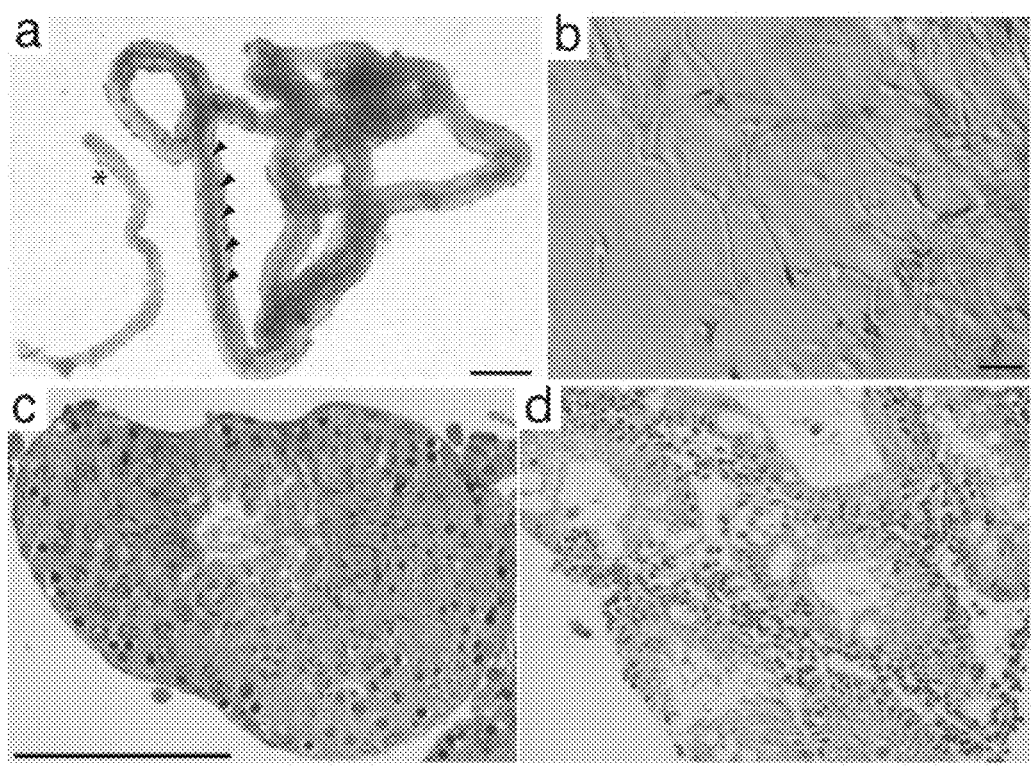
FIG. 4A, (a) Bright-field images of the seminiferous tubules with (right) or without (left) spermatogenesis transplanted with the PGC-like cells. Arrowheads indicate spermiated areas of the tubule. Bar, 500 µm. (b) Spermatozoa derived from the PGC-like cells. Bar, 20 µm. (c), (d) Hematoxylin and eosin-stained histological sections of the seminiferous tubules undergoing spermatogenesis (c) and those without spermatogenesis (d). Bar, 100 µm.
Figure 8:
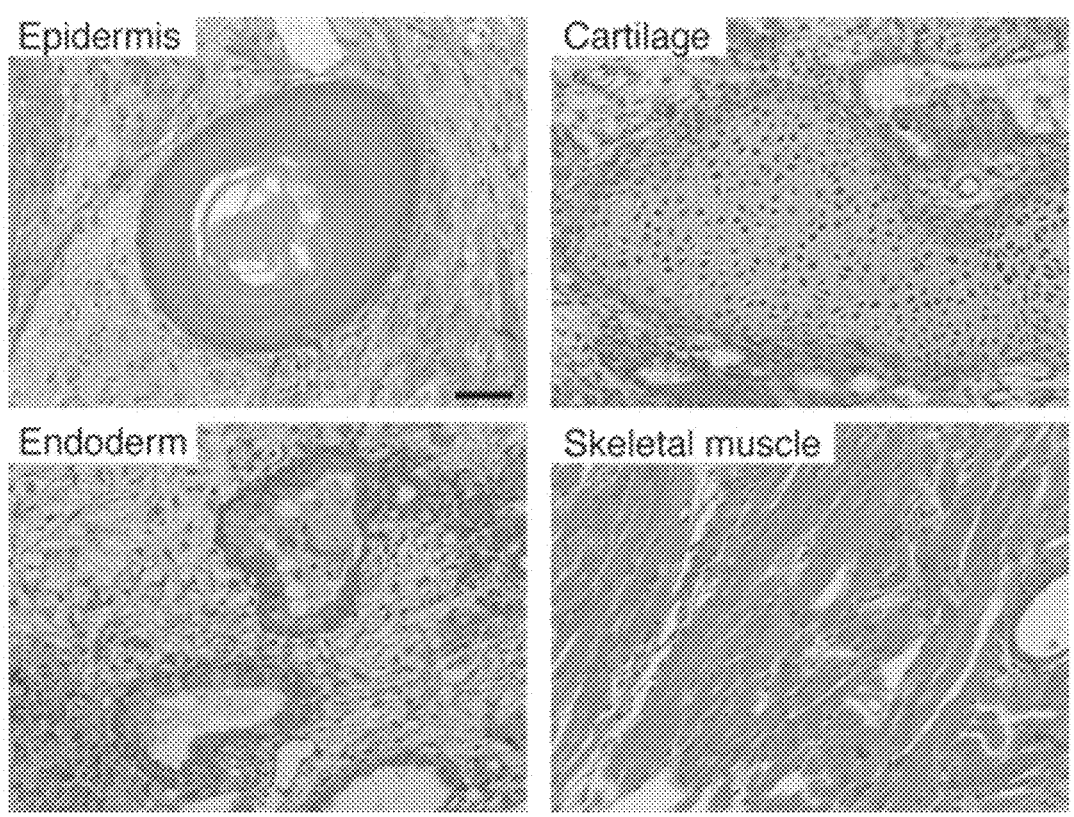
FIG. 8 shows generation of teratomas in the testes transplanted with non FACS-sorted cells induced at day 6 from the day-2 EpiLCs. Overt teratomas with cells of three germ layers were developed in the W/W$^v$ testes transplanted with non FACS-sorted, day-6 cells induced from the day-2 EpiLCs. Shown are the sections containing an epidermis-like structure (ectoderm), hyaline cartilages (mesoderm), epithelial structures with goblet cell-like cells (endoderm), and striated muscles (mesoderm). Bar, 50 µm.

To evaluate the function of PGC-like cells, we next examined whether the PGC-like cells undergo proper spermatogenesis by transplanting them into the seminiferous tubules of W/W$^v$ neonatal mice lacking endogenous germ cells (*Development* 132, 117-122 (2005)). The cell's ability to contribute to spermatogenesis is the most stringent index of whether it has become a male germ cell (*Cold Spring Barb Symp Quant Biol* 73, 17-23, doi:sqb.2008.73.033[pii] 10.1101/sqb.2008.73.033 (2008)). We induced the PGC-like cells from a line of BVSC ESCs for 6 days, transplanted dissociated single cells from the entire aggregates or the BV-positive cells sorted by FACS, and evaluated the recipient testes after 10 weeks. All the testes (8/8 and 6/6) transplanted with cells from the entire aggregates developed overt teratoma containing cells of three germ layers (FIG. 8 and Table 3). In sharp contrast, the testes transplanted with the FACS-sorted BV-positive cells did not show teratoma formation. Instead, remarkably, three out of six testes harboured seminiferous tubules with apparently proper spermatogenesis: the transplanted seminiferous tubules contained dark central sections apparently corresponding to spermiation, and these tubules were much thicker than those without spermatogenesis (FIG. 4A(a) and Table 3). Examination of the inside of the thick tubules indeed revealed the presence of abundant spermatozoa with normal morphology (FIG. 4A(b)). Histological examination of the thick tubules clearly showed a robust wave of spermatogenesis, whereas the thin tubules contained only Sertoli cells (FIG. 4A(c), (d)). The efficiency of the colonization of the PGC-like cells was similar to that of PGCs in vivo performed by our hands (*Cell* 137, 571-584 (2009)). These findings indicate that the PGC-like cells induced from ESCs bear an equivalent functional property to PGCs in vivo.

TABLE 3

Colonization of the donor cells in the W/W$^v$ recipient testes.

| Parental cells | Transferred population | No. of testes transplanted | No. of cells transplanted/ testis | No. of testes with teratoma (%) | No. of testes with spermato- genesis (%) | No. of spermatogenesis colonies in the testis |
|---|---|---|---|---|---|---|
| BVSC ESCs | Non-sorted cells | 8 | 2.9 × 10$^5$ | 8/8 (100) | N.D. | N.D. |
| | BV (+) cells | 6 | 1.1 × 10$^4$ | 0/6 (0) | 3/6 (50) | 4, 1, 1 |
| AAG ESCs | Non-sorted cells | 6 | 2.4 × 10$^4$ | 6/6 (100) | N.D. | N.D. |
| | Integrin-β3, SSEA1 (+) cells | 6 | 1.0 × 10$^4$ | 0/6 (0) | 5/6 (83) | 10, 8, 6, 3, 1 |
| 20D17 iPSCs | Integrin-β3, SSEA1 (+) cells | 18 | 1.0 × 10$^4$ | 0/18 (0) | 3/18 (17) | 6, 2, 1 |
| 178B-5 iPSCs | Integrin-β3, SSEA1 (+) cells | 6 | 1.0 × 10$^4$ | 2/6 (33) | 0/4 (0) | 0 |
| 492B-4 iPSCs | Integrin-β3, SSEA1 (+) cells | 6 | 1.0 × 10$^4$ | 0/6 (0) | 0/6 (0) | 0 |

Figure 4C:
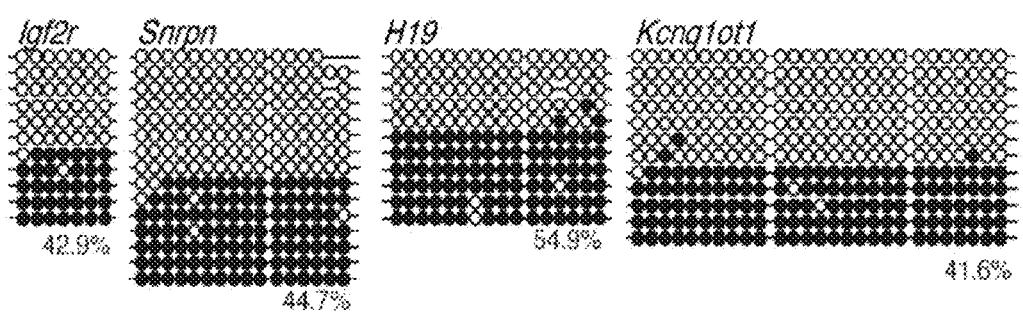
FIG. 4C, Bisulfite sequence analysis of the cytosine methylation of differentially methylated regions of the imprinted genes (Igf2r, Snrpn, H19, and Kcnq1ot1) in the genome from the tail of offspring derived from wild-type sperm (top) or spermatozoa from the PGC-like cells (bottom). White and black circles represent unmethylated and methylated CpG sequences, respectively.
Figure 4B:
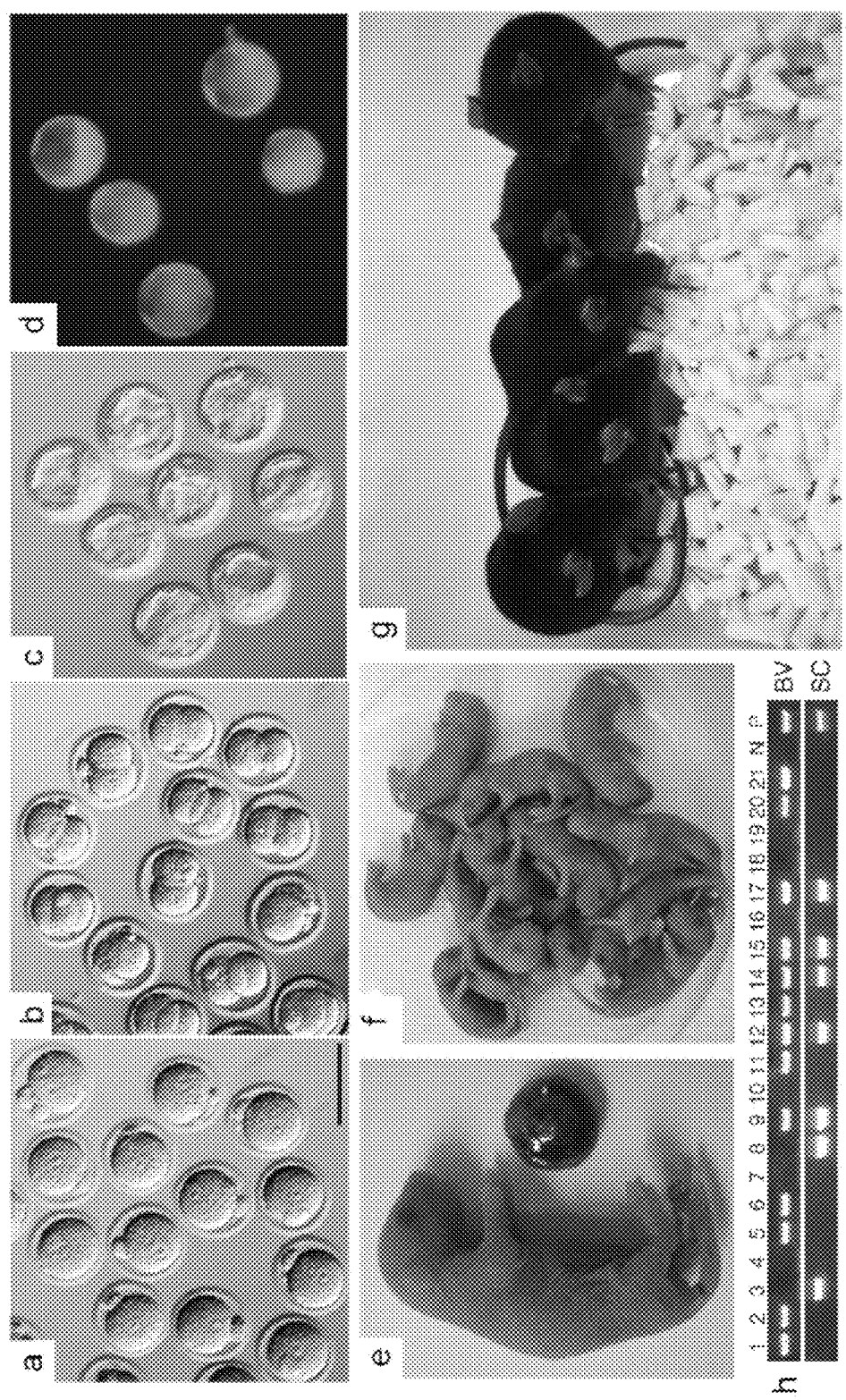
FIG. 4B, (a)-(d) The embryos at the pronucleus stage (a), the 2-cell embryos (b) and the blastocysts (c) with SC expression (h) derived from spermatozoa from the PGC-like cells. The SC transgenes were derived from the haploid paternal genome originally from the BVSC ESCs. Bar, 100 µm. (e), (f) The offspring with apparently normal placenta (e) derived from spermatozoa from the PGC-like cells. (g) A photograph of some of the offspring derived from spermatozoa from the PGC-like cells. (h) Genotypes of the offspring for BV and SC transgenes.
Figure 12:
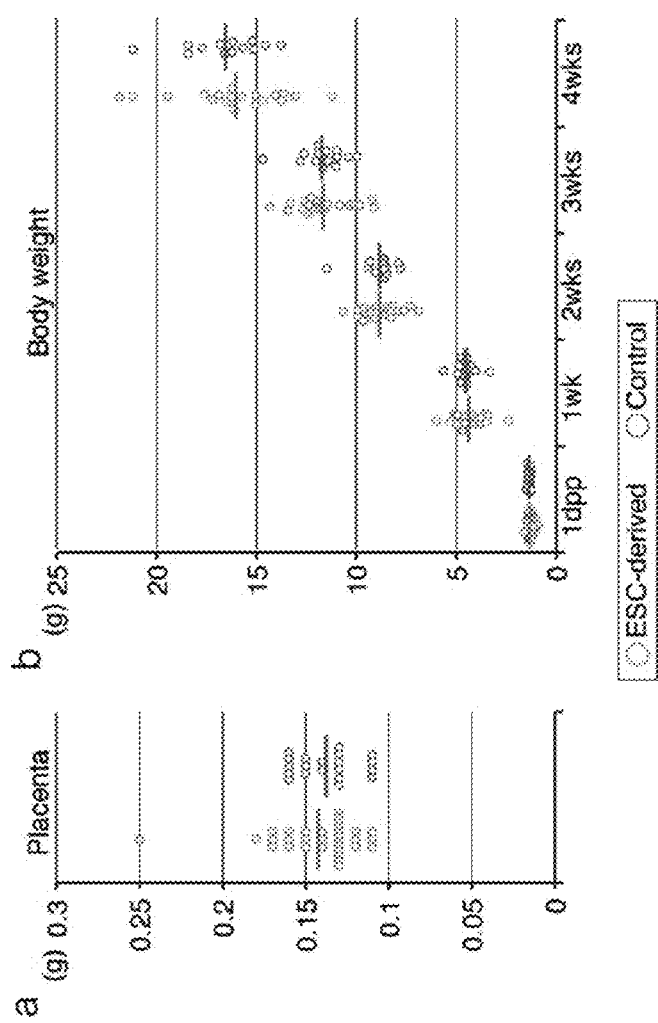
FIG. 12 shows placental weights and growth of the offspring from the PGC-like cell-derived sperm. (a) Weights (gram) of placentas of offspring from the PGCLC-derived sperm (red circles) and from the wild-type sperm (blue circles). The mean values are indicated as bars. (b) Development of the body weights of offspring from the PGC-like cell-derived sperm (red circles) and from the wild-type sperm (blue circles). The mean values are indicated as bars. (c) A fertile female offspring from the PGC-like cell-derived sperm.

We fertilized the wild-type oocytes with the spermatozoa derived from ESCs by intra-cytoplasmic sperm injection (ICSI). The resultant zygotes developed normally and by the blastocyst stage exhibited strong SC derived from the donor ESC genome (FIG. 4B(a)-(d) and Table 4). The transferred embryos gave rise to grossly healthy offspring with normal placentas and normal imprinting patterns (FIG. 4B(e)-(g), FIG. 4C). The BV and SC transgenes were positive for 13 and 7, respectively, out of 21 offspring (FIG. 4B(h)), consistent with the transmission of the transgenes through haploid donor spermatozoa. The offspring from the PGC-like cells developed normally and grew into fertile adults (FIG. 12 and Table 4). Based on all the evidence, we conclude and propose that our system is the first functional in vitro recapitulation of the germ-cell specification pathway from the ICM in vivo.

TABLE 4

Development of the oocytes injected with the spermatozoa derived from the PGCLCs in culture.

| Origin of sperm | No. of oocytes survived after ICSI | No. of oocytes forming pronuclei (%) | No. of 2-cell embryos (%) | No. of embryos transferred | No. of pups (%) |
|---|---|---|---|---|---|
| BVSC ESCs | 182 | 171 (94.0) | 151 (88.3) | 145 | 32 (22.1) |
| AAG ESCs | 78 | 70 (89.7) | 63 (90.0) | 63 | 33 (52.4) |
| 20D17 iPSCs | 40 | 31 (77.5) | 27 (87.1) | 27 | 7 (25.9) |
| C57BL/6 testis (Control) | 53 | 46 (86.8) | 41 (89.1) | 37 | 20 (54.1) |

For the spermatozoa derived from PGCLCs from ESCs, 115 2-cell- and 30 molura/blastocyst-stage embryos were transferred to 0.5- and 2.5-dpc (days post coitum) pseudopregnant females, respectively. For the control experiment, 37 2-cell stage embryos were transferred to 0.5-dpc pseudopregnant females.

Example 6

Identification of Surface Markers for PGC-Like Cell Isolation

Figure 13A:
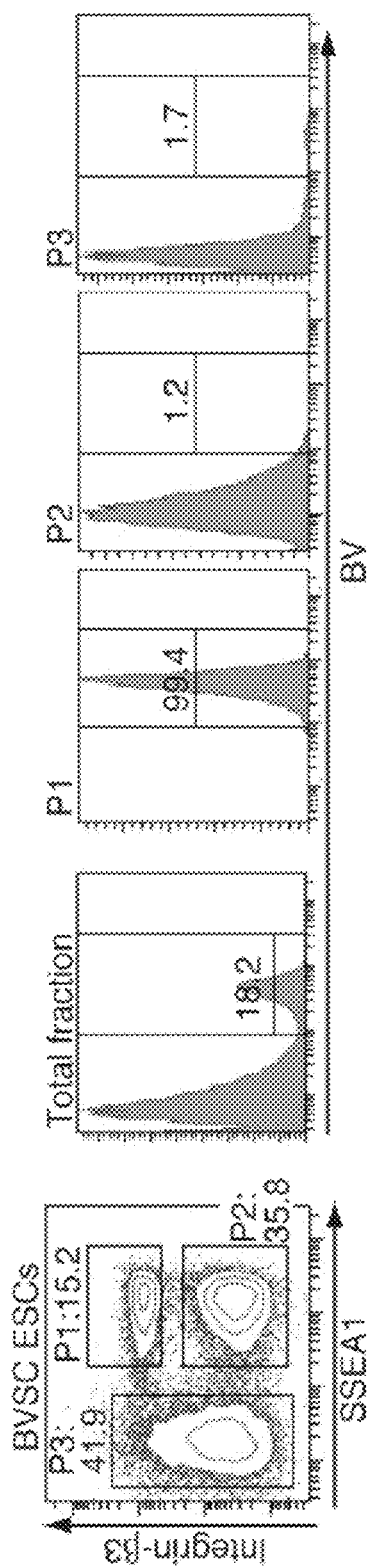
FIG. 13A, FACS sorting by SSEA1 and Integrin-β3 of day-6 aggregates for the PGC fate from BVSC ESCs (left panel). The SSEA1/Integrin-β3 high P1 sub-population is nearly identical to the BV(+) sub-population (right panels). Numbers represent the percentages of each sub-population.

Identification of surface markers delineating a pure population of PGC-like cells is essential for isolating PGC-like cells from PSCs without appropriate transgenic reporters, such as iPSCs or ESCs from various mammalian species, including humans (*Reproduction* 139, 931-942 (2010)). We screened surface markers (SSEA1, PECAM1, EPCAM, N-cadherin, Integrin-β3, Integrin-αV, CXCR4, and KIT) and their combinations to identify those that define the BV(+) population. When aggregates of BVSC d2 EpiLCs induced for 6 days were FACS-sorted by SSEA1 and Integrin-β3, they were divided into three major sub-populations [P1 (SSEA1 high, Integrin-β3 high), P2 (SSEA1 high, Integrin-β3 low), and P3 (SSEA1 low, Integrin-β3 high/low)]. Notably, more than 99% of the cells in P1 were BV(+), whereas only 1.2% and 1.7% of the cells in P2 and P3, respectively, contained BV(+) cells (FIG. 13A), indicating that P1 is nearly identical to the BV(+) population.

Figure 13B:
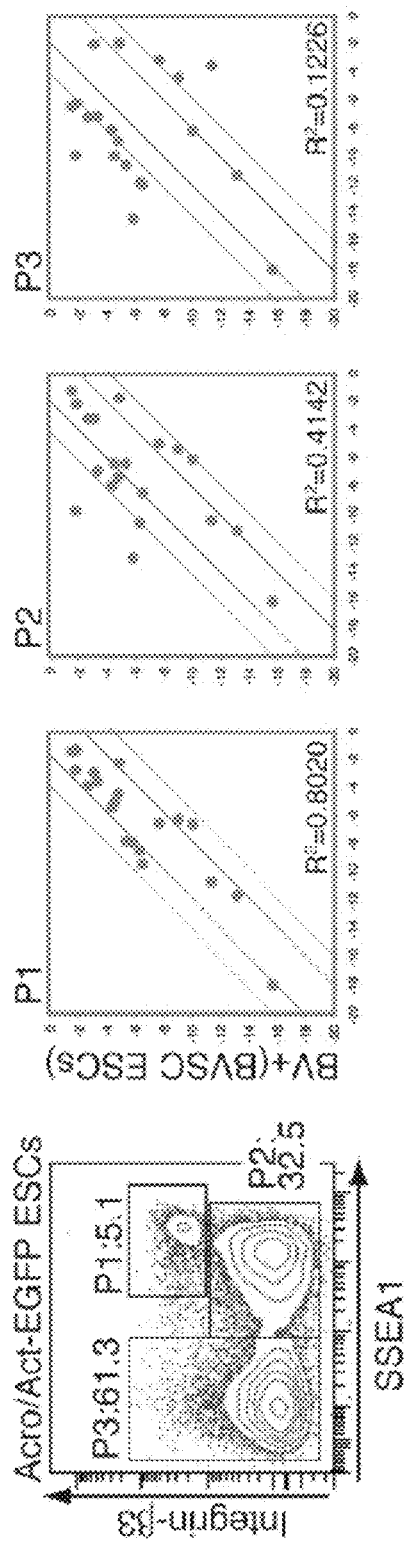
FIG. 13B, FACS sorting by SSEA1 and Integrin-β3 of day-6 aggregates for the PGC fate from AAG ESCs (left panel). Comparison of expression levels of the 20 genes (those analyzed in FIG. 2E) in each sub-population (P1, P2, and P3) with those in BV(+) cells (right panels). $R^2$ represents the correlation coefficient.

We induced ESCs bearing Acro/Act-EGFP (AAG) transgenes (*Dev Growth Differ* 42, 105-112 (2000)) into PGC-like cells and FACS-sorted the day-6 aggregates by SSEA1 and Integrin-β3. Although the sorting pattern of these aggregates was somewhat different from that of the aggregates from BVSC ESCs, we identified three similar sub-populations (FIG. 13B). We compared the expression levels of 20 genes analyzed in FIG. 2E in these sub-populations with those in BV(+) PGC-like cells. The expression levels of the 20 genes in P1 correlated well with those in BV(+) PGCLCs ($R^2$=0.80), whereas those in the other two subpopulations showed poor correlation (FIG. 13B).

Figure 13C:
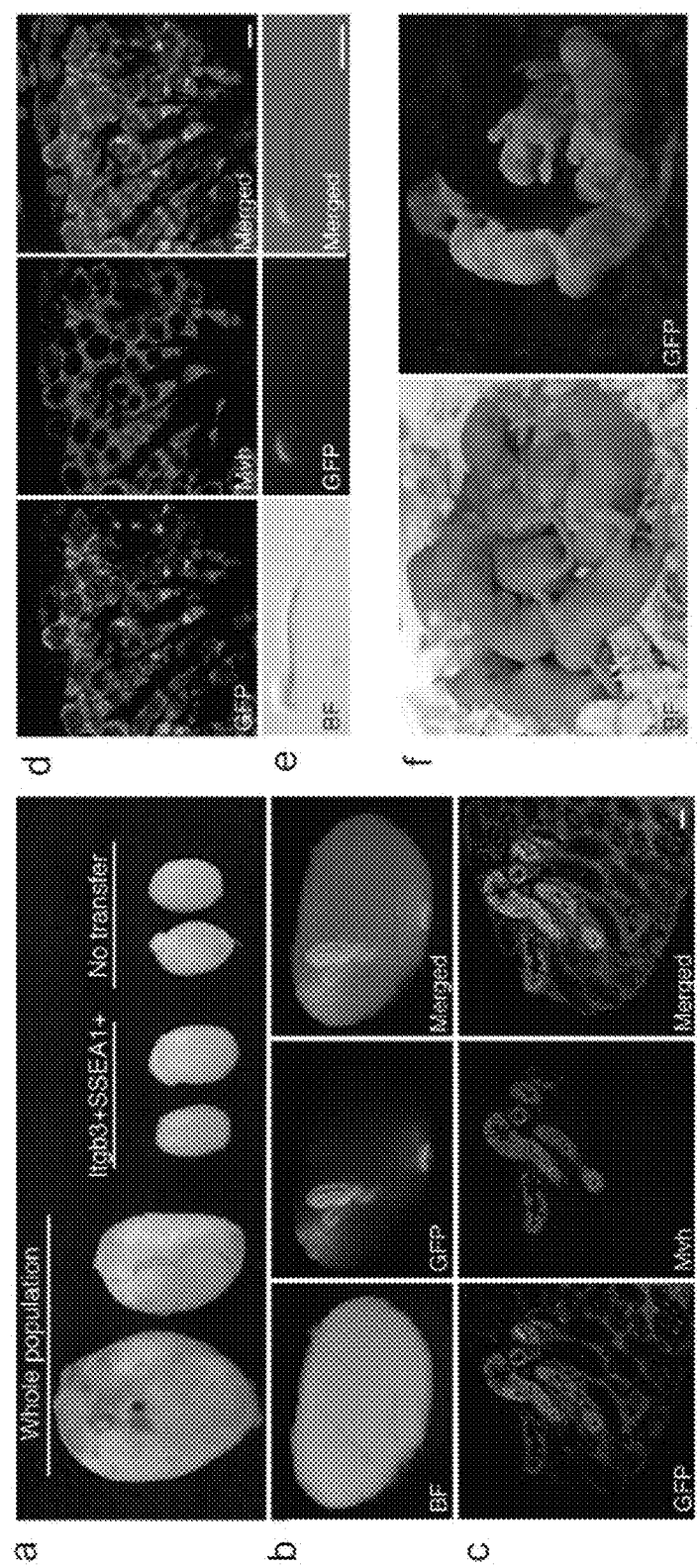
FIG. 13C, (a) Testes of W/W$^v$ mice transplanted with the whole population (left), the P1 sub-population (middle), and no cells (right) of aggregates of day 2 EpiLCs with AAG transgenes induced for the PGC fate for 6 days. (b) Spermatogenic colonies in a W/W$^v$ testis transplanted with the P1 sub-population. BF: bright field image. (c), (d) Immunofluorescence (IF) analysis of EGFP and Mvh expression in a spermatogenic colony in (a). Bar in (c), 100 µm; in (d), 10 µm. (e) Spermatozoa derived from AAG ESCs. Bar, 10 µm. (f) The offspring derived from spermatozoa from AAG ESCs. About half of them show GFP fluorescence from AAG transgenes (right).

To examine whether the P1 sub-population from AAG ESCs contributes to the spermatogenesis, we transplanted them as well as the whole population into the seminiferous tubules of W/W$^v$ mice and evaluated the recipients after 8 weeks. We found teratoma in all the testes transplanted with the whole population, whereas we detected no teratoma in testes with the P1 sub-population, and instead, 5 out of 6 testes demonstrated proper spermatogenesis with GFP fluorescence by the AAG transgenes (FIG. 13C(a)-(e), Table 3). The resultant sperm contributed to the healthy and fertile offspring with the 12 ICSI followed by the embryo transfer procedures (FIG. 13C(f) and Table 4). These findings demonstrate that the sorting by SSEA1 and Integrin-β3 purifies PGC-like cells with essentially no contamination of teratogenic undifferentiated cells, establishing the formation and purification of PGC-like cells from ESCs without any relevant transgenic markers.

Example 7

Figure 9A:
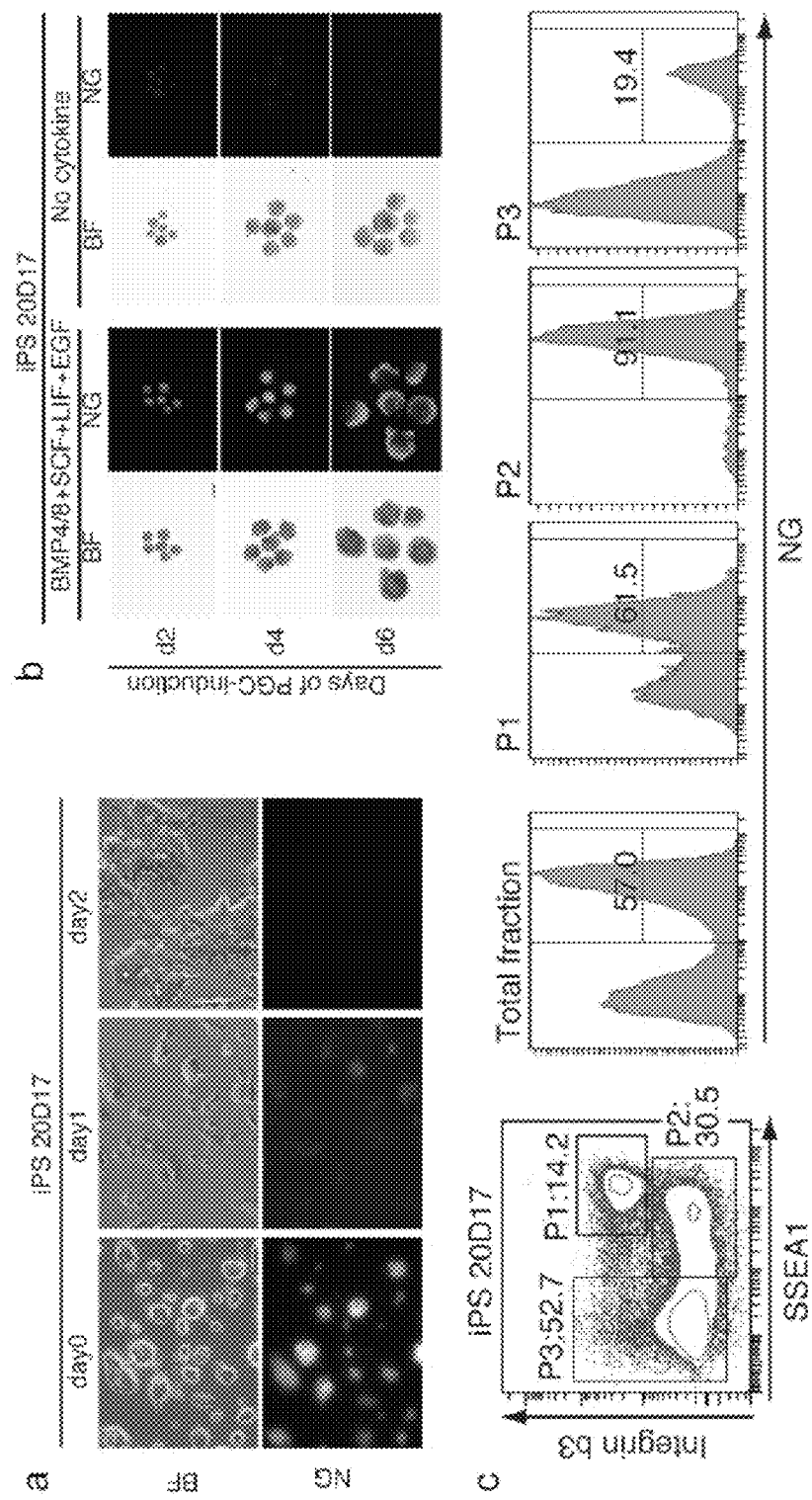
FIG. 9 shows an induction of the PGC-like cells, spermatogenesis and offspring from iPSCs (20D17 (FIG. 9A), 178B-5 (FIG. 9B), 492B-4 (FIGS. 9C, 9D)) through EpiLCs. (a) Induction of the EpiLCs from iPSCs with the Nanog-EGFP transgene. Bright-field images (BF) and fluorescence images from the transgene (NG) are shown. The EpiLCs inductions were performed over two days. Bar, 50 µm. (b) Induction of the PGC-like cells from EpiLCs. The day-2 EpiLCs developed as PGC-like cells with Nanog expression under the full induction condition. Bar, 200 µm. (c) FACS sorting by SSEA1 and Integrin-β3 of day-6 aggregates for the PGC fate derived from iPSCs (left panel). NG expression levels in the P1 (SSEA1 high, Integrin-β3 high), P2 (SSEA1 high, Integrin-β3 low), and P3 (SSEA1 low, Integrin-β3 low) sub-populations as well as in the total population are shown in the right panels.
FIG. 9D, Gene expression profiles during the EpiLC induction from iPSCs (492B-4) measured by Q-PCR. For each gene examined, the ΔCT from the average CT values of the two independent housekeeping genes Arbp and Ppia was calculated. The value for iPSCs was set as 0. For each point, the average value from two independent experiments is shown on the log$_2$ scale.
FIG. 9E, FACS sorting by SSEA1 and Integrin-β3 of day-6 aggregates for the PGC fate derived from iPSCs (20D17) (left panel). Comparison of expression levels of the 20 genes (those analyzed in FIG. 2E) in each sub-population (P1, P2, and P3) with those in BV(+) cells (right panels). R$^2$ represents the correlation coefficient.
FIG. 9F, (a) (left panel) The seminiferous tubules transplanted with the PGC-like cells from iPSCs, showing (right) or not showing (left) spermatogenesis. Arrowheads indicate spermiated areas of the tubule. Bar, 500 µm. (right panel) Spermatozoa derived from the PGC-like cells from iPSCs. Bar, 20 µm. (b) The offspring derived from spermatozoa from iPSCs. Genotyping of the offspring for NG and Oct4 (for iPSC generation) transgenes is shown at the bottom.
Figure 9B:
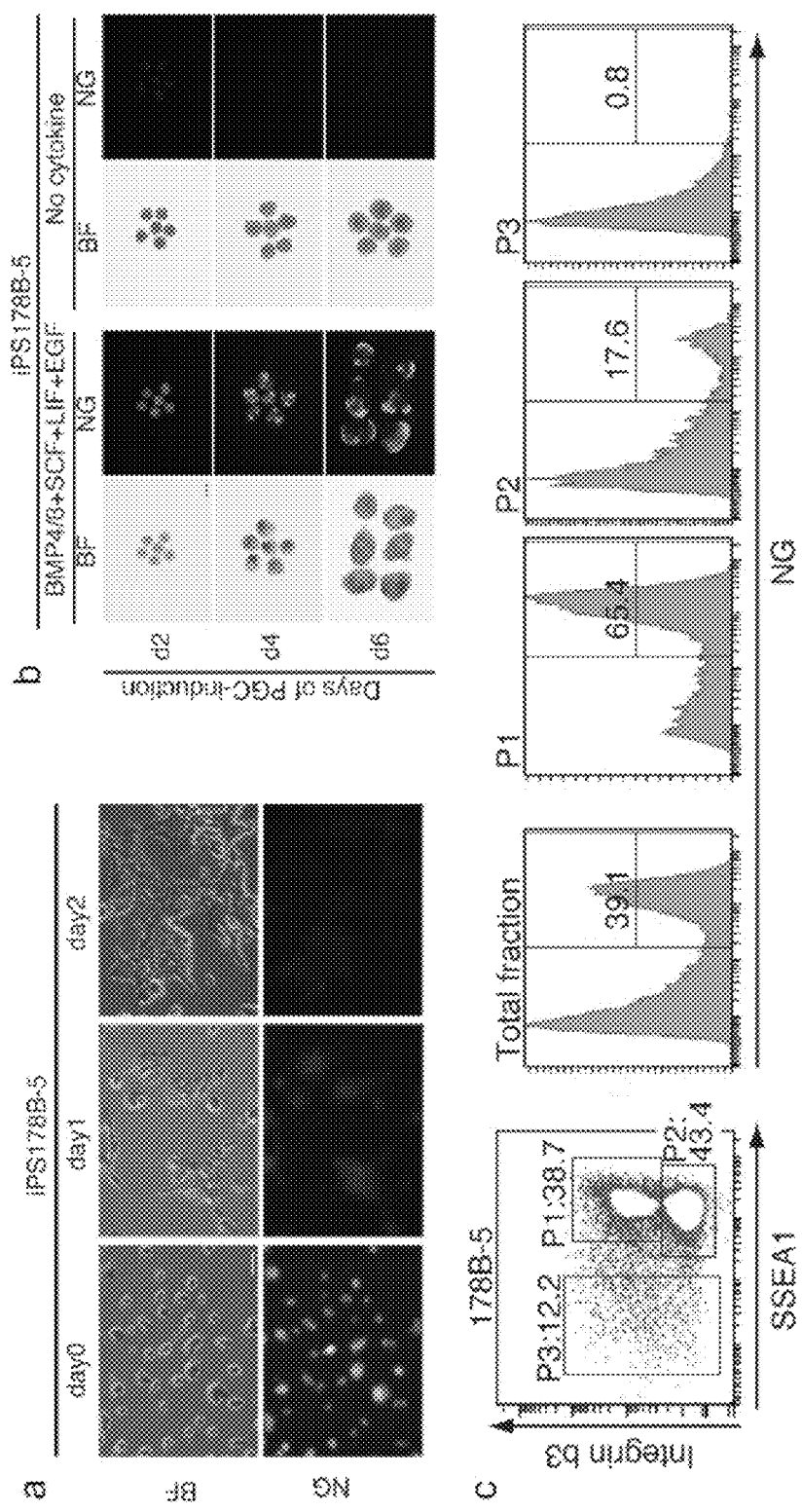
Figure 9C:
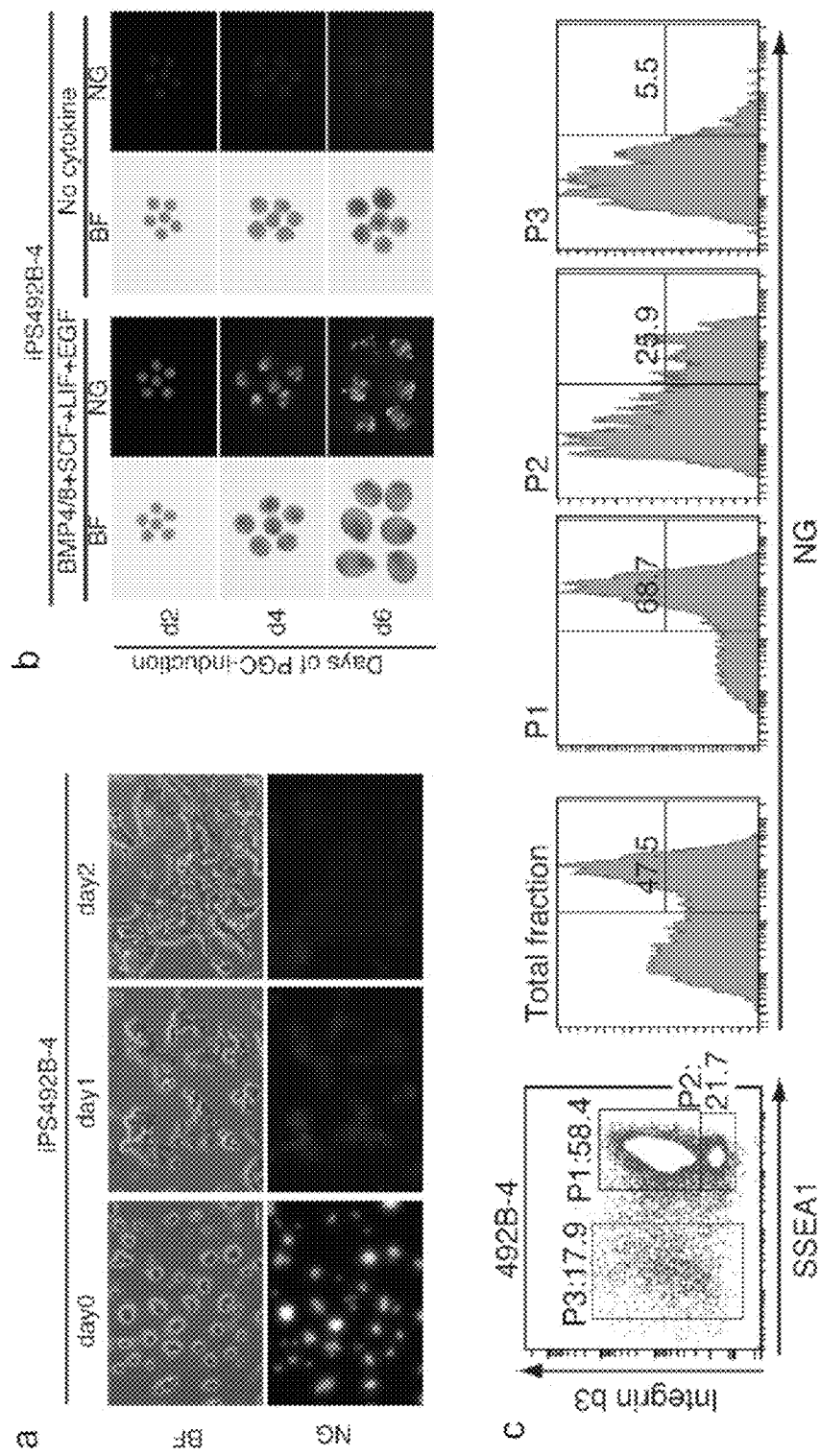
Figure 9D:
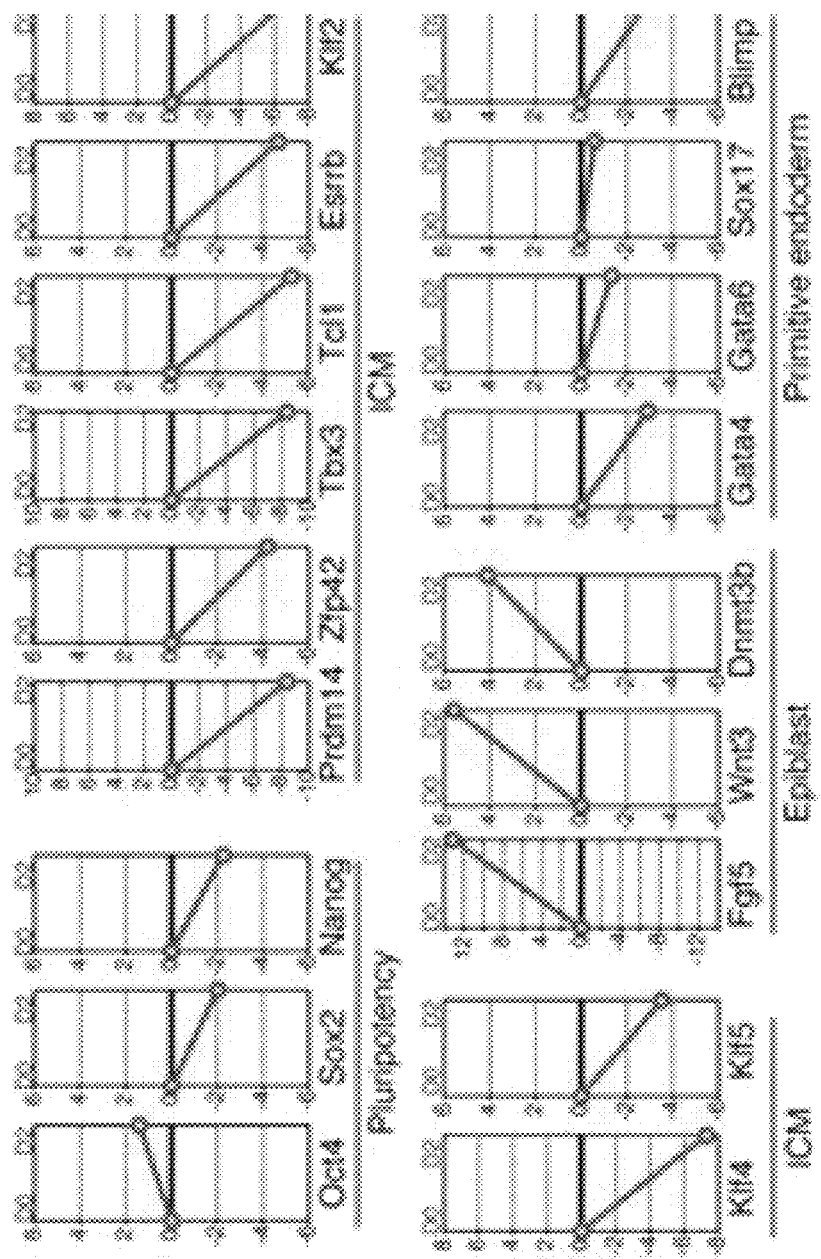

PGC-Like Cell Induction from iPSCs Through EpiLCs, Spermatogenesis and Offspring from PGC-Like Cells EpiLCs and PGC-like cells were induced from iPSCs in the same manner as Examples 1 and 2, and characterized by immunofluorescence and Q-PCR. As mouse iPSCs, iPS178B-5 (*Nat Biotechnol* 26, 101-106 (2008)) produced by the introduction of 3 genes (Oct3/4, Sox2, Klf4) and iPS492B-4 (*Science* 322, 949-953 (2008)) and 20D17 (*Nature* 448, 313-317 (2007)) produced by the introduction of 4 genes (Oct3/4, Sox2, Klf4, c-Myc), all bearing Nanog-EGFP (NG) transgenes, were used. The results of analyses are shown in FIG. 9. Likewise in the case of ESCs, the introduction of differentiation of iPSCs into EpiLCs for 2 days resulted in morphological alterations to an epiblast-like structure. Immunofluorescence revealed that Nanog expression rapidly disappeared during the EpiLC induction (FIG. 9A-9C, (a)). Next, Q-PCR was performed to characterize the EpiLCs obtained in the same manner as Example 1. As a result, the EpiLCs obtained from iPSCs by inducing differentiation for 2 days showed down-regulation of genes tightly associated with the ICM state and elevated expression of genes up-regulated in epiblasts, similar to the EpiLCs derived from ESCs. In addition, endoderm markers were down-regulated likewise the ESC-derived EpiLCs (FIG. 9D).

We next examined whether the EpiLCs derived from iPSCs were induced into PGC-like cells, as in the case of those derived from ESCs. The EpiLCs were cultured under the "full induction conditions" (in SFM containing BMP4, LIF, SCF, BMP8b and EGF) for 6 days. Cell aggregates expanded along with the PGC-like cell induction as in the case of ESC-derived EpiLCs. Nanog-positive cells were detected in the peripheral zone of cell aggregates on day 6 of the cultivation, as in the case of BVSC-positive cells when inducing differentiation of ESC-derived EpiLCs into PGC-like cells (FIG. 9A-9C, (b)).

We FACS-sorted the induced aggregates at day 6 by SSEA1 and Integrin-β3. The sorting patterns of the three lines were somewhat different from one another and that of the 20D17 line was more similar to those of the ESC lines (FIG. 9A-9C, (c) and FIG. 9E). In aggregates of the 20D17 line, NG-positive cells represented ~57% (FIG. 9A(c)). Consistent with the characteristics of migrating PGCs, the P1 sub-population contained both NG-high and -low cells (FIG. 9A(c)) (*Gene Expr Patterns* 5, 639-646 (2005)). On the other hand, the P2 sub-population enriched NG-high cells, likely representing an undifferentiated population (FIG. 9A(c)).

Figure 9E:
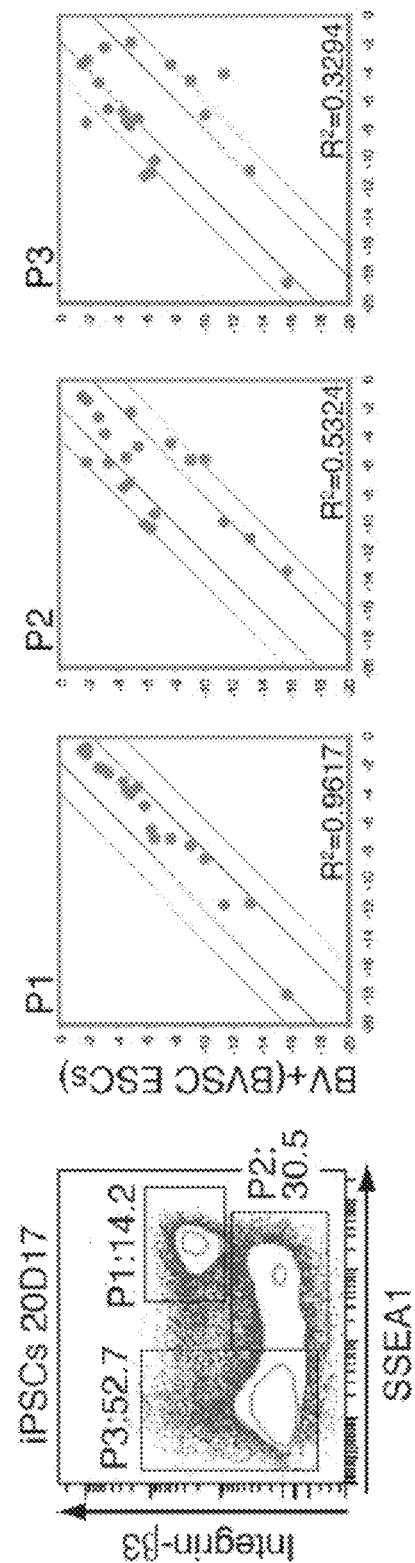
Figure 9F:
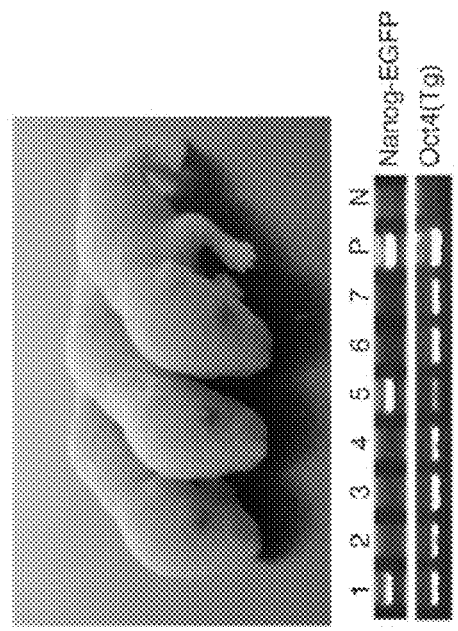
Figure 9F:
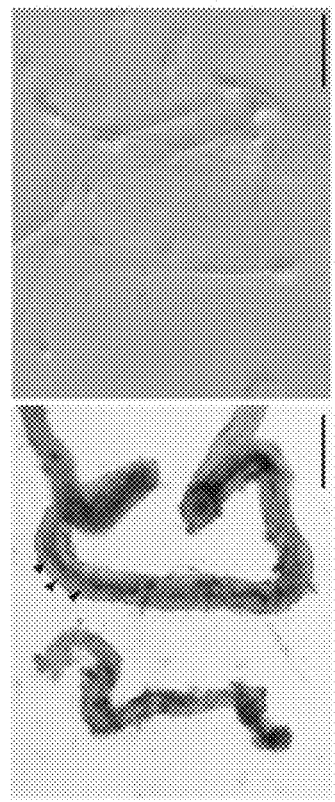

The expression levels of the 20 genes analyzed in FIG. 2E in the P1 sub-population from the 20D17 line exhibited a prominent correlation with those in BV(+) PGC-like cells ($R^2$=0.96), whereas those in the other two sub-populations showed a poor correlation (FIG. 9E). We transplanted the P1 cells from the three lines into the seminiferous tubules of W/W$^v$ mice and evaluated the recipients after 10 weeks. No testes with cells from the 178B-5 or 492B-4 lines showed spermatogenesis and 2 with the 178B-5 cells resulted in teratoma (Table 3). Remarkably, 3 out of 18 testes with the cells from the 20D17 line exhibited proper spermatogenesis and we observed no teratoma in the recipients of this line (FIG. 9F(a) and Table 3). The resultant sperm contributed to the fertile offspring with the ICSI followed by the embryo transfer procedures (FIG. 9F(b), Table 4). Notably, some of the offspring died prematurely apparently due to tumors around the neck region (data not shown), similar to those observed in some of the F1 offspring of the 20D17 chimeras (*Nature* 448, 313-317 (2007)). These findings demonstrate that although iPSCs exhibit different induction properties depending on the lines, they can nonetheless form PGC-like cells with proper function in vitro.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent application No. 61/373,563, the contents of which are hereby incorporated by reference.

The invention claimed is:

1. A method of producing a primordial germ cell-like (PGC-like) cell from a human or mouse pluripotent stem cell, comprising the steps of:
   I) culturing a human or mouse pluripotent stem cell in the presence of activin A, bFGF, and 0.3 to 3 w/w % KSR for 48±12 hours to obtain an epiblast-like cell (EpiLC),
   II) culturing the EpiLC obtained in step I) in the presence of BMP4 and LIF, to obtain a PGC-like cell,
   wherein the pluripotent stem cell is a human or mouse induced pluripotent stem cell (iPSC) or a human or mouse embryonic stem cell (ESC).

2. The method of claim 1, wherein the human or mouse PGC-like cell shows elevated gene expression of Blimp1 and/or Stella (Dppa3) compared to the EpiLC before inducing differentiation.

3. The method of claim 1, wherein the human or mouse PGC-like cell is capable of contributing to normal spermatogenesis.

4. The method of claim 1, wherein the culture in the step II) is performed in the presence of further SCF and/or BMP8b and/or EGF.

5. The method of claim 1, wherein the culture in the step II) is performed under serum-free conditions.

6. The method of claim 1, wherein the culture in step II) is performed in the presence of BMP4, LIF, SCF, BMP8b and EGF.

7. The method of claim 1, which further comprises:
   III) a step for selecting a Blimp1-positive cell from the cells obtained in step II).

8. The method of claim 1, which further comprises:
   III) a step for selecting a SSEA1- and Integrin-β3-double positive cell from the cells obtained in step II).

9. The method of claim 1, wherein the ESC is acquired by a method in which a mammalian inner cell mass in the blastocyst stage is cultured or by a method in which an early embryo prepared by somatic cell nuclear transfer is cultured.

10. The method of claim 1, wherein the concentration of activin A in step I) is 10 to 30 ng/mL.

11. The method of claim 10, wherein the concentration of bFGF in step I) is 7.5 to 20 ng/mL.

12. The method of claim 1, wherein the concentration of bFGF in step I) is 7.5 to 20 ng/mL.

* * * * *